United States Patent
Rosier et al.

(10) Patent No.: US 6,893,841 B2
(45) Date of Patent: May 17, 2005

(54) NUCLEIC ACIDS OF THE HUMAN ABCC11 GENE, VECTORS CONTAINING SUCH NUCLEIC ACIDS AND USES THEREOF

(75) Inventors: Marie Rosier, Antony (FR); Catherine Prades, Thiais (FR); Isabelle Arnould, Chennevieres sur Marne (FR); Michael Dean, Frederick, MD (US); Rando Allikmets, Cornwall-on-Hudson, NY (US); Patrice Denefle, Saint Maur (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/087,782

(22) Filed: Mar. 5, 2002

(65) Prior Publication Data

US 2003/0059793 A1 Mar. 27, 2003

Related U.S. Application Data

(60) Provisional application No. 60/272,757, filed on Mar. 5, 2001.

(51) Int. Cl.⁷ .......................... C12N 15/12; C12N 5/10; C12P 21/02; C07K 14/47

(52) U.S. Cl. .................... 435/69.1; 435/320.1; 435/471; 435/252.3; 435/325; 435/71.1; 530/23.5; 530/351

(58) Field of Search .............................. 435/69.1, 71.1, 435/320.1, 471, 252.3, 325; 536/23.5; 530/351

(56) References Cited

PUBLICATIONS

Schuetz et al. MRP4: A previously unidentified factor in resistance to nucleoside–based antiviral drugs. Nature Medicinie, vol. 5, No. 9, pp. 1048–1051, Sep. 1999.

Wijnhods et al. Multidrug–resistance protein 5 is a multi-specific organic anion transporter able to transport nucleotide analogs. PNAS, vol. 97, No. 13, pp. 7476–7481, Jun. 2000.

*Primary Examiner*—Janet Andres
*Assistant Examiner*—Fozia Hamud

(57) ABSTRACT

The present invention relates to nucleic acids corresponding to various exons of the ABCC11 gene as well as the cDNA encoding the novel full length of ABCC11 protein. The invention also relates to means for the detection of polymorphisms in general, and of mutations in particular, in the ABCC11 gene or in the corresponding protein produced by the allelic form of the ABCC11 gene.

10 Claims, 5 Drawing Sheets

FIGURE 1

NUCLEIC ACIDS OF THE HUMAN ABCC11 GENE, VECTORS CONTAINING SUCH NUCLEIC ACIDS AND USES THEREOF

This application claims the benefit of provisional application No. 60/272,757, filed on Mar. 5, 2001, the content of which is incorporated herein by reference.

The present invention relates to a novel nucleic acid corresponding to ABCC11 gene, and a cDNA encoding the novel ABCC11 protein. The invention also relates to means for the detection of polymorphisms in general, and mutations in particular in the ABCC11 gene or corresponding proteins produced by the allelic forms of the ABCC11 gene.

The ATP-binding cassette (ABC) transporter superfamily is one of the largest gene families and encodes a functionally diverse group of membrane proteins involved in energy-dependent transport of a wide variety of substrates across membranes (Dean et al., *Curr Opin Genet Dev*, 1995, 5, 779–85). The active transporter proteins constitute a family of proteins that are extremely well conserved during evolution, from bacteria to humans (Ames and Lecar, FASEB J., 1992, 6, 2660–2666). The ABC proteins are involved in extra- and intracellular membrane transport of various substrates, for example ions, amino acids, peptides, sugars, vitamins or steroid hormones. Among the 40 characterized humans members, 11 members have been described as associated with human disease, such as inter alia ABCA1, ABCA4 (ABCR) and ABCC7 (CFTR), which are thought to be involved in Tangier disease (Bodzioch M et al., *Nat. Genet.*, 1999, 22(4); 347–351; Brooks-Wilson et al., *Nat Genet.*, 1999, 22(4), 336–345; Rust S et al., *Nat. Genet.*, 1999, 22, 352–355; Remaley A T et al., ), Stargardt disease (Lewis R A et al., *Am. J Hum. Genet.*, 1999, 64, 422–434), and cystic fibrosis (Riordan J M et al., *Science*, 1989, 245, 1066–1073), respectively. These implications reveal the importance of the functional role of the ABC gene family and the discovery of new family gene members should provide new insights into the physiopathology of human diseases.

The prototype ABC protein binds ATP and uses the energy from ATP hydrolysis to drive the transport of various molecules across cell membranes. Most ABC functional proteins from eukaryotes encode a full-transporter, each consisting of two ATP-binding domains (nucleotide binding fold, NBF) and two transmembrane (TM) domains. Most full-transporters are arranged in a TM-NBF-TM-NBF fashion (Dean et al., *Curr Opin Genet*, 1995, 5, 79–785).

Analysis of amino acids sequence alignments of the ATP-binding domains has allowed the ABC genes to be separated into sub-families (Allikmets et al., *Hum Mol Genet*, 1996, 5, 1649–1655). Currently, according to the recent HUGO classification, seven ABC gene sub-families named ABC A to G have been described in the human genome, i.e., ABCA (ABC1 subfamily), ABCB (MDR/TAP subfamily), ABCC (CFTR/MRP subfamily), ABCD (ALD subfamily), ABCE (OABP subfamily), ABCF (GCN20 subfamily), and ABCG (white subfamily). For the most part these subfamilies contain genes that also display considerable conservation in the transmembrane domain sequences and have similar gene organization. However, ABC proteins transport very various substrates, and some members of different subfamilies have been shown to share more similarity in substrate recognition than do proteins within same subfamily. Five of the subfamilies are also represented in the yeast genome, indicating that these groups have been and retained early in the evolution of eukaryotes (Decottignies et al., *Nat Genet*, 1997, 137–45; Michaelis et al., 1995, Cold Spring Harbor Laboratory Press).

Several ABC transport proteins that have been identified in humans are associated with various diseases. Some multiple drug resistance phenotypes in tumor cells have been associated with the gene encoding the MDR (multi-drug resistance) protein, which also has an ABC transporter structure. Other ABC transporters have been associated with neuronal and tumor conditions (U.S. Pat. No. 5,858,719) or potentially involved in diseases caused by impairment of the homeostasis of metals (*Biochim Biophys Acta.* Dec. 6, 1999;1461 (2):18–404).

The human ABCC subfamily currently has ten identified members (ABCC1 to 10), seven of which are from the multidrug resistance-like (MRP) subgroup, two from the sulfonylurea receptor (SUR) subgroup, and the CFTR gene. MRP-like proteins are organic anion transporters; i.e., they transport anionic drugs, exemplified by methotrexate (MTX), as well as neutral drugs conjugated to acidic ligands, such as glutathione (GSH), glucuronate, or sulfate, and play a role in resistance to nucleoside analogs (Cui et al., *Mol Pharmacol*, 1999, 55, 929–37; Kool et al., *Proc Natl Acad Sci*, 1999, 96, 6914–9; Schuetz et al., *Nat Med*, 1999, 5, 1048–51; Wijnholds et al., *Proc Natl Acad Sci*, 2000, 97, 7476–81). More specifically, ABCC1, ABCC2 and ABCC3 transport drugs conjugated to GSH, glucuronate, sulfate and other organic anions, such as MTX, whereas ABCC4 and ABCC5 proteins confer resistance to nucleotide analogs, including PMEA and purine base analogs. Several genetic variations in some ABCC subfamily members have been identified as associated with various human inherited diseases. For example, cystic fibrosis is caused by mutations in the ABCC7 gene or CFTR (cystic fibrosis transmembrane conductance regulator) gene (Riordan et al., *Science*, 1989, 245, 1066–73). Another member of the ABCC subfamily, the ABCC2 gene, has been associated with the Dubin-Johnson syndrome (Wada et al., *Hum Mol Genet*, 1998, 7, 203–7). Also, mutations in the coding sequence of another gene belonging to the ABCC subfamily, the ABCC6 gene, have been recently identified as responsible of the phenotype of pseudoxanthoma elasticum (Bergen et al., *Nat. Genet.*, 2000, 25, 228–31; Le Saux et al., *Nat Genet*, 2000, 25, 223–7), which is a genetic disorder of the connective tissue. Likewise, a receptor of sulfonylureas, ABCC8 or SUR1, appears to be involved in familial persistent hyperinsulinemic hypoglycemia of infancy (Thomas et al., *Science*, 1995, 268, 426–9).

Therefore, characterization of a new gene from the ABCC subfamily is likely to yield a biologically important transporter that may have a translocase activity and may play a major role in human pathologies.

The applicants have discovered and characterized a novel gene belonging to the ABCC protein sub-family, which has been designated ABCC11. The newly discovered gene also shows considerable conservation of the amino acid sequences, particularly within the transmembrane region (TM) and the ATP-binding regions (NBD), and have a similar gene organization. In particular, this gene appears to be closely related to other ABCC subfamily members such as ABCC5, ABCC2 and ABCC3, particularly in the ATP-binding domain, and more particularly in the C-terminal ATP binding domains. The ABCC11 protein, as well as ABCC4 and ABCC5, is smaller than another well-known member of the subgroup, ABCC1 (MRP1), appearing to lack the extra N-terminal domain (Borst et al., *J Natl Cancer Inst*, 2000, 92, 1295–302), which is however not required for the transport function (Bakos et al., *J. Biol. Chem*, 1998, 273, 32167–75). Since structurally related ABC proteins often transport similar substrates across the membranes, it would be reasonable to suggest that the ABCC11 protein could share functional similarities with ABCC 4 and/or ABCC5 genes, i.e., the resistance to nucleotide analogs, such as PMEA, and purine base analogs (Schuetz et al., *Nat Med*, 1999 5, 1048–51; Wijnholds et al., *Proc Natl Acad Sci*, 2000, 97, 7476–81).

Furthermore, the applicants have mapped the novel gene ABCC11 in a region located in the 16q12 locus of the human chromosome 16, which is a region statistically linked with two genetic pathologies generally designated paroxysmal kinesigenic dyskinesia (PKD), i.e., paroxysmal kinesigenic choreoathetosis (PKC) (Tomita et al., *Am J Hum Genet*, 1999, 65, 1688–97; Bennett et al., *Neurology*, 2000, 54, 125–130) and infantile convulsions with paroxysmal choreoathetosis or the ICCA syndrome (Lee et al., 1998, *Human Genet*, 103, 608–612). These results support the hypothesis that ABCC11 represents a positional candidate on human chromosome 16 for paroxysmal disorders, such as paroxysmal kinesigenic choreoathetosis and/or infantile convulsions with paroxysmal choreoathetosis.

Paroxysmal kinesigenic choreoathetosis (PKC), the most frequent type of paroxysmal dyskinesia, is a disorder characterized by recurrent, frequent attacks of involuntary movements and postures, including chorea and dystonia, induced by sudden voluntary movements, stress, or excitement (Swoboda et al., *Neurology*, 2000, 55, 224–30). The onset is in childhood or early adolescence, the frequency and severity diminish with age, and it responds to treatment with anticonvulsants. PKC occurs in familial and sporadic forms and affects more males than females. In most families it is inherited as an autosomal dominant trait with incomplete penetrance. The gene locus has been mapped to human chromosome 16911–912 (Tomita et al. (1999) *Am. J Hum. Genet.* 65, 1588–1697; Bennett et al. (2000) *Neurology* 54, 125–130).

An overlapping locus has been predicted to contain the gene for infantile convulsions with paroxysmal choreoathetosis (ICCA) (Lee et al. (1998) *Hum. Genet.* 103, 608–612). The ICCA syndrome is a neurological syndrome linked to the pericentromeric region of human chromosome 16, characterized by involuntary-movements disorder and attacks that occur spontaneously or are induced by a variety of stimuli.

The Applicantss have further determined expression pattern of the ABCC11 gene by PCR and by EST database mining that suggests that the ABCC11 gene is expressed in tissues such as CNS and muscle which are potentially involved in the etiology of PKC.

SUMMARY OF THE INVENTION

The present invention relates to a nucleic acid of the human ABCC11 gene, which is likely to be involved in the transport of organic anion transporters, such as cysteinyl leukotriene, anionic drugs, such as methotrexate, as well as neutral drugs conjugated to acidic ligands, such as glutathione (GSH), glucuronate, or sulfate, or in the pathology whose candidate chromosomal region is situated on chromosome 16, more precisely on the 16q arm and still more precisely in the 16q 12 locus for paroxysmal kinesigenic choreoathetosis.

Thus, a first subject of the invention is a nucleic acid comprising a nucleotide sequence of any one of SEQ ID NOS:1–30, or a complementary nucleotide sequence thereof.

The invention also relates to a nucleic acid comprising at least 8 consecutive nucleotides of a nucleotide sequence of a) any one of SEQ ID NOS:1–30 or a complementary nucleotide sequence thereof.

The invention also relates to a nucleic acid having at least 80% nucleotide identity with a nucleic acid comprising a nucleotide sequence of any one of SEQ ID NOS:1–30, or a complementary nucleotide sequence thereof.

The invention also relates to a nucleic acid having at least 85%, 90%, 95%, or 98% nucleotide identity with a nucleic acid comprising a nucleotide sequence of any one of SEQ ID NOS:1–30, or a complementary nucleotide sequence thereof.

The invention also relates to a nucleic acid hybridizing, under high stringency conditions, with a nucleotide sequence of any one of SEQ ID NOS:1–30, or a complementary nucleotide sequence thereof.

The invention also relates to a nucleic acid, particularly a cDNA molecule, which encodes the full length human ABCC11 protein. Thus, the invention relates to a nucleic acid comprising a nucleotide sequence of SEQ ID NO:1, or a complementary nucleotide sequence thereof.

The invention also relates to a nucleic acid comprising a nucleotide sequence as depicted in SEQ ID NO:1, or a complementary nucleotide sequence thereof.

The invention also relates to, a nucleic acid comprising a nucleotide sequence of SEQ ID NO:1, which encodes a full length ABCC11 polypeptide of 1382 amino acids comprising the amino acid sequence of SEQ ID NO: 31.

Thus, the invention also relates to a nucleic acid encoding a polypeptide comprising an amino acid sequence of SEQ ID NO:31.

Thus, the invention also relates to a polypeptide comprising an amino acid sequence of SEQ ID NO:30.

The invention also relates to a polypeptide comprising an amino acid sequence as depicted in any one of SEQ ID NO:31.

The invention also relates to a means for detecting polymorphisms in general, and mutations in particular, in the ABCC11 gene or in the corresponding proteins produced by the allelic form of these genes.

According to another aspect, the invention also relates to the nucleotide sequences of ABCC11 gene comprising at least one biallelic polymorphism such as for example a substitution, addition or deletion of one or more nucleotides.

Nucleotide probes and primers hybridizing with a nucleic acid sequence located in the region of the ABCC11 nucleic acid (genomic DNA, messenger RNA, cDNA), in particular, a nucleic acid sequence comprising any one of the mutations or polymorphisms.

The nucleotide probes or primers according to the invention comprise at least 8 consecutive nucleotides of a nucleic acid comprising any one of SEQ ID NOS:1–30, or a complementary nucleotide sequence thereof.

Nucleotide probes or primers according to the invention may have a length of 10, 12, 15, 18 or 20 to 25, 35, 40, 50, 70, 80, 100, 200, 500, 1000, or 1500 consecutive nucleotides of a nucleic acid according to the invention, in particular of a nucleic acid comprising any one of SEQ ID NOS:1–30, or a complementary nucleotide sequence thereof.

Alternatively, a nucleotide probe or primer according to the invention will consist of and/or comprise fragments having a length of 12, 15, 18, 20, 25, 35, 40, 50, 100, 200, 500, 1000, or 1500 consecutive nucleotides of a nucleic acid according to the invention, more particularly of a nucleic acid comprising any one of SEQ ID NOS:1–30, or a complementary nucleotide sequence thereof.

The definition of a nucleotide probe or primer according to the invention covers oligonucleotides which hybridize, under the high stringency hybridization conditions defined below, with a nucleic acid comprising any one of SEQ ID NOS:1–30, or a complementary nucleotide thereof.

The nucleotide primers according to the invention may be used to amplify a nucleic acid according to the invention, and more particularly a nucleic acid comprising a nucleotide sequence of any one of SEQ ID NOS:1–30, or a complementary nucleotide sequence thereof.

Another subject of the invention relates to a method of amplifying a nucleic acid according to the invention, and more particularly a nucleic acid comprising any one of SEQ ID NOS:1–30, a complementary nucleotide sequence thereof, a nucleic acid as depicted in any one of SEQ ID NOS:1–30, or a complementary nucleotide sequence thereof, contained in a sample, said method comprising the steps of:

a) bringing the sample in which the presence of the target nucleic acid is suspected into contact with a pair of nucleotide primers whose hybridization position is located respectively on the 5' side and on the 3' side of the region of the target nucleic acid whose amplification is sought, in the presence of the reagents necessary for the amplification reaction;

b) amplifying the target nucleic acid; and c) detecting the amplified nucleic acids.

The present invention also relates to a method of detecting the presence of a nucleic acid comprising a nucleotide sequence of any one of SEQ ID NOS:1–30, or a complementary nucleotide sequence thereof, or a nucleic acid fragment or variant of any one of SEQ ID NOS:1–30, or a complementary nucleotide sequence thereof in a sample, said method comprising the steps of:

1) bringing one or more nucleotide probes according to the invention into contact with the sample to be tested;

2) detecting the complex which may have formed between the probe(s) and the nucleic acid present in the sample.

According to a specific embodiment of the method of detection according to the invention, the oligonucleotide probes are immobilized on a support.

According to another aspect, the oligonucleotide probes comprise a detectable marker.

Another subject of the invention is a box or kit for amplifying all or part of a nucleic acid comprising a) any one of SEQ ID NOS:1–30, or a complementary nucleotide sequence thereof, or b) as depicted in any one of SEQ ID NOS:1–30 or of a complementary nucleotide sequence thereof, said box or kit comprising:

1) a pair of nucleotide primers in accordance with the invention, whose hybridization position is located respectively on the 5' side and 3' side of a target nucleic acid whose amplification is sought; and optionally, 2) reagents necessary for an amplification reaction.

Such an amplification box or kit may comprise at least one pair of nucleotide primers as described above.

The invention also relates to a box or kit for detecting the presence of a nucleic acid according to the invention in a sample, said box or kit comprising:

a) one or more nucleotide probes according to the invention;

b) appropriate reagents necessary for a hybridisation reaction.

According to a first aspect, the detection box or kit is characterized in that the nucleotide probe(s) and primer(s) are immobilized on a support.

According to a second aspect, the detection box or kit is characterized in that the nucleotide probe(s) and primer(s) comprise a detectable marker.

According to a specific embodiment of the detection kit described above, such a kit will comprise a plurality of oligonucleotide probes and/or primers in accordance with the invention which may be used to detect target nucleic acids of interest or alternatively to detect mutations in the coding regions or the non-coding regions of the nucleic acids according to the invention. According to some embodiments of the invention, the target nucleic acid comprises a nucleotide sequence of any one of SEQ ID NOS:1–30, or of a complementary nucleic acid sequence. Alternatively, the target nucleic acid is a nucleic acid fragment or variant of a nucleic acid comprising any one of SEQ ID NOS:1–30, or of a complementary nucleotide sequence.

According to additional embodiments, a primer according to the invention comprises, generally, all or part of any one of SEQ ID NOS:1–30, or a complementary sequence thereof.

The invention also relates to a recombinant vector comprising a nucleic acid according to the invention. Such a recombinant vector may comprise:

a) a nucleic acid comprising a nucleotide sequence of any one of SEQ ID NOS:1–30, or a complementary nucleotide sequence thereof, b) a nucleic acid having at least eight consecutive nucleotides of a nucleic acid comprising a nucleotide sequence of any one of SEQ ID NOS:1–30, or a complementary nucleotide sequence thereof;

c) a nucleic acid having at least 80% nucleotide identity with a nucleic acid comprising a nucleotide sequence of any one of SEQ ID NOS:1–30, or a complementary nucleotide sequence thereof;

d) a nucleic acid having 85%, 90%, 95%, or 98% nucleotide identity with a nucleic acid comprising a nucleotide sequence of any one of SEQ ID NOS:1–30, or a complementary nucleotide sequence thereof;

e) a nucleic acid hybridizing, under high stringency hybridization conditions, with a nucleic acid comprising a nucleotide sequence of any one of SEQ ID NOS:1–30, or a complementary nucleotide sequence; or f) a nucleic acid encoding a polypeptide comprising an amino acid sequence of SEQ ID NO:31.

According to a first embodiment, a recombinant vector according to the invention is used to amplify a nucleic acid inserted therein, following transformation or transfection of a desired cellular host.

According to a second embodiment, a recombinant vector according to the invention corresponds to an expression vector comprising, in addition to a nucleic acid in accordance with the invention, a regulatory signal or nucleotide sequence that directs or controls transcription and/or translation of the nucleic acid and its encoded mRNA.

According to some embodiments, a recombinant vector according to the invention will comprise in particular the following components:

1) an element or signal for regulating the expression of the nucleic acid to be inserted, such as a promoter and/or enhancer sequence;

2) a nucleotide coding region comprised within the nucleic acid in accordance with the invention to be inserted into such a vector, said coding region being placed in phase with the regulatory element or signal described in (1); and 3) an appropriate nucleic acid for initiation and termination of transcription of the nucleotide coding region of the nucleic acid described in (2).

The present invention also relates to a defective recombinant virus comprising a cDNA nucleic acid encoding the ABCC11 polypeptide involved in the transport of various substances, or in the pathology whose candidate chromosomal region is situated on chromosome 16, more precisely on the 16q arm and still more precisely in the 16q12 locus for paroxysmal kinesigenic choreoathetosis.

In other embodiments of the invention, the defective recombinant virus comprises a gDNA nucleic acid encoding the ABCC11 polypeptide involved in paroxysmal kinesigenic choreoathetosis. The encoded ABCC11 polypeptide may comprise amino acid sequence of SEQ ID NO:31.

In further embodiments, the invention relates to a defective recombinant virus comprising a nucleic acid encoding the ABCC11 polypeptide under the control of an RSV-LTR or the CMV early promoter.

According to a specific embodiment, a method of introducing a nucleic acid according to the invention into a host cell in vivo, in particular a host cell obtained from a mammal, comprises a step wherein a preparation comprising a pharmaceutically compatible vector and a "naked" nucleic acid according to the invention, placed under the control of appropriate regulatory sequences, is introduced by local injection at the level of the chosen tissue, for example a smooth muscle tissue, the "naked" nucleic acid being absorbed by the cells of this tissue.

According to a specific embodiment of the invention, a composition is provided for the in vivo production of the ABCC11 protein. This composition comprises a nucleic acid encoding the ABCC11 polypeptide placed under the control of appropriate regulatory sequences, in solution in a physiologically acceptable vehicle and/or excipient.

Therefore, the present invention also relates to a composition comprising a nucleic acid encoding the ABCC11 polypeptide comprising an amino acid sequence of SEQ ID NO:30, wherein the nucleic acid is placed under the control of appropriate regulatory elements.

Consequently, the invention also relates to a pharmaceutical composition intended for the prevention of or treatment of a patient or subject affected by a paroxysmal kinesigenic choreoathetosis comprising a nucleic acid encoding the ABCC11 protein, in combination with one or more physiologically compatible excipients.

Such a composition may comprise a nucleic acid comprising a nucleotide sequence of any one of SEQ ID NOS:1–30, wherein the nucleic acid is placed under the control of an appropriate regulatory element or signal.

In addition, the present invention is directed to a pharmaceutical composition intended for the prevention or treatment of a patient or a subject affected by a a pathology located on the chromosome 16q12, such as the paroxysmal kinesigenic choreoathetosis, comprising a recombinant vector according to the invention, in combination with one or more physiologically compatible excipients.

The invention also relates to the use of a nucleic acid according to the invention encoding the ABCC11 protein for the manufacture of a medicament intended for the prevention of a pathology located on the chromosome locus 16q12, or more particularly for the treatment of subjects affected by a paroxysmal kinesigenic choreoathetosis The invention also relates to the use of a recombinant vector according to the invention comprising a nucleic acid encoding the ABCC11 protein for the manufacture of a medicament intended for the prevention of a pathology located on the chromosome locus 16q12 or more particularly for the treatment of subjects affected by a paroxysmal kinesigenic choreoathetosis.

The subject of the invention is therefore also a recombinant vector comprising a nucleic acid according to the invention that encodes the ABCC11 protein or polypeptide involved in the paroxysmal kinesigenic choreoathetosis.

The invention also relates to the use of such a recombinant vector for the preparation of a pharmaceutical composition intended for the treatment and/or for the prevention of diseases or conditions associated with deficiency of the ABCC11 gene and with a pathology located on the chromosome locus 16q12.

The present invention also relates to the use of cells genetically modified ex vivo with such a recombinant vector according to the invention, or cells producing a recombinant vector, wherein the cells are implanted in the body, to allow a prolonged and effective expression in vivo of any one biologically active ABCC11 polypeptide.

The invention also relates to the use of a nucleic acid according to the invention encoding the ABCC11 protein for the manufacture of a medicament intended for the prevention and/or the treatment of subjects affected by a paroxysmal kinesigenic choreoathetosis.

The invention also relates to the use of a recombinant vector according to the invention comprising a nucleic acid encoding the ABCC11 polypeptide according to the invention for the manufacture of a medicament intended for the prevention and/or the treatment of subjects affected by a a paroxysmal kinesigenic choreoathetosis.

The invention also relates to the use of a recombinant host cell according to the invention, comprising a nucleic acid encoding the ABCC11 polypeptide according to the invention for the manufacture of a medicament intended for the prevention and/or the treatment of subjects affected by a a paroxysmal kinesigenic choreoathetosis.

The present invention also relates to the use of a recombinant vector according to the invention, for example, a defective recombinant virus, for the preparation of a pharmaceutical composition for the treatment and/or prevention of pathologies linked to the dysfunction of the transport of anionic drugs, such as methotrexate (MTX), neutral drugs conjugated to acidic ligands, such as GSH, glucuronate, or sulfate conjugated drugs.

The invention relates to the use of such a recombinant vector or defective recombinant virus for the preparation of a pharmaceutical composition intended for the treatment and/or for the prevention of a pathology assciated with the chromosome locus 16912, such as PKC. Thus, the present invention also relates to a pharmaceutical composition comprising one or more recombinant vectors or defective recombinant viruses according to the invention.

The present invention also relates to the use of cells genetically modified ex vivo with a virus according to the invention, or the use of cells producing such viruses, implanted in the body, allowing a prolonged and effective expression in vivo a biologically active ABCC11 protein.

The present invention shows that it is possible to incorporate a nucleic acid encoding the ABCC11 polypeptide according to the invention into a viral vector, and that these vectors make it possible to effectively express a biologically active, mature polypeptide. More particularly, the invention shows that the in vivo expression of the ABCC11 protein may be obtained by direct administration of an adenovirus or by implantation of a producing cell or of a cell genetically modified by an adenovirus or by a retrovirus incorporating such a nucleic acid.

In this regard, another subject of the invention relates to any mammalian cell infected with one or more defective recombinant viruses according to the invention. More particularly, the invention relates to any population of human cells infected with these viruses. These may be in particular cells of blood origin (totipotent stem cells or precursors), fibroblasts, myoblasts, hepatocytes, keratinocytes, smooth muscle and endothelial cells, glial cells and the like.

Another subject of the invention relates to an implant comprising mammalian cells infected with one or more defective recombinant viruses according to the invention or cells producing recombinant viruses, and an extracellular matrix. The implants according to the invention may comprise $10^5$ to $10^{10}$ cells, or they may comprise $10^6$ to $10^8$ cells.

More particularly, in the implants of the invention, the extracellular matrix comprises a gelling compound and optionally, a support allowing for anchorage of the cells.

The invention also relates to a recombinant host cell comprising a nucleic acid of the invention, and more particularly, a nucleic acid comprising any one of SEQ ID NOS:1–30, or a complementary nucleotide sequence thereof.

The invention also relates to a recombinant host cell comprising a nucleic acid of the invention, and more particularly a nucleic acid comprising a nucleotide sequence as depicted in any one SEQ ID NOS:1–30, or a complementary nucleotide sequence thereof.

According to another aspect, the invention also relates to a recombinant host cell comprising a recombinant vector according to the invention. Therefore, the invention also relates to a recombinant host cell comprising a recombinant vector comprising any of the nucleic acids of the invention, and more particularly a nucleic acid comprising any one nucleotide sequence of SEQ ID NOS:1–30, or a complementary nucleotide sequence thereof.

Specifically, the invention relates to a recombinant host cell comprising a recombinant vector comprising a nucleic acid comprising any one of SEQ ID NOS:1–30, or a complementary nucleotide sequence thereof.

The invention also relates to a recombinant host cell comprising a recombinant vector comprising a nucleic acid comprising a nucleotide sequence as depicted in any one of SEQ ID NOS:1–30, or of a complementary nucleotide sequence thereof.

The invention also relates to a recombinant host cell comprising a recombinant vector comprising a nucleic acid encoding a polypeptide comprising an amino acid sequence of SEQ ID NO:31.

The invention also relates to a method for the production of a polypeptide comprising an amino acid sequence of SEQ ID NO:31, or of a peptide fragment or a variant thereof, said method comprising the steps of:

a) inserting a nucleic acid encoding said polypeptide into an appropriate vector;

b) culturing, in an appropriate culture medium, a previously transformed host cell or transfecting a host cell with the recombinant vector of step a);

c) recovering the conditioned culture medium or lysing the host cell, for example by sonication or by osmotic shock;

d) separating and purifying said polypeptide from said culture medium or alternatively from the cell lysates obtained in step c); and e) where appropriate, characterizing the recombinant polypeptide produced.

A polypeptide termed "homologous" to a polypeptide having an amino acid sequence of SEQ ID NO:31 also forms part of the invention. Such a homologous polypeptide comprises an amino acid sequence possessing one or more substitutions of an amino acid by an equivalent amino acid.

The ABCC11 polypeptide according to the invention, in particular 1) a polypeptide comprising an amino acid sequence of SEQ ID NO:31, 2) a polypeptide fragment or variant of a polypeptide comprising an amino acid sequence of SEQ ID NO:31, or 3) a polypeptide termed "homologous" to a polypeptide comprising amino acid sequence of SEQ ID NO:30.

In a specific embodiment, an antibody according to the invention is directed against 1) a polypeptide comprising an amino acid sequence of SEQ ID NO:31, 2) a polypeptide fragment or variant of a polypeptide comprising an amino acid sequence of SEQ ID NO:31, or 3) a polypeptide termed "homologous" to a polypeptide comprising amino acid sequence of SEQ ID NO:31. Such antibody is produced by using the trioma technique or the hybridoma technique described by Kozbor et al. (*Immunology Today* (1983) 4:72).

Thus, the subject of the invention is, in addition, a method of detecting the presence of any one of the polypeptides according to the invention in a sample, said method comprising the steps of:

a) bringing the sample to be tested into contact with an antibody directed against 1) a polypeptide comprising an amino acid sequence of SEQ ID NO:31, 2) a polypeptide fragment or variant of a polypeptide comprising an amino acid sequence of SEQ ID NO:31, 3) a polypeptide termed "homologous" to a polypeptide comprising amino acid sequence of SEQ ID NO:31, and b) detecting the antigen/antibody complex formed.

The invention also relates to a box or kit for diagnosis or for detecting the presence of any one of polypeptide in accordance with the invention in a sample, said box comprising:

a) an antibody directed against 1) a polypeptide comprising an amino acid sequence of SEQ ID NO:31, 2) a polypeptide fragment or variant of a polypeptide comprising an amino acid sequence of any one of SEQ ID NO:31, or 3) a polypeptide "homologous" to a polypeptide comprising amino acid sequence of SEQ ID NO:31, and b) a reagent allowing the detection of the antigen/antibody complexes formed.

The invention also relates to a pharmaceutical composition comprising a nucleic acid according to the invention.

The invention also provides pharmaceutical compositions comprising a nucleic acid encoding the ABCC11 polypeptide according to the invention and pharmaceutical compositions comprising the ABCC11 polypeptide according to the invention intended for the treatment of a pathology associated with the chromosome locus 16q12, such as the paroxysmal kinesigenic choreoathetosis.

The present invention also relates to a new therapeutic approach for the treatment of pathologies associated with the chromosome locus 16q12, such as the paroxysmal kinesigenic choreoathetosis, comprising transferring and expressing in vivo a nucleic acid encoding the ABCC11 protein according to the invention.

Thus, the present invention offers a new approach for the treatment and/or prevention of pathologies associated with chromosome locus 16q12, such as the paroxysmal kinesigenic choreoathetosis in a patient or subject. Specifically, the present invention provides methods to restore or promote the deficiency of the gene causing such pathology.

Consequently, the invention also relates to a pharmaceutical composition intended for the prevention and/or treatment of subjects affected by, a dysfunction of the gene located on the chromosome locus 16q12, such as paroxysmal kinesigenic choreoathetosis, comprising a nucleic acid encoding the ABCC11 protein, in combination with one or more physiologically compatible vehicle and/or excipient.

According to a specific embodiment of the invention, a composition is provided for the in vivo production of the ABCC11 protein. This composition comprises a nucleic acid encoding the ABCC11 polypeptide placed under the control of appropriate regulatory sequences, in solution in a physiologically compatible vehicle and/or excipient.

Therefore, the present invention also relates to a composition comprising a nucleic acid encoding a polypeptide comprising an amino acid sequence of SEQ ID NO:31, wherein the nucleic acid is placed under the control of appropriate regulatory elements.

Such a composition may comprise a nucleic acid comprising a nucleotide sequence of any one of SEQ ID NOS:1–30, placed under the control of appropriate regulatory elements.

The invention also relates to a pharmaceutical composition intended for the prevention of or treatment of subjects affected by a dysfunction of the transport of anionic drugs, such as methotrexate (MTX), neutral drugs conjugated to acidic ligands, such as GSH, glucuronate, or sulfate conjugated drugs, comprising a recombinant vector according to the invention, in combination with one or more physiologically compatible vehicle and/or excipient.

According to another aspect, the subject of the invention is also a preventive or curative therapeutic method of treating diseases caused by a deficiency of the transport of anionic drugs, such as methotrexate (MTX), neutral drugs conjugated to acidic ligands, such as GSH, glucuronate, or sulfate, such a method comprising administering to a patient a nucleic acid encoding the ABCC11 polypeptide according to the invention, said nucleic acid being combined with one or more physiologically appropriate vehicles and/or excipients.

The invention relates to a pharmaceutical composition for the prevention and/or treatment of a patient or subject affected by a dysfunction of the transport of anionic drugs, such as methotrexate (MTX), neutral drugs conjugated to acidic ligands, such as GSH, glucuronate, or sulfate comprising a therapeutically effective quantity of a polypeptide having an amino acid sequence of SEQ ID NO:31, combined with one or more physiologically appropriate vehicles and/or excipients.

The invention also relates to a pharmaceutical composition for the prevention and/or treatment of PKC comprising a therapeutically effective quantity of a polypeptide having an amino acid sequence of SEQ ID NO:31, combined with one or more physiologically appropriate vehicles and/or excipients.

The invention also relates to a pharmaceutical composition for the prevention and/or treatment of PKC, such a method comprising administering to a patient a nucleic acid encoding the ABCC11 polypeptide according to the invention, said nucleic acid being combined with one or more physiologically appropriate vehicles and/or excipients.

According to a specific embodiment, a method of introducing at least a nucleic acid according to the invention into a host cell, in particular a host cell obtained from a mammal, in vivo, comprises a step during which a preparation comprising a pharmaceutically compatible vector and a "naked" nucleic acid according to the invention, placed under the control of appropriate regulatory sequences, is introduced by local injection at the level of the chosen tissue, for example a smooth muscle tissue, the "naked" nucleic acid being absorbed by the cells of this tissue.

According to yet another aspect, the subject of the invention is also a preventive or curative therapeutic method of treating diseases caused by a deficiency of the transport of anionic drugs, such as methotrexate (MTX), neutral drugs conjugated to acidic ligands, such as GSH, glucuronate, or sulfate, such a method comprising administering to a patient a therapeutically effective quantity of the ABCC11 polypeptide according to the invention, said polypeptide being combined with one or more physiologically appropriate vehicles and/or excipients.

The invention also provides methods for screening small molecules and compounds that act on the ABCC11 protein to identify agonists and antagonists of such polypeptides that can restore or promote improved the transport of anionic drugs, such as methotrexate (MTX), neutral drugs conjugated to acidic ligands, such as GSH, glucuronate, or sulfate to effectively cure and or prevent dysfunctions thereof. These methods are useful to identify small molecules and compounds for therapeutic use in the treatment of diseases due to a deficiency of the transport of anionic drugs, such as methotrexate (MTX), neutral drugs conjugated to acidic ligands, such as GSH conjugated drugs, glucuronate, or sulfate.

Therefore, the invention also relates to the use of the ABCC11 polypeptide or a cell expressing the ABCC11 polypeptide according to the invention, for screening active ingredients for the prevention and/or treatment of diseases resulting from a dysfunction of the transport of anionic drugs, such as methotrexate (MTX), neutral drugs conjugated to acidic ligands, such as GSH conjugated drugs, glucuronate, or sulfate.

The invention also relates to a method of screening a compound or small molecule, an agonist or antagonist of the ABCC11 polypeptide, said method comprising the following steps:

a) preparing a membrane vesicle comprising the ABCC11 polypeptide and a lipid substrate comprising a detectable marker;

b) incubating the vesicle obtained in step a) with an agonist or antagonist candidate compound;

c) qualitatively and/or quantitatively measuring release of the lipid substrate comprising a detectable marker; and d) comparing the release measurement obtained in step b) with a measurement of release of a labelled lipid substrate by a vesicle that has not been previously incubated with the agonist or antagonist candidate compound.

In a first specific embodiment, the ABCC11 polypeptide comprises SEQ ID NO:31, respectively.

The invention also relates to a method of screening a compound or small molecule, an agonist or antagonist of the ABCC11 polypeptide, said method comprising the following steps:

a) obtaining a cell, for example a cell line, that, either naturally or after transfecting the cell with the ABCC11 encoding nucleic acid, expressing the corresponding ABCC11 polypeptide;

b) incubating the cell of step a) in the presence of an anion labelled with a detectable marker;

c) washing the cell of step b) in order to remove the excess of the labelled anion which has not penetrated into these cells;

d) incubating the cell obtained in step c) with an agonist or antagonist candidate compound for the the ABCC11 polypeptide;

e) measuring efflux of the labelled anion; and f) comparing the value of efflux of the labelled anion determined in step e) with a value of efflux of a labelled anion measured with cell which has not been previously incubated in the presence of the agonist or antagonist candidate compound for the ABCC11 polypeptide.

In a specific embodiment, the ABCC11 polypeptide comprises SEQ ID NO:30.

BRIEF DESCRIPTION OF THE DRAWINGS

FIG. 1 represents the alignment of ABCC11, ABCC12, and ABCC5 proteins. Identical amino acids are shaded, gaps are indicated by periods. Walker A and B motifs and the ABC transporter family signature sequence C are underlined and labelled with respective letters. Amino acid sequences were aligned with the PILEUP program in the Genetics Computer Group Package. Potential transmembrane spanning segments are given in bold type.

DETAILED DESCRIPTION OF THE EMBODIMENTS

General Definitions

Figure 2:
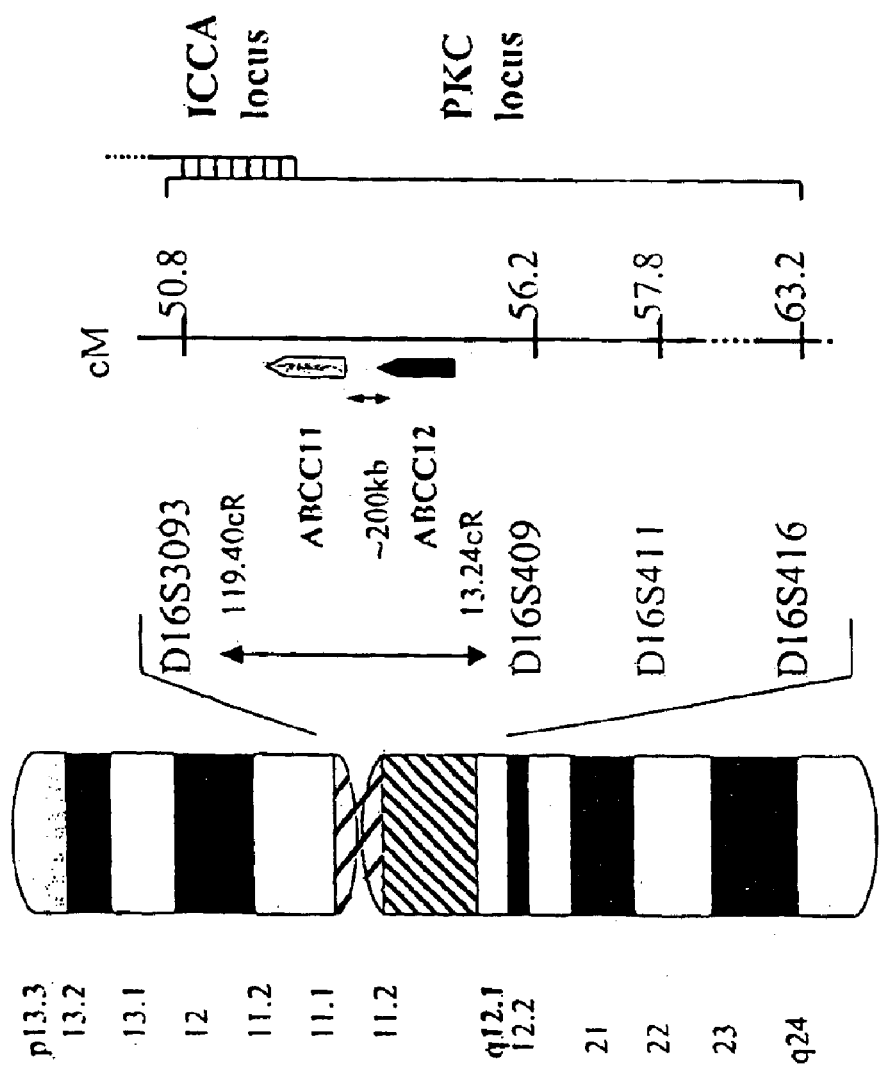
FIG. 2 represents the physical map of the chromosome 16 and localization of the human ABCC11 and ABCC12 genes. Human ABCC11 and ABCC12 genes, flanked by markers D1653093 and D165409, are separated by about 200 kb, and organized in a head-to-tail fashion, with their 5' end facing the centromere. Loci for ICCA, PKC, and their overlap, are defined by brackets. ABCC11 and ABCC12 genes are indicated by gray and black arrows, respectively.

The present invention contemplates isolation of a human gene encoding ABCC11 polypeptide of the invention, including a full length, or naturally occurring form of ABCC11 and any antigenic fragments thereof from any animal, particularly mammalian or avian, and more particularly human source.

In accordance with the present invention, conventional molecular biology, microbiology, and recombinant DNA techniques within the skill of the art are used. Such techniques are fully explained in the literature (Sambrook et al., 1989. Molecular cloning a laboratory manual. 2ed. Cold Spring Harbor Laboratory, Cold Spring Harbor, N.Y.; Glover, 1985, DNA Cloning: A pratical approach, volumes I and II oligonucleotide synthesis, MRL Press, LTD., Oxford, U.K.; Hames and Higgins, 1985, Transcription and translation; Hames and Higgins, 1984, Animal Cell Culture; Freshney, 1986, Immobilized Cells And Enzymes, IRL Press; and Perbal, 1984, A practical guide to molecular cloning).

As used herein, the term "gene" refers to an assembly of nucleotides that encode a polypeptide, and includes cDNA and genomic DNA.

The term "isolated" for the purposes of the present invention designates a biological material (nucleic acid or protein) which has been removed from its original environment, that is, the environment in which it is naturally present.

For example, a polynucleotide present in the natural state in a plant or an animal is not isolated. The same nucleotide separated from the adjacent nucleic acids in which it is naturally inserted in the genome of the plant or animal is considered as being "isolated."

Such a polynucleotide may be included in a vector and/or such a polynucleotide may be included in a composition and remains nevertheless in the isolated state because of the fact that the vector or the composition does not constitute its natural environment.

The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, such as 2 or 3 orders of magnitude, or, for example, 4 or 5 orders of magnitude.

For the purposes of the present description, the expression "nucleotide sequence" may be used to designate either a polynucleotide or a nucleic acid. The expression "nucleotide sequence" covers the genetic material itself and is therefore not restricted to the information relating to its sequence.

The terms "nucleic acid," "polynucleotide," "oligonucleotide," or "nucleotide sequence" cover RNA, DNA, or cDNA sequences or alternatively RNA/DNA hybrid sequences of more than one nucleotide, either in the single-stranded form or in the duplex, double-stranded form.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence or coding sequence.

The term "nucleotide" designates both the natural nucleotides (A, T, G, C) as well as the modified nucleotides that comprise at least one modification such as (1) an analog of a purine, (2) an analog of a pyrimidine, or (3) an analogous sugar, examples of such modified nucleotides being described, for example, in the PCT application No. WO 95/04 064.

For the purposes of the present invention, a first polynucleotide is considered as being "complementary" to a second polynucleotide when each base of the first nucleotide is paired with the complementary base of the second polynucleotide whose orientation is reversed. The complementary bases are A and T (or A and U), or C and G.

"Heterologous" DNA refers to DNA not naturally located in the cell, or in a chromosomal site of the cell. The heterologous DNA may include a gene foreign to the cell.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50 :667)). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (for example, at least about 75%, or at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; Glover et al. (1985. DNA Cloning: A practical approach, volumes I and II oligonucleatide synthesis, MRL Press, Ltd, Oxford, U.K.); Hames and Higgins (1985. Transcription and Translation).

Similarly, in a particular embodiment, two amino acid sequences are "substantially homologous" or "substantially similar" when greater than 30% of the amino acids are identical, or greater than about 60% are similar (functionally identical). The similar or homologous sequences may be identified by alignment using, for example, the GCG (Genetics Computer Group, Program Manual for the GCG Package, Version 7, Madison, Wis.) pileup program.

The "percentage identity" between two nucleotide or amino acid sequences, for the purposes of the present invention, may be determined by comparing two sequences aligned optimally, through a window for comparison.

The portion of the nucleotide or polypeptide sequence in the window for comparison may thus comprise additions or deletions (for example "gaps") relative to the reference sequence (which does not comprise these additions or these deletions) so as to obtain an optimum alignment of the two sequences.

The percentage is calculated by determining the number of positions at which an identical nucleic base or an identical amino acid residue is observed for the two sequences (nucleic or peptide) compared, and then by dividing the number of positions at which there is identity between the two bases or amino acid residues by the total number of positions in the window for comparison, and then multiplying the result by 100 in order to obtain the percentage sequence identity.

The optimum sequence alignment for the comparison may be achieved using a computer with the aid of known algorithms contained in the package from the company WISCONSIN GENETICS SOFTWARE PACKAGE, GENETICS COMPUTER GROUP (GCG), 575 Science Doctor, Madison, Wis.

By way of illustration, it will be possible to produce the percentage sequence identity with the aid of the BLAST software (versions BLAST 1.4.9 of March 1996, BLAST 2.0.4 of February 1998 and BLAST 2.0.6 of September 1998), using exclusively the default parameters (Altschul et al, 1990,. Mol. Biol., 215:403–410; Altschul et al, 1997, Nucleic Acids Res., 25:3389–3402). Blast searches for sequences similar/homologous to a reference "request" sequence, with the aid of the Altschul et al. algorithm. The request sequence and the databases used may be of the peptide or nucleic types, any combination being possible.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A gene encoding the ABCC11 polypeptide of the invention, whether genomic DNA or cDNA, can be isolated from any source, particularly from a human cDNA or genomic library. Methods for obtaining genes are well known in the art, as described above (see, e.g., Sambrook et al., 1989, Molecular cloning: a laboratory manual. 2ed. Cold Spring Harbor Laboratory, Cold Spring Harbor, N.Y.).

Accordingly, any animal cell potentially can serve as the nucleic acid source for the molecular cloning of the ABCC11 gene. The DNA may be obtained by standard procedures known in the art from cloned DNA (e.g., a DNA "library"), and may be obtained from a cDNA library prepared from tissues with high level expression of the protein and/or the transcripts, by chemical synthesis, by cDNA cloning, or by the cloning of genomic DNA, or fragments thereof, purified from the desired cell (See, for example, Sambrook et al., 1989, Molecular cloning: a laboratory manual. 2ed. Cold Spring Harbor Laboratory, Cold Spring Harbor, N.Y.; Glover, 1985, DNA Cloning: A Practical Approach, Volumes I and II Oligonucleotide Synthesis, MRL Press, Ltd., Oxford, U.K).

Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired ABCC11 gene may be accomplished in a number of ways. For example, if an amount of a portion of the ABCC11 gene or its specific RNA, or a fragment thereof, is available and can be purified and labelled, the generated DNA fragments may be screened by nucleic acid hybridization to the labelled probe (Benton and Davis, Science (1977), 196:180; Grunstein et al., Proc. Natl. Acad. Sci. U.S.A. (1975) 72:3961). For example, a set of oligonucleotides corresponding to the partial coding sequence information obtained for the ABCC11 protein can be prepared and used as probes for DNA encoding the ABCC11, as was done in a specific example, infra, or as primers for cDNA or mRNA (e.g., in combination with a poly-T primer for RT-PCR). A fragment may be selected that is highly unique to the ABCC11 nucleic acid or polypeptide of the invention. Those DNA fragments with substantial homology to the probe will hybridize. As noted above, the greater the degree of homology, the more stringent hybridization conditions can be used. In a specific embodiment, various stringency hybridization conditions are used to identify homologous ABCC11 gene.

Further selection can be carried out on the basis of the properties of the gene, e.g., if the gene encodes a protein product having the isoelectric, electrophoretic, amino acid composition, or partial amino acid sequence of the ABCC11 protein as disclosed herein. Thus, the presence of the gene may be detected by assays based on the physical, chemical, or immunological properties of its expressed product. For example, cDNA clones, or DNA clones which hybrid-select the proper mRNAs, can be selected that produce a protein having, for example, similar or identical electrophoretic migration, isoelectric focusing or non-equilibrium pH gel electrophoresis behaviour, proteolytic digestion maps, or antigenic properties as known for ABCC11.

The ABCC11 gene of the invention may also be identified by mRNA selection, i.e., by nucleic acid hybridization followed by in vitro translation. According to this procedure, nucleotide fragments are used to isolate complementary mRNAs by hybridization. Such DNA fragments may represent available, purified ABCC11 DNA, or may be synthetic oligonucleotides designed from the partial coding sequence information. Immunoprecipitation analysis or functional assays (e.g., tyrosine phosphatase activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against the ABCC11 polypeptide of the invention.

A radiolabeled ABCC11 cDNA can be synthesized using the selected mRNA (from the adsorbed polysomes) as a template. The radiolabeled mRNA or cDNA may then be used as a probe to identify homologous ABCC11 DNA fragments from among other genomic DNA fragments.

"Variant" of a nucleic acid according to the invention will be understood to mean a nucleic acid which differs by one or more bases relative to the reference polynucleotide. A variant nucleic acid may be of natural origin, such as an allelic variant which exists naturally, or it may also be a normatural variant obtained, for example, by mutagenic techniques.

In general, the differences between the reference (generally, wild-type) nucleic acid and the variant nucleic acid are small such that the nucleotide sequences of the reference nucleic acid and of the variant nucleic acid are very similar and, in many regions, identical. The nucleotide modifications present in a variant nucleic acid may be silent, which means that they do not alter the amino acid sequences encoded by said variant nucleic acid.

However, the changes in nucleotides in a variant nucleic acid may also result in substitutions, additions or deletions in the polypeptide encoded by the variant nucleic acid in relation to the polypeptides encoded by the reference nucleic acid. In addition, nucleotide modifications in the coding regions may produce conservative or non-conservative substitutions in the amino acid sequence of the polypeptide.

The variant nucleic acids according to the invention may encode polypeptides which substantially conserve the same function or biological activity as the polypeptide of the reference nucleic acid or alternatively the capacity to be recognized by antibodies directed against the polypeptides encoded by the initial reference nucleic acid.

Some variant nucleic acids will thus encode mutated forms of the polypeptides whose systematic study will make it possible to deduce structure-activity relationships of the proteins in question. Knowledge of these variants in relation to the disease studied is essential since it makes it possible to understand the molecular cause of the pathology.

"Fragment" will be understood to mean a nucleotide sequence of reduced length relative to the reference nucleic acid and comprising, over the common portion, a nucleotide sequence identical to the reference nucleic acid. Such a nucleic acid "fragment" according to the invention may be, where appropriate, included in a larger polynucleotide of which it is a constituent. Such fragments comprise, or alternatively consist of oligonucleotides ranging in length from 8, 10, 12, 15, 18, 20 to 25, 30, 40, 50, 70, 80, 100, 200, 500, 1000 or 1500 consecutive nucleotides of a nucleic acid according to the invention.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SCC. High stringency hybridization conditions correspond to the highest $T_m$, e.g., 50% form amide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra). For hybridization with shorter nucleic acids, i.e., oligonucleotides, the position of mismatches becomes more important, and the length of the oligonucleotide determines its specificity (see Sambrook et al., supra). A minimum length for a hybridizable nucleic acid may be at least about 10 nucleotides; or may be at least about 15 nucleotides; or at least about 20 nucleotides.

In a specific embodiment, the term "standard hybridization conditions" refers to a $T_m$ of 55° C., and utilizes conditions as set forth above. In some embodiments, the $T_m$ is 60° C.; in another embodiment, the $T_m$ is 65° C.

"High stringency hybridization conditions" for the purposes of the present invention will be understood to mean the following conditions:

1—Membrane Competition and PREHYBRIDIZATION:
 Mix: 40 µl salmon sperm DNA (10 mg/ml)+40 µl human placental DNA (10 mg/ml)
 Denature for 5 minutes at 96° C., then immerse the mixture in ice.
 Remove the 2×SSC and pour 4 ml of formamide mix in the hybridization tube containing the membranes.
 Add the mixture of the two denatured DNAs.
 Incubation at 42° C. for 5 to 6 hours, with rotation.

2—Labeled Probe Competition:
 Add to the labeled and purified probe 10 to 50 µl Cot I DNA, depending on the quantity of repeats.
 Denature for 7 to 10 minutes at 95° C.
 Incubate at 65° C. for 2 to 5 hours.

3—HYBRIDIZATION:
 Remove the prehybridization mix.
 Mix 40 µl salmon sperm DNA+40 µl human placental DNA; denature for 5 min at 96° C., then immerse in ice.
 Add to the hybridization tube 4 ml of formamide mix, the mixture of the two DNAs and the denatured labeled probe/Cot I DNA.
 Incubate 15 to 20 hours at 42° C., with rotation.

4—Washes and Exposure:
 One wash at room temperature in 2×SSC, to rinse.
 Twice 5 minutes at room temperature 2×SSC and 0.1% SDS at 65° C.
 Twice 15 minutes 0.1×SSC and 0.1% SDS at 65° C.
 Envelope the membranes in clear plastic wrap and expose.

The hybridization conditions described above are adapted to hybridization, under high stringency conditions, of a molecule of nucleic acid of varying length from 20 nucleotides to several hundreds of nucleotides. It goes without saying that the hybridization conditions described above may be adjusted as a function of the length of the nucleic acid whose hybridization is sought or of the type of labeling chosen, according to techniques known to one skilled in the art. Suitable hybridization conditions may, for example, be adjusted according to the teaching contained in the manual by Hames and Higgins (1985, supra).

As used herein, the term "oligonucleotide" refers to a nucleic acid, generally of at least 15 nucleotides, that is hybridizable to a nucleic acid according to the invention. Oligonucleotides can be labelled, e.g., with $^{32}P$-nucleotides or nucleotides to which a label, such as biotin, has been covalently conjugated. In one embodiment, a labeled oligonucleotide can be used as a probe to detect the presence of a nucleic acid encoding the ABCC11 polypeptide of the invention. In another embodiment, oligonucleotides (one or both of which may be labelled) can be used as PCR primers, either for cloning full lengths or fragments of of the ABCC11 nucleic acid, or to detect the presence of a nucleic acid encoding the ABCC11 protein. In a further embodiment, an oligonucleotide of the invention can form a triple helix with the ABCC11 DNA molecule. Generally, oligonucleotides are prepared synthetically, such as on a nucleic acid synthesizer. Accordingly, oligonucleotides can be prepared with non-naturally occurring phosphoester analog bonds, such as thioester bonds, etc.

"Homologous recombination" refers to the insertion of a foreign DNA sequence of a vector in a chromosome. The vector may target a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

"Regulatory region" means a nucleic acid sequence which regulates the expression of a nucleic acid. A regulatory region may include sequences which are naturally responsible for expressing a particular nucleic acid (a homologous region) or may include sequences of a different origin (responsible for expressing different proteins or even synthetic proteins). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

A "polypeptide" is a polymeric compound comprised of covalently linked amino acid residues. Amino acids have the following general structure:

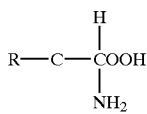

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

A "protein" is a polypeptide which plays a structural or functional role in a living cell.

The polypeptides and proteins of the invention may be glycosylated or unglycosylated.

"Homology" means similarity of sequence reflecting a common evolutionary origin. Polypeptides or proteins are said to have homology, or similarity, if a substantial number of their amino acids are either (1) identical, or (2) have a chemically similar R side chain. Nucleic acids are said to have homology if a substantial number of their nucleotides are identical.

"Isolated polypeptide" or "isolated protein" is a polypeptide or protein which is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of 5, 10, 15, 20, 30 to 40, 50, 100, 200 or 300 amino acids.

"Variant" of a polypeptide according to the invention will be understood to mean mainly a polypeptide whose amino acid sequence contains one or more substitutions, additions or deletions of at least one amino acid residue, relative to the amino acid sequence of the reference polypeptide, it being understood that the amino acid substitutions may be either conservative or nonconservative.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. Variants also include a related protein having substantially the same biological activity, but obtained from a different species.

The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art.

If such allelic variations, analogues, fragments, derivatives, mutants, and modifications, including alternative mRNA splicing forms and alternative post-translational modification forms result in derivatives of the polypeptide which retain any of the biological properties of the polypeptide, they are intended to be included within the scope of this invention.

A "vector" is a replicon, such as plasmid, virus, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

The present invention also relates to cloning vectors containing a gene encoding analogs and derivatives of the ABCC11 polypeptide of the invention. The production and use of derivatives and analogs related to the ABCC11 protein are within the scope of the present invention. In a specific embodiment, the derivatives or analogs are functionally active, i.e., capable of exhibiting one or more functional activities associated with a full-length, wild-type ABCC11 polypeptide of the invention.

ABCC11 derivatives can be made by altering encoding nucleic acid sequences by substitutions, additions or deletions that provide for functionally equivalent molecules. Derivatives may be made that have enhanced or increased functional activity relative to native ABCC11. Alternatively, such derivatives may encode soluble fragments of the ABCC11 extracellular domains that have the same or greater affinity for the natural ligand of ABCC11 polypeptide of the invention. Such soluble derivatives may be potent inhibitors of ligand binding to ABCC11.

Due to the degeneracy of nucleotide coding sequences, other DNA sequences which encode substantially same amino acid sequences as that of ABCC11 gene may be used in the practice of the present invention. These include but are not limited to allelic genes, homologous genes from other species, and nucleotide sequences comprising all or portions of ABCC11 gene which are altered by the substitution of different codons that encode the same amino acid residue within the sequence, thus producing a silent change. Likewise, the ABCC11 derivatives of the invention include, but are not limited to, those containing, as a primary amino acid sequence, all or part of the amino acid sequence of the ABCC11 protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence maybe selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, senne, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Example substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $CONH_2$ can be maintained.

Amino acid substitutions may also be introduced to substitute an amino acid with a particular property. For example, a Cys may be introduced as a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces b-turns in the protein's structure.

The genes encoding ABCC11 derivatives and analogs of the invention can be produced by various methods known in the art. The manipulations which result in their production can occur at the gene or protein level. For example, the cloned ABCC11 sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. Production of a gene encoding a derivative or analog of any one of the ABCC11 and ABCC12, should ensure that the modified gene remains within the same translational reading frame as the ABCC11 gene, uninterrupted by translational stop signals, in the region where the desired activity is encoded.

Additionally, the ABCC11-encoding nucleic acid can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Such mutations may enhance the functional activity of the mutated ABCC11 gene products. Any technique for mutagenesis known in the art may be used, including inter alia, in vitro site-directed mutagenesis (Hutchinson et al., (1978) Biol. Chem. 253:6551; Zoller and Smith, (1984) DNA, 3:479–488; Oliphant et al., (1986) *Gene* 44:177; Hutchinson et al., (1986) *Proc. Natl. Acad. Sci. U.S.A.* 83:710; Huygen et al., (1996) Nature Medicine, 2(8):893–898) and use of TAB® linkers (Pharmacia). PCR techniques may be used for site-directed mutagenesis (Higuchi, 1989, "Using PCR to Engineer DNA", in *PCR Technology: Principles and Applications for DNA Amplification*, H. Erlich, ed., Stockton Press, Chapter 6, pp. 61–70).

Identified and isolated ABCC11 gene may then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *Escherichia coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. The cloned gene may be contained on a shuttle vector plasmid, which provides for expansion in a cloning cell, e.g., *Escherichia coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2 m plasmid.

In an alternative method, the desired gene may be identified and isolated after insertion into a suitable cloning vector in a "shot gun" approach. Enrichment for the desired gene, for example, by size fractionation, can be done before insertion into the cloning vector.

The nucleotide sequence coding for the ABCC11 polypeptide or antigenic fragments, derivatives or analogs thereof, or functionally active derivatives, including chimeric proteins thereof, may be inserted into an appropriate expression vector, i.e., a vector which contains the necessary elements for the transcription and translation of the inserted protein-coding sequence. Such elements are termed herein a "promoter." Thus, nucleic acid encoding the ABCC11 polypeptide of the invention are operationally associated with a promoter in an expression vector of the invention. Both cDNA and genomic sequences can be cloned and expressed under control of such regulatory sequences. An expression vector may also include a replication origin.

The necessary transcriptional and translational signals can be provided on a recombinant expression vector, or they may be supplied by a native gene encoding ABCC11 and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant ABCC11 protein of the invention, or functional fragments, derivatives, chimeric constructs, or analogs thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding the ABCC11 polypeptide according to the invention is cultured in an appropriate cell culture medium under conditions that provide for expression of the ABCC11 polypeptide by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of ABCC11 polypeptide maybe controlled by any promoter/enhancer element known in the art, but these regulatory elements must be functional in the host selected for expression. Promoters which may be used to control ABCC11 gene expression include, but are not limited to, the SV40 early promoter region (Benoist and Chambon, 1981 Nature 290:304–310), the promoter contained in the 3' long terminal repeat of Rous sarcoma virus (Yamamoto, et al., 1980 Cell 22:787–797), the herpes thymidine kinase promoter (Wagner et al., 1981 Proc. Natl. Acad. Sci. U.S.A. 78:1441–1445), the regulatory sequences of the metallothionein gene (Brinster et al., 1982 Nature 296:39–42); prokaryotic expression vectors such as the β-lactamase promoter (Villa-Kamaroff, et al., 1978 Proc. Natl. Acad. Sci. U.S.A. 75:3727–3731), or the tac promoter (DeBoer, et al., 1983 Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984 Cell 38:639–646; Ornitz et al., 1986 Cold Spring Harbor Symp. Quant. Biol. 50:399–409; MacDonald, 1987); insulin gene control region which is active in pancreatic beta cells (Hanahan, 1985 Nature: 315:115–122), immunoglobulin gene control region which is active in lymphoid cells (Grosschedl et al., 1984 Cell 38:647–658; Adames et al., 1985 Nature 318:533–538; Alexander et al., 1987 Mol. Cell. Biol. 7:1436–1444), mouse mammary tumor virus control region which is active in testicular, breast, lymphoid and mast cells (Leder et al., 1986 Cell 45:485–495), albumin gene control region which is active in liver (Pinkert et al., 1987 Genes and Devel. 1:268–276), alpha-fetoprotein gene control region which is active in liver (Krumlauf et al., 1985 Mol. Cell. Biol. 5:1639–1648; Hammer et al., 1987 Science 235:53–58), alpha 1-antitrypsin gene control region which is active in the liver (Kelsey et al., 1987 Genes and Devel. 1:161–171) beta-globin gene control region which is active in myeloid cells (Mogram et al., 1985 Nature 315:338–340; Kollias et al., 1986 Cell 46:89–94), myelin basic protein gene control region which is active in oligodendrocyte cells in the brain (Readhead et al., 1987 Cell 48:703–712), myosin light chain-2 gene control region which is active in skeletal muscle (Sani, 1985 Nature 314:283–286), and gonadotropic releasing hormone gene control region which is active in the hypothalamus (Mason et al., 1986 Science 234:1372–1378).

Expression vectors containing a nucleic acid encoding the ABCC11 polypeptide of the invention can be identified by five general approaches: (a) polymerase chain reaction (PCR) amplification of the desired plasmid DNA or specific mRNA, (b) nucleic acid hybridization, (c) presence or absence of selection marker gene functions, (d) analyses with appropriate restriction endonucleases, and (e) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., b-galactosidase activity, thymidine kinase activity, resistance to antibiotics, transformation phenotype, occlusion body formation in baculovirus, etc.) caused by the insertion of foreign genes in the vector. In another example, if the nucleic acid encoding the ABCC11 polypeptide is inserted within the "selection marker" gene sequence of the vector, recombinants containing the ABCC11 nucleic acid can be identified by the absence of the ABCC11 gene functions. In the fourth approach, recombinant expression vectors are identified by digestion with appropriate restriction enzymes. In the fifth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the nucleic acids of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMa1-C2, pET, pGEX (Smith et al., 1988, Gene 67:31–40), pMB9 and their derivatives, plasmids such as RP4; phage DNAs, e.g. the numerous derivatives of phage 1, e.g., NM989, and other phage DNA, e.g., M13 and filamentous single stranded phage DNA; yeast plasmids such as the 2 m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, Bg/II, and PstI cloning site; Invitrogen), pVL1392 (Bg/II, PstI, NotI, XmaIII, EcoR1, XbaI, SmaI, and BamH1 cloning site; Summers and Invitrogen), and pBlueBacIII (BamH1, Bg/II, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, Bg/II, PstI, NcoI, and HindIII cloning site, an N-terminal peptide for ProBond purification, and blue/white recombinant screening of plaques; Invitrogen (220) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; See, Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and b-gal selection), pMJ601 (SalI, SmaI, AflI, NarI, BspMII, BamHI, ApaI, NheI, SacII, KpnI, and HindIII cloning site; TK- and b-gal selection), and pTKgptF1S (EcoRI, PstI, SalI, AccI, HindII, SbaI, BamHI, and Hpa cloning site, TK or XPRT selection).

Yeast expression systems can also be used according to the invention to express the ABCC11 polypeptide. For example, the non-fusion pYES2 vector (XbaI, SphI, ShoI, NotI, GstXI, EcoRI, BstXI, BamH1, SacI, KpnI, and HindIII cloning sit; Invitrogen) or the fusion pYESHisA, B, C (XbaI, SphI, ShoI, NotI, BstXI, EcoRI, BamHII, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage for example of the signal sequence) of proteins. Appropriate cell lines or host systems can be chosen to ensure the desired modification and processing of the foreign protein expressed. For example, expression in a bacterial system can be used to produce an nonglycosylated core protein product. However, the transmembrane ABCC11 protein expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, ABCC11 activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

A cell has been "transfected" by exogenous or heterologous DNA when such DNA has been introduced inside the cell. A cell has been "transformed" by exogenous or heterologous DNA when the transfected DNA effects a phenotypic change. The transforming DNA may be integrated (covalently linked) into chromosomal DNA making up the genome of the cell.

A recombinant marker protein expressed as an integral membrane protein can be isolated and purified by standard methods. Generally, the integral membrane protein can be obtained by lysing the membrane with detergents, such as but not limited to, sodium dodecyl sulfate (SDS), Triton X-100 polyoxyethylene ester, Ipagel/nonidet P-40 (NP-40) (octylphenoxy)-polyethoxyethanol, digoxin, sodium deoxycholate, and the like, including mixtures thereof. Solubilization can be enhanced by sonication of the suspension. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Alternatively, a nucleic acid or vector according to the invention can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner, et. al. (1987. PNAS 84/7413); Mackey, et al. (1988, *Proc. Natl. Acad. Sci. USA*, 85 :8027–8031); Ulmer et al. (1993, *Science*, 259 :1745–1748). The use of cationic lipids may promote encapsulation of negatively charged nucleic acids, and also promote fusion with negatively charged cell membranes (Felgner et al., 1989, *Science*, 337:387–388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly useful in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector in vivo as a naked DNA plasmid (see U.S. Pat. Nos. 5,693,622, 5,589,466 and 5,580,859). Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, Wu et al., 1992, supra; Wu and Wu, 1988, supra; Hartmut et al., Canadian Patent Application No. 2,012,311, filed Mar. 15, 1990; Williams et al., 1991, *Proc. Natl. Acad. Sci. USA* 88:2726–2730).

Receptor-mediated DNA delivery approaches can also be used (Curiel et al., 1992, Hum. Gene Ther. 3:147–154; Wu and Wu, 1987, J. Biol. Chem. 262:4429–4432).

"Pharmaceutically acceptable vehicle or excipient" includes diluents and fillers which are pharmaceutically acceptable for method of administration, are sterile, and may be aqueous or oleaginous suspensions formulated using suitable dispersing or wetting agents and suspending agents. The particular pharmaceutically acceptable carrier and the ratio of active compound to carrier are determined by the solubility and chemical properties of the composition, the particular mode of administration, and standard pharmaceutical practice.

Any nucleic acid, polypeptide, vector, or host cell of the invention may be introduced in vivo in a pharmaceutically acceptable vehicle or excipient. The phrase "pharmaceutically acceptable" refers to molecular entities and compositions that are physiologically tolerable and do not typically produce an allergic or similar untoward reaction, such as gastric upset, dizziness and the like, when administered to a human. As used herein, the term "pharmaceutically acceptable" generally means approved by a regulatory agency of the Federal or a state government or listed in the U.S. Pharmacopeia or other generally recognized pharmacopeia for use in animals, and more particularly in humans. The term "excipient" refers to a diluent, adjuvant, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions may be employed as excipients, particularly for injectable solutions. Suitable pharmaceutical excipients are described in "Remington's Pharmaceutical Sciences" by E. W. Martin.

Naturally, the invention contemplates delivery of a vector that will express a therapeutically effective amount of the ABCC11 polypeptide for gene therapy applications. The phrase "therapeutically effective amount" is used herein to mean an amount sufficient to reduce by at least about 15 percent, or, for example, by at least 50 percent, or by at least 90 percent, or prevent, a clinically significant deficit in the activity, function and response of the host. Alternatively, a therapeutically effective amount is sufficient to cause an improvement in a clinically significant condition in the host.

Nucleic Acids of the ABCC11 Gene

The applicants have identified a novel human ABCC-like gene, designated ABCC11. The applicants have also determined that this novel gene is located in the region of chromosome 16q12 (FIG. 2).

The applicants have also determined that the ABCC11 gene has a unique expression pattern, suggesting that the corresponding proteins may perform tissue-specialized functions (Example 5). In effect, the expression pattern of ABCC11 gene was examined by RT-PCR on mRNA of 16 different human tissues (Clontech). Expression pattern showed that the approximately 5 Kb ABCC11 transcript was expressed in all tissues, except kidney, spleen, and colon.

The applicants have further determined potential transcript sequence that corresponds to the full coding sequence (CDS) of ABCC11, and that the ABCC11 according to the invention comprises 29 exons and 28 introns. All exons were flanked by GT and AG dinucleotides consistent with the consensus sequences for splice junctions in eukaryotic genes (Table 1).

TABLE 1

Splice sites sequences and exon sizes of ABCC11
ABCC11

| Exon | Size (bp) | Splice acceptor | Splice donor |
|---|---|---|---|
| 1 | 5'UTR + 99 | Not determined | ACTTATTTATgtaagtagat |
| 2 | 137 | cttttccaagAAAACCTATA | CCAAGCCGAGgtgagtcctg |
| 3 | 159 | cctctactagGTTTCCTGCC | ATGTCCAAAGgtgaagctgc |
| 4 | 148 | tcttttcaagGCTTCACCGC | ACTCGGGCCAgtaagtggca |
| 5 | 234 | ttccttgtagATATTGATTA | CTCAGGAGAGgtaagcagct |
| 6 | 174 | tgtcttgcagGCCATCAGCT | CCCACTGGCGgtaatgtctt |
| 7 | 148 | ctgactccagGTATTCATGA | ATCATTGAAGgtatggaaag |
| 8 | 149 | tatttcccagACCTAAGAAG | AGCGTCAATGgtaagggttt |
| 9 | 108 | tcttatccagGCCTTCAGCA | GAGGTTCAAGgtaggtcatc |
| 10 | 252 | gtctttacagAAGTTTTTCC | GGTGTCCAAGgtagccttgt |
| 11 | 72 | tggcttgcagGGGATGATGT | CCTGGAGGAGgtaagtgatc |
| 12 | 125 | tctgccgcagATGCACTTGC | ACAAGGCCCGgtaagctcct |
| 13 | 73 | tccttcacagATACCTCCAG | CATGACAGAGgtgagaggga |
| 14 | 204 | ccgtctgcagATTGGAGAGC | CCAGCTGCAGgttagcaccc |
| 15 | 135 | gactgtccagTACTTAGAAT | AGCCACTTCGgtgagtcctg |
| 16 | 97 | ctctcccagGACATGTTGC | GGAAATGCTGgtaatggtgt |
| 17 | 90 | cctgacccagTGCCGGAGCA | GCAGCTGGAGgtacggtccc |
| 18 | 104 | tccctcccagGTTACATGGT | GGGCTCGGGGgtgagtgcca |
| 19 | 198 | tttcttgaagACCAATAGCA | CTTCAACAAGgtatgggcct |
| 20 | 227 | gtccctgcagGTTTTCCGCT | TTTATTATATgtgagtaggt |
| 21 | 138 | gtccatgcagGATGTTCAAG | TCATCAGCCAgtgagtcctt |
| 22 | 187 | tccttctcagGTTTAAGAGG | CGTGCTGCAGgtgaggggt |
| 23 | 90 | ttccttctagCTGGCGTCCA | GTACATGAAGgtggggttca |
| 24 | 190 | caaaaacaagATGTGTGTCT | ACGGGCTCTGgtgagctgag |
| 25 | 160 | tgccccacagGGAAGTCCTC | GAACCATCAGgtgagtgccg |
| 26 | 79 | catatggtagATTCAACCTA | GACCAAGGCCgtaagtagct |
| 27 | 114 | catatcgcagATCTCAAAGT | CAACTCCAAGgtgaggccac |
| 28 | 165 | tattcatcagATCATCCTTA | CAATGGGAAGgtgaaggctg |
| 29 | 93+3'UTR | taccctccagGTGGTAGAAT | Not determined |

The applicants have thus characterized exonic sequences of a novel human ABCC11 gene, which are particularly useful according to the invention for the production of various means of detection of the corresponding ABCC11 gene, or nucleotide expression products in a sample.

Several exons of ABCC11 gene have been characterized by their nucleotide sequence and are identified in Table 2.

The human ABCC11 gene consists of 29 exons, having sizes which range from 72 to 252 bp. Of the 28 introns in the ABCC11 gene, 18 are class 0 (where the splice occurs between codons), four are class 1 (where the codon is interrupted between the first and the second nucleotide), and six are class 2 (where the splice occurs between the second and the third nucleotide of the codon).

TABLE 2

Human ABCC11 exons and introns DNA

| SEQ ID NO: | Exon or intron number | Exon starts in mRNA | Exon stops in mRNA | Exon starts in genomic fragment | Exon stops in genomic fragment | Length of exon | Intron starts in fragment | Intron stops in fragment | Length of intron |
|---|---|---|---|---|---|---|---|---|---|
| 2 | 1 | 1 | 5'UTR + 99 | 25501 | 25949 | | 25950 | 27198 | 1249 |
| 3 | 2 | 450 | 586 | 27199 | 27335 | 137 | 27336 | 29807 | 2472 |
| 4 | 3 | 587 | 745 | 29808 | 29966 | 159 | 29967 | 33342 | 3376 |
| 5 | 4 | 746 | 893 | 33343 | 33490 | 148 | 33491 | 34940 | 1450 |
| 6 | 5 | 894 | 1127 | 34941 | 35174 | 234 | 35175 | 41483 | 6309 |
| 7 | 6 | 1128 | 1301 | 41484 | 41657 | 174 | 41658 | 42426 | 769 |
| 8 | 7 | 1302 | 1449 | 42427 | 42574 | 148 | 42575 | 42741 | 167 |
| 9 | 8 | 1450 | 1598 | 42742 | 42890 | 149 | 42891 | 44220 | 1330 |
| 10 | 9 | 1599 | 1706 | 44221 | 44328 | 108 | 44329 | 46571 | 2243 |
| 11 | 10 | 1707 | 1958 | 46572 | 46823 | 252 | 46824 | 49274 | 2451 |
| 12 | 11 | 1959 | 2030 | 49275 | 49346 | 72 | 49347 | 52233 | 2887 |
| 13 | 12 | 2031 | 2155 | 52234 | 52358 | 125 | 52359 | 54470 | 2112 |
| 14 | 13 | 2156 | 2228 | 54471 | 54543 | 73 | 54544 | 57290 | 2747 |
| 15 | 14 | 2229 | 2432 | 57291 | 57494 | 204 | 57495 | 59492 | 1998 |
| 16 | 15 | 2433 | 2567 | 59493 | 59627 | 135 | 59628 | 59700 | 73 |
| 17 | 16 | 2568 | 2664 | 59701 | 59797 | 97 | 59798 | 61447 | 1650 |
| 18 | 17 | 2665 | 2754 | 61448 | 61537 | 90 | 61538 | 63786 | 2249 |
| 19 | 18 | 2755 | 2858 | 63787 | 63890 | 104 | 63891 | 65051 | 1161 |
| 20 | 19 | 2859 | 3056 | 65052 | 65249 | 198 | 65250 | 70341 | 5092 |
| 21 | 20 | 3057 | 3283 | 70342 | 70568 | 227 | 70569 | 70678 | 110 |
| 22 | 21 | 3284 | 3421 | 70679 | 70816 | 138 | 70817 | 73142 | 2326 |
| 23 | 22 | 3422 | 3608 | 73143 | 73329 | 187 | 73330 | 79082 | 5753 |
| 24 | 23 | 3609 | 3698 | 79083 | 79172 | 90 | 79173 | 80655 | 1483 |
| 25 | 24 | 3699 | 3888 | 80656 | 80845 | 190 | 80846 | 82351 | 1506 |
| 26 | 25 | 3889 | 4048 | 82352 | 82511 | 160 | 82512 | 86801 | 4290 |
| 27 | 26 | 4049 | 4127 | 86802 | 86880 | 79 | 86881 | 87550 | 670 |
| 28 | 27 | 4128 | 4241 | 87551 | 87664 | 114 | 87665 | 90108 | 2444 |
| 29 | 28 | 4242 | 4406 | 90109 | 90273 | 165 | 90274 | 90402 | 129 |
| 30 | 29 | 4407 | 4862 | 90403 | 90858 | 93 +3' UTR | | | |

Thus the present invention also relates to a nucleic acid comprising any one of SEQ ID NOS:1–30, or a complementary sequence thereof.

The invention also relates to a nucleic acid comprising a nucleotide sequence as depicted in any one of SEQ ID NOS:1–30, or a complementary nucleotide sequence thereof.

The invention also relates to a nucleic acid comprising at least 8 consecutive nucleotides of any one of SEQ ID NOS:1–30, or a complementary nucleotide sequence.

The subject of the invention is, in addition, a nucleic acid having at least 80% nucleotide identity with a nucleic acid comprising any one of SEQ ID NOS:1–30, or a complementary nucleotide sequence thereof.

The invention also relates to a nucleic acid having at least 85%, 90%, 95%, or 98% nucleotide identity with a nucleic acid comprising any one of SEQ ID NOS:1–30.

The invention also relates to a nucleic acid hybridizing, under high stringency conditions, with a nucleic acid comprising any one of SEQ ID NOS:1–30, or a complementary nucleotide sequence thereof.

cDNA Molecule Encoding the ABCC11 Protein

The applicants have further determined the cDNA sequences and the full coding sequences (CDS) corresponding to the human ABCC11 gene, and encodes the full length human corresponding protein (Example 2).

The cDNA molecule of the novel human ABCC11 gene consists of 4862 nucleotides as set forth in SEQ ID NO:1 and contains a 4182 nucleotide coding sequence corresponding to a 1382 amino acids (aa) ABCC11 polypeptide (SEQ ID NO:31) produced in subjects not affected by disorders of paroxysmal kinesigenic choreoathotesis. The cDNA molecule of the novel human ABCC11 gene having the nucleotide sequence as set forth in SEQ ID NO:1 comprises an open reading frame beginning from the nucleotide at position 318 to the nucleotide at position 4499 (base A of the TAA stop codon). According to the invention the ABCC11 cDNA (SEQ ID NO:1) contains a 4149 bp coding sequence from the nucleotide 351 (base A of the ATG codon for initiation of translation) to the nucleotide 4499 of SEQ ID NO:1, which encodes a full length ABCC11 polypeptide of 1382 amino acids of sequence SEQ ID NO:31.

The present invention is thus directed to a nucleic acid comprising SEQ ID NO:1, or a complementary nucleotide sequence thereof.

The invention also relates to a nucleic acid comprising a nucleotide sequence as depicted in SEQ ID NO:1, or a complementary nucleotide sequence thereof.

The invention also relates to a nucleic acid comprising at least eight consecutive nucleotides of SEQ ID NO:1, or a complementary nucleotide sequence thereof.

The subject of the invention is also a nucleic acid having at least 80% nucleotide identity with a nucleic acid comprising nucleotides of SEQ ID NO:1, or a nucleic acid having a complementary nucleotide sequence thereof.

The invention also relates to a nucleic acid having at least 85%, 90%, 95%, or 98% nucleotide identity with a nucleic acid comprising a nucleotide sequence of SEQ ID NO:1, or a complementary nucleotide sequence thereof.

Another subject of the invention is a nucleic acid hybridizing, under high stringency conditions, with a nucleic acid comprising nucleotide sequence of SEQ ID NO:1, or a nucleic acid having a complementary nucleotide sequence thereof.

The invention also relates to a nucleic acid encoding a polypeptide comprising an amino acid sequence of SEQ ID NO:31.

The invention relates to a nucleic acid encoding a polypeptide comprising an amino acid sequence as depicted in SEQ ID NO:31.

The invention also relates to a polypeptide comprising amino acid sequence of SEQ ID NO:31.

The invention also relates to a polypeptide comprising amino acid sequence as depicted in SEQ ID NO:30.

The invention also relates to a polypeptide comprising an amino acid sequence having at least 80% amino acid identity with a polypeptide comprising an amino acid sequence of SEQ ID NO:31, or a peptide fragment thereof.

The invention also relates to a polypeptide having at least 85%, 90%, 95%, or 98% amino acid identity with a polypeptide comprising an amino acid sequence of SEQ ID NO:31.

A polypeptide according to the invention may have a length of 4, 5 to 10, 15, 18 or 20 to 25, 35, 40, 50, 70, 80, 100 or 200 consecutive amino acids of a polypeptide according to the invention comprising an amino acid sequence of SEQ ID NO:31.

Figure 1:
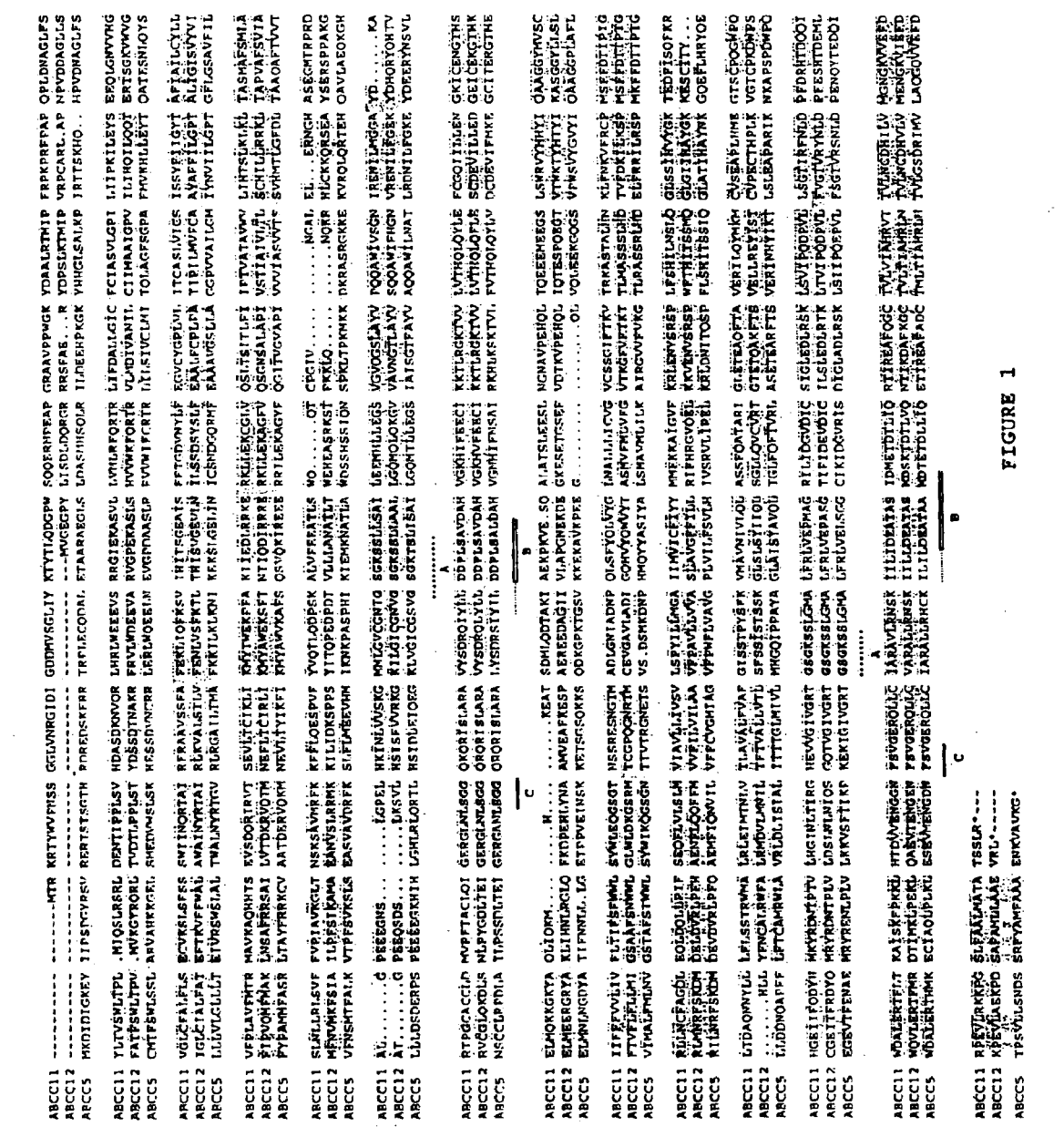

Topology predictions based on hydropathy profiles and comparison with other known ABC transporters, suggest that the encoded ABCC11 protein is a full ABC transporters containing two ATP-binding domains (including Walker A and B domains, and signature motifs) and two transmembrane domains (FIG. 1). The amino acid sequence of ABCC11 is 41% identical to the human ABCC5 protein, 36% to human ABCC4 and 32% identical to human ABCC2 and ABCC3 proteins. The ABCC11 protein, like ABCC4 and ABCC5 proteins, is smaller than another well-known member of the subgroup, ABCC1 (MRP1), appearing to lack the extra N-terminal domain (Borst et al., *J Natl Cancer Inst*, 2000, 92, 1295–302), which has been shown, however, not to be required for the transport function (Bakos et al., *J. Biol. Chem.*, 1998, 273, 32167–75).

TABLE 3

Homology/Identity percentages between the amino acid sequences of ABCC11, ABCC12, ABCC5, ABCC4, ABCC1, and ABCA1 along the entire sequence

| Total sequence | ABCC11 | ABCC12 | ABCC5 | ABCC4 | ABCC1 | ABCA1 |
|---|---|---|---|---|---|---|
| ABCC11 | 100/100 | | | | | |
| ABCC12 | 59/49 | 100/100 | | | | |
| ABCC5 | 50/41 | 52/42 | 100/100 | | | |
| ABCC4 | 47/36 | 50/39 | 51/41 | 100/100 | | |
| ABCC1 | 44/33 | 47/35 | 47/36 | 53/44 | 100/100 | |
| ABCA1 | — | — | — | — | — | 100/100 |

Alignment of the amino acid sequences of ABCC11, ABCC12, and ABCC5 genes reveals an identity ranging from 49 to 41% along the entire sequence (Table 3 and FIG. 1).

Figure 4:
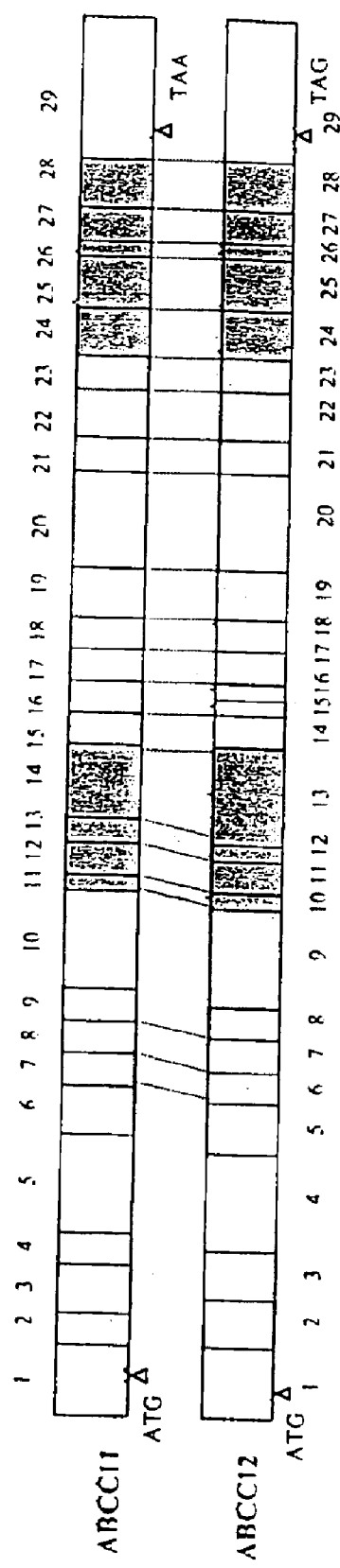
FIG. 4 displays the splicing pattern of the ABCC11 and ABCC12 genes. Clear boxes represent exons, and vertical lines define splice sites. The exon numbers for each gene is shown both above and below the drawing. Filled boxes indicate the exons coding for ABC domains.

Phylogenetic analysis of the ABCC subfamily proteins clearly demonstrates a close evolutionary relationship of the ABCC11 gene with the ABCC5 gene (FIG. 4). In addition, the analysis of the tree suggests a recent duplication of the ABCC8 and ABCC9 genes, while ABCC10 seems to be one of the first genes to separate from the common ancestor. ABCC1, ABCC2, ABCC3, and ABCC6 genes constitute a well-defined sub-cluster, while the ABCC4 and CFTR (ABCC7) genes form another reliable subset despite apparent early divergence.

Polymorphisms within the ABCC11 Gene

The analysis of mutations in the ABCC11 gene may be carried out on genomic DNA from several individuals belonging to a family of which several members suffer from the paroxysmal kinesigenic choreoathetoris. According to the invention, a single nucleotide polymorphism has been identified in the coding region of the ABCC11 gene, which encodes the ABCC11 polypeptide. This mutation is more precisely located in the first exon, wherein a G (Guanine) was replaced by a A (adenine) in position 56 of SEQ ID NO:1, and results in the replacing of an arginine (R) by an histidine (H) at position 19 of the sequence SEQ ID NO:31.

The structural characteristics that make it possible to differentiate the normal sequences from the mutated sequences of ABCC11 (genomic sequences, messenger RNAs, cDNA) may be exploited in order to produce means of detection of the mutated sequences of ABCC11 in a sample, in particular, probes specifically hybridizing with the mutated sequences of ABCC11 or pairs of primers making it possible to selectively amplify the regions of the ABCC11 gene carrying the mutations described above, it being possible to carry out the detection of the presence of these mutations in particular by distinguishing the length of the amplified nucleic acid fragments, by hybridization of the amplified fragments with the aid of the specific probes described above, or by direct sequencing of these amplified fragments.

The detection of these polymorphisms in a DNA sample obtained from a subject may also be carried out with the aid of nucleotide probes or primers specifically hybridizing with a given allele containing one of the polymorphic bases of a polymorphism of the ABCC11 gene according to the invention.

By way of illustration, appropriate nucleotide primers are for example primers whose base at the 3' end hybridizes with the base located immediately on the 5' side of the polymorphic base of the fragment comprising said polymorphism. After the step of hybridization of the specific primer, a step of extension with a mixture of the two dideoxynucleotides complementary to the polymorphic base of said polymorphism, for example differentially labeled by fluorescence, and then a step detection of the fluorescence signal obtained makes it possible to determine which of the two differentially labeled fluorescent dideoxynucleotides has been incorporated and to directly deduce the nature of the polymorphic base present at the level of this polymorphism.

Various approaches may be used for the labeling and detection of the dideoxynucleotides. A method in homogeneous phase based on FRET ("Fluorescence resonance energy transfer") has been described by Chen and Kwok (1997). According to this method, the amplified fragments of genomic DNA containing polymorphisms are incubated with a primer labeled with fluorescein at the 5' end in the presence of labeled dideoxynucleotide triphosphate and a modified Taq polymerase. The labeled primer is extended by one base by incorporation of the labeled dideoxynucleotide specific for the allele present on the complementary genomic DNA sequence. At the end of this genotyping reaction, the fluorescence intensities for the two labeling compounds for the labeled dideoxynucleotides are directly analyzed without separation or purification. All these steps may be carried out in the same tube and the modifications of the fluorescence signal monitored in real time. According to another embodiment, the extended primer may be analyzed by MALDI-TOF type mass spectrometry. The base located at the level of the polymorphic site is identified by measuring the mass added to the microsequencing primer (Haff and Smirnov, 1997).

Such nucleotide primers may, for example, be immobilized on a support. Furthermore, it is possible to immobilize on a support, for example in an orderly manner, multiple specific primers as described above, each of the primers being suited to the detection of one of the polymorphisms of the ABCC11 gene according to the invention.

The polymorphisms of the ABCC11 gene according to the invention are useful as genetic markers in studies of the association between the presence of a given allele in a subject and the predisposition of this subject to a given pathology, for example, to one of the pathologies already associated with the chromosomal region 16q12, and for example, to a pathology linked to a dysfunction in the reverse transport of cholesterol.

The methods for the genetic analysis of complex characters (phenotypes) are of various types (Lander and Schork, 1994, Science, 265, 2037–2048, 1994). In general, the biallelic polymorphisms according to the invention are useful in any of the methods described in the state of the art intended to demonstrate a statistically significant correlation between a genotype and a phenotype. The biallelic polymorphisms may be used in linkage analyses and in allele sharing methods. The biallelic polymorphisms according to the invention may be used to identify genes associated with detectable characters (phenotypes) in use for studies of association, an approach which does not require the use of families affected by the character, and which allows, in addition, the identification of genes associated with complex and sporadic characters.

Other statistical methods using biallelic polymorphisms according to the invention are for example those described by Forsell et al. (Biol. Psychiatry, 1997, 42: 898–903), Xiong et al. (Am. J. Hum. Genet., 1999, 64: 629–640), Horvath et al. (Am. J. Hum. Genet., 1998, 63 :1886–1897.), Sham et al. (Ann. Hum. Genet., 1995, 59: 323–336) or Nickerson et al. (Genomics, 1992, 12: 377–387).

Nucleotide Probes and Primers

Nucleotide probes and primers hybridizing with a nucleic acid (genomic DNA, messenger RNA, cDNA) according to the invention also form part of the invention.

According to the invention, nucleic acid fragments derived from a polynucleotide comprising any one of SEQ ID NOS:1–30 or of a complementary nucleotide sequence are useful for the detection of the presence of at least one copy of a nucleotide sequence of the ABCC11 gene or of a fragment or of a variant (containing a mutation or a polymorphism) thereof in a sample.

The nucleotide probes or primers according to the invention comprise a nucleotide sequence comprising any one of SEQ ID NOS:1–30, or a complementary nucleotide sequence thereof.

The nucleotide probes or primers according to the invention comprise at least 8 consecutive nucleotides of a nucleic acid comprising any one of SEQ ID NOS:1–30, or a complementary nucleotide sequence.

Nucleotide probes or primers according to the invention may have a length of 10, 12, 15, 18 or 20 to 25, 35, 40, 50, 70, 80, 100, 200, 500, 1000, or 1500 consecutive nucleotides of a nucleic acid according to the invention, in particular of a nucleic acid comprising any one of SEQ ID NOS:1–30, or a complementary nucleotide sequence.

Alternatively, a nucleotide probe or primer according to the invention consists of and/or comprise the fragments having a length of 12, 15, 18, 20, 25, 35, 40, 50, 100, 200, 500, 1000, or 1500 consecutive nucleotides of a nucleic acid according to the invention, more particularly of a nucleic acid comprising any one of SEQ ID NOS:1–30, or a complementary nucleotide sequence.

The definition of a nucleotide probe or primer according to the invention therefore covers oligonucleotides hybridizing, under the high stringency hybridization conditions defined above, with a nucleic acid comprising any one of SEQ ID NOS:1–30, or a complementary nucleotide sequence.

A nucleotide primer or probe according to the invention may be prepared by any suitable method well known to persons skilled in the art, including by cloning and action of restriction enzymes or by direct chemical synthesis according to techniques such as the phosphodiester method by Narang et al. (1979, Methods Enzymol, 68:90–98) or by Brown et al. (1979, Methods Enzymol, 68:109–151), the diethylphosphoramidite method by Beaucage et al. (1981, Tetrahedron Lett, 22: 1859–1862) or the technique on a solid support described in European patent No. EP 0,707,592.

Each of the nucleic acids according to the invention, including the oligonucleotide probes and primers described above, may be labeled, if desired, by incorporating a marker which can be detected by spectroscopic, photochemical, biochemical, immunochemical or chemical means. For example, such markers may consist of radioactive isotopes ($^{32}P$, $^{33}P$, $^{3}H$, $^{35}S$), fluorescent molecules (5-bromodeoxyuridine, fluorescein, acetylaminofluorene, digoxigenin) or ligands such as biotin. The labeling of the probes may be carried out by incorporating labeled molecules into the polynucleotides by primer extension, or alternatively by addition to the 5' or 3' ends. Examples of nonradioactive labeling of nucleic acid fragments are described in particular in French patent No. 78 109 75 or in the articles by Urdea et al. (1988, Nucleic Acids Research, 11:4937–4957) or Sanchez-Pescador et al. (1988, J. Clin. Microbiol., 26(10):1934–1938).

The nucleotide probes and primers according to the invention may have structural characteristics of the type to allow amplification of the signal, such as the probes described by Urdea et al. (1991, Nucleic Acids Symp Ser., 24:197–200) or alternatively in European patent No. EP-0, 225,807 (CHIRON).

The oligonucleotide probes according to the invention may be used in particular in Southern-type hybridizations with the genomic DNA or alternatively in northern-type hybridizations with the corresponding messenger RNA when the expression of the corresponding transcript is sought in a sample.

The probes and primers according to the invention may also be used for the detection of products of PCR amplification or alternatively for the detection of mismatches.

Nucleotide probes or primers according to the invention may be immobilized on a solid support. Such solid supports are well known to persons skilled in the art and comprise surfaces of wells of microtiter plates, polystyrene beads, magnetic beads, nitrocellulose bands or microparticles such as latex particles.

Consequently, the present invention also relates to a method of detecting the presence of a nucleic acid comprising a nucleotide sequence of any one of SEQ ID NOS:1–30, or of a complementary nucleotide sequence, or a nucleic acid fragment or variant of any one of SEQ ID NOS:1–30, or of a complementary nucleotide sequence in a sample, said method comprising the steps of:

1) bringing one or more nucleotide probes or primers according to the invention into contact with the sample to be tested;
2) detecting the complex which may have formed between the probe(s) and the nucleic acid present in the sample.

According to a specific embodiment of the method of detection according to the invention, the oligonucleotide probes and primers are immobilized on a support.

According to another aspect, the oligonucleotide probes and primers comprise a detectable marker.

The invention relates, in addition, to a box or kit for detecting the presence of a nucleic acid according to the invention in a sample, said box or kit comprising:

a) one or more nucleotide probe(s) or primer(s) as described above;

b) where appropriate, the reagents necessary for the hybridization reaction.

According to a first aspect, the detection box or kit is characterized in that the probe(s) or primer(s) are immobilized on a support.

According to a second aspect, the detection box or kit is characterized in that the oligonucleotide probes comprise a detectable marker.

According to a specific embodiment of the detection kit described above, such a kit will comprise a plurality of oligonucleotide probes and/or primers in accordance with the invention which may be used to detect a target nucleic acid of interest or alternatively to detect mutations in the coding regions or the non-coding regions of the nucleic acids according to the invention, more particularly of nucleic acids comprising any one of SEQ ID NOS:1–30, or a complementary nucleotide sequence.

Thus, the probes according to the invention, immobilized on a support, may be ordered into matrices such as "DNA chips." Such ordered matrices have in particular been described in U.S. Pat. No. 5,143,854, in published PCT applications WO 90/15070 and WO 92/10092.

Support matrices on which oligonucleotide probes have been immobilized at a high density are for example described in U.S. Pat. No. 5,412,087 and in published PCT application WO 95/11995.

The nucleotide primers according to the invention may be used to amplify any one of the nucleic acids according to the invention, and more particularly a nucleic acid comprising a nucleotide sequence of any one of SEQ ID NOS:1–30, or of a complementary nucleotide sequence. Alternatively, the nucleotide primers according to the invention may be used to amplify a nucleic acid fragment or variant of any one of SEQ ID NOS:1–30, or of a complementary nucleotide sequence.

In a particular embodiment, the nucleotide primers according to the invention may be used to amplify a nucleic acid comprising any one of SEQ ID NOS:1–30, or as depicted in any one of SEQ ID NOS:1–30, or of a complementary nucleotide sequence.

Another subject of the invention relates to a method of amplifying a nucleic acid according to the invention, and more particularly a nucleic acid comprising a) any one of SEQ ID NOS:1–30, or a complementary nucleotide sequence, b) as depicted in any one of SEQ ID NOS:1–30, or of a complementary nucleotide sequence, contained in a sample, said method comprising the steps of:

a) bringing the sample in which the presence of the target nucleic acid is suspected into contact with a pair of nucleotide primers whose hybridization position is located respectively on the 5' side and on the 3' side of the region of the target nucleic acid whose amplification is sought, in the presence of the reagents necessary for the amplification reaction; and b) detecting the amplified nucleic acids.

To carry out the amplification method as defined above, use may be made of any of the nucleotide primers described above.

The subject of the invention is, in addition, a box or kit for amplifying a nucleic acid according to the invention, and more particularly a nucleic acid comprising any one of SEQ ID NOS:1–30, or a complementary nucleotide sequence, or as depicted in any one of SEQ ID NOS:1–30, or of a complementary nucleotide sequence, said box or kit comprising:

a) a pair of nucleotide primers in accordance with the invention, whose hybridization position is located respectively on the 5' side and 3' side of the target nucleic acid whose amplification is sought; and optionally, b) reagents necessary for the amplification reaction.

Such an amplification box or kit may comprise at least one pair of nucleotide primers as described above.

The subject of the invention is, in addition, a box or kit for amplifying all or part of a nucleic acid comprising any one of SEQ ID NOS:1–30, or a complementary nucleotide sequence, said box or kit comprising:

1) a pair of nucleotide primers in accordance with the invention, whose hybridization position is located respectively on the 5' side and 3' side of the target nucleic acid whose amplification is sought; and optionally, 2) reagents necessary for an amplification reaction.

Such an amplification box or kit may comprise at least one pair of nucleotide primers as described above.

The invention also relates to a box or kit for detecting the presence of a nucleic acid according to the invention in a sample, said box or kit comprising:

a) one or more nucleotide probes according to the invention;

b) where appropriate, reagents necessary for a hybridization reaction.

According to a first aspect, the detection box or kit is characterized in that the nucleotide probe(s) and primer(s) are immobilized on a support.

According to a second aspect, the detection box or kit is characterized in that the nucleotide probe(s) and primer(s) comprise a detectable marker.

According to a specific embodiment of the detection kit described above, such a kit will comprise a plurality of oligonucleotide probes and/or primers in accordance with the invention which may be used to detect target nucleic acids of interest or alternatively to detect mutations in the coding regions or the non-coding regions of the nucleic acids according to the invention. According to some embodiments of the invention, the target nucleic acid comprises a nucleotide sequence of any one of SEQ ID NOS:1–30, or of a complementary nucleic acid sequence. Alternatively, the target nucleic acid is a nucleic acid fragment or variant of a nucleic acid comprising any one of SEQ ID NOS:1–30, or of a complementary nucleotide sequence.

The nucleotide primers according to the invention are particularly useful in methods of genotyping subjects and/or of genotyping populations, in particular in the context of studies of association between particular allele forms or particular forms of groups of alleles (haplotypes) in subjects and the existence of a particular phenotype (character) in these subjects, for example the predisposition of these subjects to develop diseases a pathology whose candidate chromosomal region is situated on chromosome 16, more precisely on the 16q arm and still more precisely in the 16q12 locus, such as a paroxysmal kinesigenic choreoathetosis.

Recombinant Vectors

The invention also relates to a recombinant vector comprising a nucleic acid according to the invention. "Vector" for the purposes of the present invention will be understood to mean a circular or linear DNA or RNA molecule which is either in single-stranded or double-stranded form.

Such a recombinant vector may comprise a nucleic acid chosen from the following nucleic acids:

a) a nucleic acid comprising a nucleotide sequence of any one of SEQ ID NOS:1–30, or a complementary nucleotide sequence thereof;

b) a nucleic acid comprising a nucleotide sequence as depicted in any one of SEQ ID NOS:1–29, or a complementary nucleotide sequence thereof;

c) a nucleic acid having at least eight consecutive nucleotides of a nucleic acid comprising a nucleotide sequence of any one of SEQ ID NOS:1–30, or of a complementary nucleotide sequence thereof;

d) a nucleic acid having at least 80% nucleotide identity with a nucleic acid comprising a nucleotide sequence of any one of SEQ ID NOS:1–30, or a complementary nucleotide sequence thereof;

e) a nucleic acid having 85%, 90%, 95%, or 98% nucleotide identity with a nucleic acid comprising a nucleotide sequence of any one of SEQ ID NOS:1–30, or a complementary nucleotide sequence thereof;

f) a nucleic acid hybridizing, under high stringency hybridization conditions, with a nucleic acid comprising a nucleotide sequence of 1) any one of SEQ ID NOS:1–30, or a complementary nucleotide sequence thereof;

g) a nucleic acid encoding a polypeptide comprising an amino acid sequence of SEQ ID NO:31; and h) a nucleic acid encoding a polypeptide comprising amino acid sequence SEQ ID NO:31.

According to a first embodiment, a recombinant vector according to the invention is used to amplify a nucleic acid inserted therein, following transformation or transfection of a desired cellular host.

According to a second embodiment, a recombinant vector according to the invention corresponds to an expression vector comprising, in addition to a nucleic acid in accordance with the invention, a regulatory signal or nucleotide sequence that directs or controls transcription and/or translation of the nucleic acid and its encoded mRNA.

According to some embodiments, a recombinant vector according to the invention will comprise in particular the following components:

1) an element or signal for regulating the expression of the nucleic acid to be inserted, such as a promoter and/or enhancer sequence;

2) a nucleotide coding region comprised within the nucleic acid in accordance with the invention to be inserted into such a vector, said coding region being placed in phase with the regulatory element or signal described in (1); and 3) an appropriate nucleic acid for initiation and termination of transcription of the nucleotide coding region of the nucleic acid described in (2).

In addition, the recombinant vectors according to the invention may include one or more origins for replication in the cellular hosts in which their amplification or their expression is sought, markers or selectable markers.

By way of example, the bacterial promoters may be the LacI or LacZ promoters, the T3 or T7 bacteriophage RNA polymerase promoters, the lambda phage PR or PL promoters.

The promoters for eukaryotic cells will comprise the herpes simplex virus (HSV) virus thymidine kinase promoter or alternatively the mouse metallothionein-L promoter.

Generally, for the choice of a suitable promoter, persons skilled in the art can refer to the book by Sambrook et al. (1989, *Molecular cloning: a laboratory manual.* 2ed. Cold Spring Harbor Laboratory, Cold Spring Harbor, N.Y.) cited above or to the techniques described by Fuller et al. (1996, *Immunology, In: Current Protocols in Molecular Biology,* Ausubel et al.(eds.).

When the expression of the genomic sequence of any one of the ABCC11 gene will be sought, use may be made of the vectors capable of containing large insertion sequences. In a particular embodiment, bacteriophage vectors such as the P1 bacteriophage vectors such as the vector p158 or the vector p158/neo8 described by Sternberg (1992, Trends Genet., 8:1–16; 1994, *Mamm. Genome,* 5:397–404) maybe used.

The bacterial vectors according to the invention are for example the vectors pBR322(ATCC37017) or alternatively vectors such as pAA223-3 (Pharmacia, Uppsala, SWEDEN), and pGEM1(Promega Biotech, Madison, Wis. UNITED STATES).

There may also be cited other commercially available vectors such as the vectors pQE70, pQE60, pQE9 (Qiagen), psiX174, pBluescript SA, pNH8A, pNH16A, pNH18A, pNH46A, pWLNEO, pSV2CAT, pOG44, pXTI, pSG (Stratagene).

They may also be vectors of the baculovirus type such as the vector pVL1392/1393 (Pharmingen) used to transfect cells of the Sf9 line (ATCC No. CRL 1711) derived from *Spodoptera frugiperda*.

They may also be adenoviral vectors such as the human adenovirus of type 2 or 5.

A recombinant vector according to the invention may also be a retroviral vector or an adeno-associated vector (AAV). Such adeno-associated vectors are for example described by Flotte et al. (1992, *Am. J Respir. Cell Mol. Biol.,* 7:349–356), Samulski et al. (1989, *J Virol.,* 63:3822–3828), or McLaughlin BA et al. (1996, *Am. J Hum. Genet.,* 59:561–569).

To allow the expression of a polynucleotide according to the invention, the latter must be introduced into a host cell. The introduction of a polynucleotide according to the invention into a host cell may be carried out in vitro, according to the techniques well known to persons skilled in the art for transforming or transfecting cells, either in primer culture, or in the form of cell lines. It is also possible to carry out the introduction of a polynucleotide according to the invention in vivo or ex vivo, for the prevention or treatment of diseases linked to ABCC11 deficiencies.

To introduce a polynucleotide or vector of the invention into a host cell, a person skilled in the art can refer to various techniques, such as the calcium phosphate precipitation technique (Graham et al., 1973, *Virology,* 52:456–457; Chen et al., 1987, *Mol. Cell. Biol.,* 7: 2745–2752), DEAE Dextran (Gopal, 1985, *Mol. Cell. Biol.,* 5:1188–1190), electroporation (Tur-Kaspa, 1896, *Mol. Cell. Biol.,* 6:716–718;Potter et al., 1984, *Proc Natl Acad Sci USA.,* 81(22):7161–5), direct microinjection (Harland et al., 1985, *J. Cell. Biol.,* 101:1094–1095), liposomes charged with DNA (Nicolau et al., 1982, *Methods Enzymol.,* 149:157–76; Fraley et al., 1979, *Proc. Natl. Acad. Sci. USA,* 76:3348–3352).

Once the polynucleotide has been introduced into the host cell, it may be stably integrated into the genome of the cell. The intregration may be achieved at a precise site of the genome, by homologous recombination, or it may be randomly integrated. In some embodiments, the polynucleotide may be stably maintained in the host cell in the form of an episome fragment, the episome comprising sequences allowing the retention and the replication of the latter, either independently, or in a synchronized manner with the cell cycle.

According to a specific embodiment, a method of introducing a polynucleotide according to the invention into a host cell, in particular a host cell obtained from a mammal, in vivo, comprises a step during which a preparation comprising a pharmaceutically compatible vector and a "naked" polynucleotide according to the invention, placed under the control of appropriate regulatory sequences, is introduced by local injection at the level of the chosen tissue, for example myocardial tissue, the "naked" polynucleotide being absorbed by the myocytes of this tissue.

Compositions for use in vitro and in vivo comprising "naked" polynucleotides are for example described in PCT Application No. WO 95/11307 (Institut Pasteur, Inserm, University of Ottawa) as well as in the articles by Tacson et al. (1996, Nature Medicine, 2(8):888–892) and Huygen et al. (1996, Nature Medicine, 2(8):893–898).

According to a specific embodiment of the invention, a composition is provided for the in vivo production of the ABCC11 protein. This composition comprises a polynucleotide encoding the ABCC11 polypeptide placed under the control of appropriate regulatory sequences, in solution in a physiologically acceptable vector.

The quantity of vector which is injected into the host organism chosen varies according to the site of the injection. As a guide, there may be injected between about 0.1 and about 100 µg of polynucleotide encoding the ABCC11 protein into the body of an animal, such as into the body of a patient likely to develop a disease linked ABCC11 deficiency.

Consequently, the invention also relates to a pharmaceutical composition intended for the prevention of or treatment of a patient or subject affected by ABCC11 deficiency, comprising a nucleic acid encoding the ABCC11 protein, in combination with one or more physiologically compatible excipients.

Preferably, such a composition will comprise a nucleic acid comprising a nucleotide sequence of SEQ ID NO:1, wherein the nucleic acid is placed under the control of an appropriate regulatory element or signal.

The subject of the invention is, in addition, a pharmaceutical composition intended for the prevention of or treatment of a patient or a subject affected ABCC11 deficiency, comprising a recombinant vector according to the invention, in combination with one or more physiologically compatible excipients.

The invention relates to the use of a nucleic acid according to the invention, encoding the ABCC11 protein, for the manufacture of a medicament intended for the prevention or the treatment of subjects affected by a paroxysmal kinesigenic choreoathetosis.

The invention also relates to the use of a recombinant vector according to the invention, comprising a nucleic acid encoding the ABCC11 protein, for the manufacture of a medicament intended for the prevention of paroxysmal kinesigenic choreoathetosis.

The invention further relates to the use of a nucleic acid according to the invention, encoding the ABCC11 protein, for the manufacture of a medicament intended for the prevention or the treatment of pathologies linked to the dysfunction of transport of anionic drugs, such as methotrexate (MTX), neutral drugs conjugated to acidic ligands, such as GSH, glucuronate, or sulfate.

The invention also relates to the use of a recombinant vector according to the invention, comprising a nucleic acid encoding the ABCC11 protein, for the manufacture of a medicament intended for the treatment of/and prevention of pathologies linked to the dysfunction of transport of anionic drugs, such as methotrexate (MTX), neutral drugs conjugated to acidic ligands, such as GSH, glucuronate, or sulfate.

The subject of the invention is therefore also a recombinant vector comprising a nucleic acid according to the invention that encodes the ABCC11 protein or polypeptide.

The invention also relates to the use of such a recombinant vector for the preparation of a pharmaceutical composition intended for the treatment and/or for the prevention of diseases or conditions associated with deficiency or paroxysmal kinesigenic chorcoathetosis.

The present invention also relates to the use of cells genetically modified ex vivo with such a recombinant vector according to the invention, or of cells producing a recombinant vector, wherein the cells are implanted in the body, to allow a prolonged and effective expression in vivo of at least a biologically active ABCC11 polypeptide.

Vectors useful in methods of somatic gene therapy and compositions containing such vectors.

The present invention also relates to a new therapeutic approach for the treatment of pathologies linked to ABCC11 deficiencies. It provides an advantageous solution to the disadvantages of the prior art, by demonstrating the possibility of treating the pathologies linked to the ABCC11 deficiency by gene therapy, by the transfer and expression in vivo of a gene encoding the ABCC11 protein involved in the paroxysmal kinesigenic choreoathetosis. The invention thus offers a simple means allowing a specific and effective treatment of the 16q12 located pathologies such as, paroxysmal kinesigenic choreoathetosis.

Gene therapy consists in correcting a deficiency or an abnormality (mutation, aberrant expression and the like) and in bringing about the expression of a protein of therapeutic interest by introducing genetic information into the affected cell or organ. This genetic information may be introduced either ex vivo into a cell extracted from the organ, the modified cell then being reintroduced into the body, or directly in vivo into the appropriate tissue. In this second case, various techniques exist, among which various transfection techniques involving complexes of DNA and DEAE-dextran (Pagano et al., J. Virol, 1 (1967)891), of DNA and nuclear proteins (Kaneda et al., 1989, Science 243:375), of DNA and lipids (Felgner et al., 1987, PNAS 84:7413), the use of liposomes (Fraley et al., 1980, J. Biol. Chem., 255:10431), and the like. More recently, the use of viruses as vectors for the transfer of genes has appeared as a promising alternative to these physical transfection techniques. In this regard, various viruses have been tested for their capacity to infect certain cell populations. In particular, the retroviruses (RSV, HMS, MMS, and the like), the HSV virus, the adeno-associated viruses and the adenoviruses.

The present invention therefore also relates to a new therapeutic approach for the treatment of pathologies linked to ABCC11 deficiencies, consisting in transferring and in expressing in vivo genes encoding ABCC11. The applicants have now found that it is possible to construct recombinant vectors comprising a nucleic acid encoding ABCC11 protein, to administer these recombinant vectors in vivo, and that this administration allows a stable and effective expression of at least one of the biologically active ABCC11 protein in vivo, with no cytopathological effect.

Adenoviruses constitute particularly efficient vectors for the transfer and the expression of any one of the ABCC11 gene. The use of recombinant adenoviruses as vectors makes it possible to obtain sufficiently high levels of expression of this gene to produce the desired therapeutic effect. Other viral vectors such as retroviruses or adeno-associated viruses (AAV) can allow a stable expression of the gene are also claimed.

The present invention is thus likely to offer a new approach for the treatment and prevention of ABCC11 deficiencies.

The subject of the invention is therefore also a defective recombinant virus comprising a nucleic acid according to the invention that encodes the ABCC11 protein or polypeptide.

The invention also relates to the use of such a defective recombinant virus for the preparation of a pharmaceutical composition which may be useful for the treatment and/or for the prevention of ABCC11 deficiencies.

The present invention also relates to the use of cells genetically modified ex vivo with such a defective recombinant virus according to the invention, or of cells producing a defective recombinant virus, wherein the cells are implanted in the body, to allow a prolonged and effective expression in vivo of the biologically active ABCC11 polypeptide.

The present invention is particularly advantageous because it is it possible to induce a controlled expression, and with no harmful effect of ABCC11 in organs which are not normally involved in the expression of this protein. In particular, a significant release of the ABCC11 protein is obtained by implantation of cells producing vectors of the invention, or infected ex vivo with vectors of the invention.

The activity of these ABCC protein transporters produced in the context of the present invention may be of the human or animal ABCC11 type. The nucleic sequence used in the context of the present invention may be a cDNA, a genomic DNA (gDNA), an RNA (in the case of retroviruses) or a hybrid construct consisting, for example, of a cDNA into which one or more introns (gDNA) would be inserted. It may also involve synthetic or semisynthetic sequences. In a particularly advantageous manner, a cDNA or a gDNA is used. In particular, the use of a gDNA allows a better expression in human cells. To allow their incorporation into a viral vector according to the invention, these sequences may be modified, for example by site-directed mutagenesis, in particular for the insertion of appropriate restriction sites. The sequences described in the prior art are indeed not constructed for use according to the invention, and prior adaptations may prove necessary, in order to obtain substantial expressions. In the context of the present invention, the use of a nucleic sequence encoding the human ABCC11 protein may be used. Moreover, it is also possible to use a construct encoding a derivative of the ABCC11 protein. A derivative of the ABCC11 protein comprises, for example, any sequence obtained by mutation, deletion and/or addition relative to the native sequence, and encoding a product retaining the lipophilic subtances transport activity. These modifications may be made by techniques known to a person skilled in the art (see general molecular biological techniques below). The biological activity of the derivatives thus obtained can then be easily determined, as indicated in particular in the examples of the measurement of the efflux of the substrate from cells. The derivatives for the purposes of the invention may also be obtained by hybridization from nucleic acid libraries, using as probe the native sequence or a fragment thereof.

These derivatives are in particular molecules having a higher affinity for their binding sites, molecules exhibiting greater resistance to proteases, molecules having a higher therapeutic efficacy or fewer side effects, or optionally new biological properties. The derivatives also include the modified DNA sequences allowing improved expression in vivo.

In a first embodiment, the present invention relates to a defective recombinant virus comprising a cDNA encoding the ABCC11 polypeptide. In another embodiment of the invention, a defective recombinant virus comprises a genomic DNA (gDNA) encoding the ABCC11 polypeptide. Preferably, the ABCC11 polypeptide comprises an amino acid sequence SEQ ID NO:31, respectively.

The vectors of the invention may be prepared from various types of viruses. Preferably, vectors derived from adenoviruses, adeno-associated viruses (AAV), herpesviruses (HSV) or retroviruses are used. An adenovirus may be used for direct administration or for the ex vivo modification of cells intended to be implanted. A retrovirus may be used for the implantation of producing cells.

The viruses according to the invention are defective, that is to say that they are incapable of autonomously replicating in the target cell. Generally, the genome of the defective viruses used in the context of the present invention therefore lacks at least the sequences necessary for the replication of said virus in the infected cell. These regions may be either eliminated (completely or partially), or made non functional, or substituted with other sequences and in particular with the nucleic sequence encoding the ABCC11 protein. Preferably, the defective virus retains, nevertheless, the sequences of its genome which are necessary for the encapsidation of the viral particles.

As regards more particularly adenoviruses, various serotypes, whose structure and properties vary somewhat, have been characterized. Among these serotypes, human adenoviruses of type 2 or 5 (Ad 2 or Ad 5) or adenoviruses of animal origin (see Application WO 94/26914) may be used in the context of the present invention. Among the adenoviruses of animal origin which can be used in the context of the present invention, there may be mentioned adenoviruses of canine, bovine, murine (example: Mav1, Beard et al., Virology 75 (1990) 81), ovine, porcine, avian or simian (example: SAV) origin. The adenovirus of animal origin may be a canine adenovirus, or, for example, a CAV2 adenovirus [Manhattan or A26/61 strain (ATCC VR-800) for example]. Adenoviruses of human or canine or mixed origin may be used in the context of the invention. The defective adenoviruses of the invention may comprise the ITRs, a sequence allowing the encapsidation and the sequence encoding the ABCC11 protein. In the genome of the adenoviruses of the invention, the E1 region at least may be made non functional. In addition, in the genome of the adenoviruses of the invention, the E1 gene and at least one of the E2, E4 and L1–L5 genes may be non functional. The viral gene considered may be made non functional by any technique known to a person skilled in the art, and in particular by total suppression, by substitution, by partial deletion or by addition of one or more bases in the gene(s) considered. Such modifications may be obtained in vitro (on the isolated DNA) or in situ, for example, by means of genetic engineering techniques, or by treatment by means of mutagenic agents. Other regions may also be modified, and in particular the E3 (WO95/02697), E2 (WO94/28938), E4 (WO94/28152, WO94/12649, WO95/02697) and L5 (WO95/02697) region. According to a some embodiments, the adenovirus according to the invention comprises a deletion in the E1 and E4 regions and the sequence encoding ABCC11 is inserted at the level of the inactivated E1 region. According to further embodiments, it comprises a deletion in the E1 region at the level of which the E4 region and the sequence encoding the ABCC11 protein (French Patent Application FR94 13355) are inserted.

The defective recombinant adenoviruses according to the invention may be prepared by any technique known to persons skilled in the art (Levrero et al., 1991 *Gene* 101; EU patent No. 185 573; and Graham, 1984, EMBO J., 3:2917). In particular, they may be prepared by homologous recombination between an adenovirus and a plasmid carrying, inter alia, the nucleic acid encoding the ABCC11 protein. The homologous recombination occurs after cotransfection of said adenoviruses and plasmid into an appropriate cell line. The cell line used should be (i) be transformable by said elements, and (ii), contain the sequences capable of complementing the part of the defective adenovirus genome, for example, in integrated form in order to avoid the risks of recombination. By way of example of a line, there may be mentioned the human embryonic kidney line 293 (Graham et al., 1977, J. Gen. Virol., 36:59), which contains in particular, integrated into its genome, the left part of the genome of an Ad5 adenovirus (12%) or lines capable of complementing the E1 and E4 functions as described in particular in Applications No. WO 94/26914 and WO95/02697.

As regards the adeno-associated viruses (AAV), they are DNA viruses of a relatively small size, which integrate into the genome of the cells which they infect, in a stable and site-specific manner. They are capable of infecting a broad spectrum of cells, without inducing any effect on cellular growth, morphology or differentiation. Moreover, they do not appear to be involved in pathologies in humans. The genome of AAVs has been cloned, sequenced and characterized. It comprises about 4700 bases, and contains at each end an inverted repeat region (ITR) of about 145 bases, serving as replication origin for the virus. The remainder of the genome is divided into 2 essential regions carrying the encapsidation functions: the left hand part of the genome, which contains the rep gene, involved in the viral replication and the expression of the viral genes; the right hand part of the genome, which contains the cap gene encoding the virus capsid proteins.

The use of vectors derived from AAVs for the transfer of genes in vitro and in vivo has been described in the literature (see in particular WO 91/18088; WO 93/09239; U.S. Pat. Nos. 4,797,368, 5,139,941, EP 488 528). These applications describe various constructs derived from AAVs, in which the rep and/or cap genes are deleted and replaced by a gene of interest, and their use for transferring in vitro (on cells in culture) or in vivo (directly into an organism) said gene of interest. However, none of these documents either describes or suggests the use of a recombinant AAV for the transfer and expression in vivo or ex vivo of the ABCC11 protein, or the advantages of such a transfer. The defective recombinant AAVs according to the invention may be prepared by cotransfection, into a cell line infected with a human helper virus (for example an adenovirus), of a plasmid containing the sequence encoding the ABCC11 protein bordered by two AAV inverted repeat regions (ITR), and of a plasmid carrying the AAV encapsidation genes (rep and cap genes). The recombinant AAVs produced are then purified by conventional techniques.

As regards the herpesviruses and the retroviruses, the construction of recombinant vectors has been widely described in the literature: see in particular Breakfield et al., (1991, New Biologist, 3:203); EP 453242, EP 178220, Bernstein et al. (1985); McCormick, (1985. BioTechnology, 3:689), and the like.

In particular, the retroviruses are integrating viruses, infecting dividing cells. The genome of the retroviruses essentially comprises two long terminal repeats (LTRs), an encapsidation sequence and three coding regions (gag, pol and env). In the recombinant vectors derived from retroviruses, the gag, pol and env genes are generally deleted, completely or partially, and replaced with a heterologous nucleic acid sequence of interest. These vectors may be produced from various types of retroviruses such as in particular MoMuLV ("murine moloney leukemia virus"; also called MoMLV), MSV ("murine moloney sarcoma virus"), HaSV ("harvey sarcoma virus"); SNV ("spleen necrosis virus"); RSV ("rous sarcoma virus") or Friend's virus.

To construct recombinant retroviruses containing a sequence encoding the ABCC11 protein according to the invention, a plasmid containing in particular the LTRs, the encapsidation sequence and said coding sequence is generally constructed, and then used to transfect a so-called encapsidation cell line, capable of providing in trans the retroviral functions deficient in the plasmid. Generally, the encapsidation lines are therefore capable of expressing the gag, pol and env genes. Such encapsidation lines have been described in the prior art, and in particular the PA317 line (U.S. Pat. No. 4,861,719), the PsiCRIP line (WO 90/02806) and the GP+envAm-12 line (WO 89/07150). Moreover, the recombinant retroviruses may contain modifications at the level of the LTRs in order to suppress the transcriptional activity, as well as extended encapsidation sequences, containing a portion of the gag gene (Bender et al., 1987, J Virol., 61:1639). The recombinant retroviruses produced are then purified by conventional techniques.

To carry out the present invention, a defective recombinant adenovirus may be used. The particularly advantageous properties of adenoviruses may be used for the in vivo expression of a protein having a lipophilic subtrate transport activity. The adenoviral vectors according to the invention may be used for a direct administration in vivo of a purified suspension, or for the ex vivo transformation of cells, in particular autologous cells, in view of their implantation. Furthermore, the adenoviral vectors according to the invention exhibit, in addition, considerable advantages, such as in particular their very high infection efficiency, which makes it possible to carry out infections using small volumes of viral suspension.

According to some embodiments of the invention, a line producing retroviral vectors containing the sequence encoding the ABCC11 protein is used for implantation in vivo. The lines which can be used to this end are in particular the PA317 (U.S. Pat. No. 4,861,719), PsiCrip (WO 90/02806) and GP+envAm-12 (U.S. Pat. No. 5,278,056) cells modified so as to allow the production of a retrovirus containing a nucleic sequence encoding any one of ABCC11 and ABCC12 proteins according to the invention. For example, totipotent stem cells, precursors of blood cell lines, may be collected and isolated from a subject. These cells, when cultured, may then be transfected with the retroviral vector containing the sequence encoding the ABCC11 protein under the control of viral, nonviral or nonviral promoters specific for macrophages or under the control of its own promoter. These cells are then reintroduced into the subject. The differentiation of these cells will be responsible for blood cells expressing the ABCC11 protein.

In the vectors of the invention, the sequence encoding the ABCC11 protein may be placed under the control of signals allowing its expression in the infected cells. These may be expression signals which are homologous or heterologous, that is to say signals different from those which are naturally responsible for the expression of the ABCC11 protein. They may also be in particular sequences responsible for the expression of other proteins, or synthetic sequences. In particular, they may be sequences of eukaryotic or viral genes or derived sequences, stimulating or repressing the transcription of a gene in a specific manner or otherwise and in an inducible manner or otherwise. By way of example, they may be promoter sequences derived from the genome of the cell which it is desired to infect, or from the genome of a virus, and in particular the promoters of the E1A or major late promoter (MLP) genes of adenoviruses, the cytomegalovirus (CMV) promoter, the RSV-LTR and the like. Among the eukaryotic promoters, there may also be mentioned the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), tissue-specific promoters (pyruvate kinase, villin, promoter of the fatty acid binding intestinal protein, promoter of the smooth muscle cell α-actin, promoters specific for the liver; Apo AI, Apo AII, human albumin and the like) or promoters corresponding to a stimulus (steroid hormone receptor, retinoic acid receptor and the like). In addition, these expression sequences may be modified by addition of enhancer or regulatory sequences and the like. Moreover, when the inserted gene does not contain expression sequences, it may be inserted into the genome of the defective virus downstream of such a sequence.

In a specific embodiment, the invention relates to a defective recombinant virus comprising a nucleic acid encoding the ABCC11 protein the control of a promoter chosen from RSV-LTR or the CMV early promoter.

As indicated above, the present invention also relates to any use of a virus as described above for the preparation of a pharmaceutical composition for the treatment and/or prevention of pathologies linked to the transport of lipophilic substances.

The present invention also relates to a pharmaceutical composition comprising one or more defective recombinant viruses as described above. These pharmaceutical compositions may be formulated for administration by the topical, oral, parenteral, intranasal, intravenous, intramuscular, subcutaneous, intraocular or transdermal route and the like. The pharmaceutical compositions of the invention may comprise a pharmaceutically acceptable vehicle or physiologically compatible excipient for an injectable formulation, in particular for an intravenous injection, such as for example into the patient's portal vein. These may relate in particular to isotonic sterile solutions or dry, in particular, freeze-dried, compositions which, upon addition depending on the case of sterilized water or physiological saline, allow the preparation of injectable solutions. Direct injection into the patient's portal vein may be performed because it makes it possible to target the infection at the level of the liver and thus to concentrate the therapeutic effect at the level of this organ.

The doses of defective recombinant virus used for the injection may be adjusted as a function of various parameters, and in particular as a function of the viral vector, of the mode of administration used, of the relevant pathology or of the desired duration of treatment. In general, the recombinant adenoviruses according to the invention are formulated and administered in the form of doses of between $10^4$ and $10^{14}$ pfu/ml, such as $10^6$ to $10^{10}$ pfu/ml. The term "pfu" (plaque forming unit) corresponds to the infectivity of a virus solution, and is determined by infecting an appropriate cell culture and measuring, generally after 48 hours, the number of plaques that result from infected cell lysis. The techniques for determining the pfu titer of a viral solution are well documented in the literature.

As regards retroviruses, the compositions according to the invention may directly contain the producing cells, with a view to their implantation.

In this regard, another subject of the invention relates to any mammalian cell infected with one or more defective recombinant viruses according to the invention. More particularly, the invention relates to any population of human cells infected with such viruses. These may be in particular cells of blood origin (totipotent stem cells or precursors), fibroblasts, myoblasts, hepatocytes, keratinocytes, smooth muscle and endothelial cells, glial cells and the like.

The cells according to the invention may be derived from primary cultures. These may be collected by any technique known to persons skilled in the art and then cultured under conditions allowing their proliferation. As regards more particularly fibroblasts, these may be easily obtained from biopsies, for example according to the technique described by Ham (1980). These cells may be used directly for infection with the viruses, or stored, for example by freezing, for the establishment of autologous libraries, in view of a subsequent use. The cells according to the invention may be secondary cultures, obtained for example from pre-established libraries (see for example EP 228458, EP 289034, EP 400047, EP 456640).

The cells in culture are then infected with a recombinant virus according to the invention, in order to confer on them the capacity to produce a biologically active ABCC11 protein. The infection is carried out in vitro according to techniques known to persons skilled in the art. In particular, depending on the type of cells used and the desired number of copies of virus per cell, persons skilled in the art can adjust the multiplicity of infection and optionally the number of infectious cycles produced. It is clearly understood that these steps must be carried out under appropriate conditions of sterility when the cells are intended for administration in vivo. The doses of recombinant virus used for the infection of the cells may be adjusted by persons skilled in the art according to the desired aim. The conditions described above for the administration in vivo may be applied to the infection in vitro. For the infection with a retrovirus, it is also possible to co-culture a cell to be infected with a cell producing the recombinant retrovirus according to the invention. This makes it possible to eliminate purification of the retrovirus.

Another subject of the invention relates to an implant comprising mammalian cells infected with one or more defective recombinant viruses according to the invention or cells producing recombinant viruses, and an extracellular matrix. The implants according to the invention may comprise $10^5$ to $10^{10}$ cells, for example $10^6$ to $10^8$ cells.

More particularly, in the implants of the invention, the extracellular matrix comprises a gelling compound and optionally a support allowing the anchorage of the cells.

For the preparation of the implants according to the invention, various types of gelling agents may be used. The gelling agents are used for the inclusion of the cells in a matrix having the constitution of a gel, and for promoting the anchorage of the cells on the support, where appropriate. Various cell adhesion agents can therefore be used as gelling agents, such as in particular collagen, gelatin, glycosaminoglycans, fibronectin, lectins and the like. Collagen may be used in the context of the present invention. This may be collagen of human, bovine or murine origin. In addition, type I collagen may be used.

As indicated above, the compositions according to the invention may comprise a support allowing the anchorage of the cells. The term anchorage designates any form of biological and/or chemical and/or physical interaction causing the adhesion and/or the attachment of the cells to the support. Moreover, the cells may either cover the support used, or penetrate inside this support, or both. In the context of the invention a solid, nontoxic and/or biocompatible support may be used. For example, it is possible to use polytetrafluoroethylene (PTFE) fibers or a support of biological origin.

The present invention thus offers a very effective means for the treatment or prevention of pathologies linked to the transport of lipophilic substances.

In addition, this treatment may be applied to both humans and any animals such as ovines, bovines, domestic animals (dogs, cats and the like), horses, fish and the like.

Recombinant Host Cells

The invention relates to a recombinant host cell comprising a nucleic acid of the invention, and more particularly, a nucleic acid comprising a nucleotide sequence selected from SEQ ID NOS:1–30, or a complementary nucleotide sequence thereof.

The invention also relates to a recombinant host cell comprising a nucleic acid of the invention, and more particularly a nucleic acid comprising a nucleotide sequence as depicted in SEQ ID NOS:1–30, or a complementary nucleotide sequence thereof.

According to another aspect, the invention also relates to a recombinant host cell comprising a recombinant vector according to the invention. Therefore, the invention also relates to a recombinant host cell comprising a recombinant vector comprising any of the nucleic acids of the invention, and more particularly a nucleic acid comprising a nucleotide sequence of selected from SEQ ID NOS:1–30, or a complementary nucleotide sequence thereof.

The invention also relates to a recombinant host cell comprising a recombinant vector comprising a nucleic acid comprising a nucleotide sequence as depicted in any one of SEQ ID NOS:1–30, or of a complementary nucleotide sequence thereof.

Example host cells according to the invention include the following:
a) prokaryotic host cells: strains of *Escherichia coli* (strain DH5-α); of *Bacillus subtilis,* of *Salmonella typhimurium,* or species of genera such as *Pseudomonas, Streptomyces* and *Staphyloccocus;*
b) eukaryotic host cells: HeLa cells (ATCC No. CCL2), Cv 1 cells (ATCC No. CCL70), COS cells (ATCC No. CRL 1650), Sf-9 cells (ATCC No. CRL 1711), CHO cells (ATCC No. CCL-61) 3T3 cells (ATCC No. CRL-6361) or human Erythroleukemia K562 (ATCC N° CCL-243).

Methods for Producing ABCC11 Polypeptide

The invention also relates to a method for the production of a polypeptide comprising an amino acid sequence SEQ ID NO:31, said method comprising the steps of:
a) inserting a nucleic acid encoding said polypeptide into an appropriate vector;
b) culturing, in an appropriate culture medium, a previously transformed host cell or transfecting a host cell with the recombinant vector of step a);
c) recovering the conditioned culture medium or lysing the host cell, for example by sonication or by osmotic shock;
d) separating and purifying said polypeptide from said culture medium or alternatively from the cell lysates obtained in step c); and
e) where appropriate, characterizing the recombinant polypeptide produced.

The polypeptides according to the invention may be characterized by binding to an immunoaffinity chromatography column on which the antibodies directed against this polypeptide or against a fragment or a variant thereof have been previously immobilized.

According to another aspect, a recombinant polypeptide according to the invention may be purified by passing it over an appropriate series of chromatography columns, according to methods known to persons skilled in the art and described for example in F. Ausubel et al (1989, Current Protocols in Molecular Biology, Green Publishing Associates and Wiley Interscience, N.Y).

A polypeptide according to the invention may also be prepared by conventional chemical synthesis techniques either in homogeneous solution or in solid phase. By way of illustration, a polypeptide according to the invention may be prepared by the technique either in homogeneous solution described by Houben Weyl (1974, Meuthode der Organischen Chemie, E. Wunsch Ed., 15-I: 15-II) or the solid phase synthesis technique described by Merrifield (1965, *Nature,* 207(996):522–523; 1965, *Science,* 150(693):178–185).

A polypeptide termed "homologous" to a polypeptide having an amino acid sequence selected from SEQ ID NO:31 also forms part of the invention. Such a homologous polypeptide comprises an amino acid sequence possessing one or more substitutions of an amino acid by an equivalent amino acid of SEQ ID NO:30.

An "equivalent amino acid" according to the present invention will be understood to mean for example replacement of a residue in the L form by a residue in the D form or the replacement of a glutamic acid (E) by a pyro-glutamic acid according to techniques well known to persons skilled in the art. By way of illustration, the synthesis of peptide containing at least one residue in the D form is described by Koch (1977). According to another aspect, two amino acids belonging to the same class, that is to say two uncharged polar, nonpolar, basic or acidic amino acids, are also considered as equivalent amino acids.

Polypeptides comprising at least one nonpeptide bond such as a retro-inverse bond (NHCO), a carba bond ($CH_2CH_2$) or a ketomethylene bond (CO—$CH_2$) also form part of the invention.

The polypeptides according to the invention may comprise one or more additions, deletions, and substitutions of at least one amino acid and will retain their capacity to be recognized by antibodies directed against the nonmodified polypeptides.

Antibodies

The ABCC11 polypeptide according to the invention, in particular 1) a polypeptide comprising an amino acid sequence of any one of SEQ ID NO:31, 2) a polypeptide fragment or variant of a polypeptide comprising an amino acid sequence of any one of SEQ ID NO:30, or 3) a polypeptide termed "homologous" to a polypeptide comprising amino acid sequence selected from SEQ ID NO:31, may be used for the preparation of an antibody, in particular for detecting the production of a normal or altered form of ABCC11 polypeptide in a patient.

An antibody directed against a polypeptide termed "homologous" to a polypeptide having an amino acid sequence selected from SEQ ID NO:31 also forms part of the invention. Such an antibody is directed against a homologous polypeptide comprising an amino acid sequence possessing one or more substitutions of an amino acid by an equivalent amino acid of SEQ ID NO:31.

"Antibody" for the purposes of the present invention will be understood to mean in particular polyclonal or monoclonal antibodies or fragments (for example the F(ab)'$_2$ and Fab fragments) or any polypeptide comprising a domain of the initial antibody recognizing the target polypeptide or polypeptide fragment according to the invention.

Monoclonal antibodies may be prepared from hybridomas according to the technique described by Kohler and Milstein (1975, *Nature*, 256:495–497).

According to the invention, a polypeptide produced recombinantly or by chemical synthesis, and fragments or other derivatives or analogs thereof, including fusion proteins, may be used as an immunogen to generate antibodies that recognize a polypeptide according to the invention. Such antibodies include but are not limited to polyclonal, monoclonal, chimeric, single chain, Fab fragments, and an Fab expression library. The anti-ABCC5, anti-ABCC4, or anti-ABCC1 antibodies of the invention maybe cross reactive, e.g., they may recognize corresponding ABCC11 polypeptide from different species. Polyclonal antibodies have greater likelihood of cross reactivity. Alternatively, an antibody of the invention may be specific for a single form of ABCC11. Such an antibody may be specific for human ABCC11.

Various procedures known in the art may be used for the production of polyclonal antibodies to the ABCC11 polypeptide or derivative or analog thereof. For the production of antibody, various host animals can be immunized by injection with the ABCC11 polypeptide, or a derivatives (e.g., fragment or fusion protein) thereof, including but not limited to rabbits, mice, rats, sheep, goats, etc. In one embodiment, the ABCC11 polypeptide or a fragment thereof can be conjugated to an immunogenic carrier, e.g. bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the ABCC11 polypeptide, or a fragment, analog, or derivative thereof, any technique that provides for the production of antibody molecules by continuous cell lines in culture may be used. These include but are not limited to the hybridoma technique originally developed by Kohler and Milstein (1975, *Nature*, 256:495–497), as well as the trioma technique, the human B-cell hybridoma technique (Kozbor et al., 1983, *Immunology Today*, 4:72; Cote et al., 1983, *Proc. Natl. Acad. Sci. U.S.A.*, 80:2026–2030), and the EBV-hybridoma technique to produce human monoclonal antibodies (Cole et al., 1985, In: *Monoclonal Antibodies and Cancer Therapy*, Alan R. Liss, Inc., pp. 77–96). In an additional embodiment of the invention, monoclonal antibodies can be produced in germ-free animals (WO 89/12690). In fact, according to the invention, techniques developed for the production of "chimeric antibodies" (Morrison et al., 1984, *J. Bacteriol*. 159:870; Neuberger et al., 1984, *Nature*, 312:604–608; Takeda et al., 1985, *Nature* 314:452–454) by splicing the genes from a mouse antibody molecule specific for the ABCC11 polypeptide together with genes from a human antibody molecule of appropriate biological activity can be used; such antibodies are within the scope of this invention. Such human or humanized chimeric antibodies may be used in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476,786 and 5,132,405 to Huston; U.S. Pat. No. 4,946,778) can be adapted to produce ABCC11 polypeptide-specific single chain antibodies. An additional embodiment of the invention utilizes the techniques described for the construction of Fab expression libraries (Huse et al., 1989, *Science* 246:1275–1281) to allow rapid and easy identification of monoclonal Fab fragments with the desired specificity for the ABCC11 polypeptide, or its derivative, or analog.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention. For example, to select antibodies which recognize a specific epitope of the ABCC11 polypeptide, one may assay generated hybridomas for a product which binds to the ABCC11 polypeptide fragment containing such epitope. For selection of an antibody specific to the ABCC11 polypeptide from a particular species of animal, one can select on the basis of positive binding with the ABCC11 polypeptide expressed by or isolated from cells of that species of animal.

The foregoing antibodies can be used in methods known in the art relating to the localization and activity of the ABCC11 polypeptide, e.g., for Western blotting, ABCC11 polypeptide in situ, measuring levels thereof in appropriate physiological samples, etc. using any of the detection techniques mentioned above or known in the art.

In a specific embodiment, antibodies that agonize or antagonize the activity of the ABCC11 polypeptide can be generated. Such antibodies can be tested using the assays described infra for identifying ligands.

The present invention relates to an antibody directed against 1) a polypeptide comprising an amino acid sequence of the SEQ ID NO:31; 2) a polypeptide fragment or variant of a polypeptide comprising an amino acid sequence of the SEQ ID NO:31, or 3) a polypeptide termed "homologous" to a polypeptide comprising amino acid sequence selected from SEQ ID NO:31, also forms part of the invention, as produced in the trioma technique or the hybridoma technique described by Kozbor et al. (1983, *Hybridoma*, 2(1):7–16).

The invention also relates to single-chain Fv antibody fragments (ScFv) as described in U.S. Pat. No. 4,946,778 or by Martineau et al. (1998, *J Mol Biol*, 280(1):117–127).

The antibodies according to the invention also comprise antibody fragments obtained with the aid of phage libraries as described by Ridder et al., (1995, *Biotechnology* (NY), 13(3):255–260) or humanized antibodies as described by Reinmann et al. (1997, *AIDS Res Hum Retroviruses*, 13(11) :933–943) and Leger et al., (1997, *Hum Antibodies*, 8(1) :3–16)

The antibody preparations according to the invention are useful in immunological detection tests intended for the identification of the presence and/or of the quantity of antigens present in a sample.

An antibody according to the invention may comprise, in addition, a detectable marker which is isotopic or nonisotopic, for example fluorescent, or may be coupled to a molecule such as biotin, according to techniques well known to persons skilled in the art.

Thus, the subject of the invention is, in addition, a method of detecting the presence of a polypeptide according to the invention in a sample, said method comprising the steps of:
  a) bringing the sample to be tested into contact with an antibody directed against
    1) a polypeptide comprising an amino acid sequence of the SEQ ID NO:31,
    2) a polypeptide fragment or variant of a polypeptide comprising an amino acid sequence of the SEQ ID NO:31, or
    3) a polypeptide termed "homologous" to a polypeptide comprising amino acid sequence of SEQ ID NO:31, and
  b) detecting the antigen/antibody complex formed.

The invention also relates to a box or kit for diagnosis or for detecting the presence of a polypeptide in accordance with the invention in a sample, said box comprising:
  a) an antibody directed against 1) a polypeptide comprising an amino acid sequence of SEQ ID NO:31, 2) a polypeptide fragment or variant of a polypeptide comprising an amino acid sequence of the SEQ ID NO:31, or 3) a polypeptide termed "homologous" to a polypeptide comprising amino acid sequence of SEQ ID NO:31, and
  b) a reagent allowing the detection of the antigen/antibody complexes formed.

Pharmaceutical Compositions and Therapeutic Methods of Treatment

The invention also relates to pharmaceutical compositions intended for the prevention and/or treatment of a deficiency in the transport of cholesterol or inflammatory lipid substances, characterized in that they comprise a therapeutically effective quantity of a polynucleotide capable of giving rise to the production of an effective quantity of the ABCC11 functional polypeptide, in particular a polypeptide comprising an amino acid sequence of SEQ ID NO:31.

The invention also provides pharmaceutical compositions comprising a nucleic acid encoding any one of ABCC11 polypeptide according to the invention and pharmaceutical compositions comprising the ABCC11 polypeptide according to the invention intended for the prevention and/or treatment of diseases which are mapped on the chromosome locus 16q12.

The present invention also relates to a new therapeutic approach for the treatment of pathologies linked to the transport of lipophilic substances, comprising transferring and expressing in vivo nucleic acids encoding the ABCC11 protein according to the invention.

Thus, the present invention offers a new approach for the treatment and/or the prevention of pathologies such as the paroxysmal kinesigenic choreoathetosis.

Consequently, the invention also relates to a pharmaceutical composition intended for the prevention of or treatment of subjects affected by a dysfunction of the transport of anionic drugs, such as methotrexate (MTX), neutral drugs conjugated to acidic ligands, such as GSH conjugated drugs, glucuronate, or sulfate, comprising a nucleic acid encoding at the ABCC11 protein in combination with one or more physiologically compatible vehicle and/or excipient.

According to a specific embodiment of the invention, a composition is provided for the in vivo production of the ABCC11 protein. This composition comprises a nucleic acid encoding the ABCC11 polypeptide placed under the control of appropriate regulatory sequences, in solution in a physiologically acceptable vehicle and/or excipient.

Therefore, the present invention also relates to a composition comprising a nucleic acid encoding a polypeptide comprising an amino acid sequence of SEQ ID NO:31, wherein the nucleic acid is placed under the control of appropriate regulatory elements.

Such a composition may comprise a nucleic acid comprising a nucleotide sequence of SEQ ID NO:1, placed under the control of appropriate regulatory elements.

According to another aspect, the subject of the invention is also a preventive and/or curative therapeutic method of treating diseases caused by a deficiency in the transport of lipophilic substances, such a method comprising a step in which there is administered to a patient a nucleic acid encoding the ABCC11 polypeptide according to the invention in said patient, said nucleic acid being, where appropriate, combined with one or more physiologically compatible vehicles and/or excipients.

The invention also relates to a pharmaceutical composition intended for the prevention of or treatment of subjects affected by, a deficiency of the ABCC11 gene, comprising a recombinant vector according to the invention, in combination with one or more physiologically compatible excipients.

According to a specific embodiment, a method of introducing a nucleic acid according to the invention into a host cell, in particular a host cell obtained from a mammal, in vivo, comprises a step during which a preparation comprising a pharmaceutically compatible vector and a "naked" nucleic acid according to the invention, placed under the control of appropriate regulatory sequences, is introduced by local injection at the level of the chosen tissue, for example a smooth muscle tissue, the "naked" nucleic acid being absorbed by the cells of this tissue.

The invention also relates to the use of a nucleic acid according to the invention, encoding the ABCC11 protein, for the manufacture of a medicament intended for the prevention and/or treatment in various forms or more particularly for the treatment of subjects affected by a paroxysmal kinesigenic choreoathetosis.

The invention also relates to the use of a recombinant vector according to the invention, comprising a nucleic acid encoding the ABCC11 protein, for the manufacture of a medicament intended for the prevention and/or treatment of subjects affected by a paroxysmal kinesigenic choreoathetosis.

The invention also relates to the use of a nucleic acid according to the invention, encoding the ABCC11 protein, for the manufacture of a medicament intended for the prevention and/or treatment in various forms or more particularly for the treatment of subjects affected by a a deficiency in the transport of anionic drugs, such as methotrexate (MTX), neutral drugs conjugated to acidic ligands, such as GSH conjugated drugs, glucuronate, or sulfate.

The invention also relates to the use of a recombinant vector according to the invention, comprising a nucleic acid encoding the ABCC11 protein, for the manufacture of a medicament intended for the prevention and/or treatment of a deficiency in the transport of anionic drugs, such as methotrexate (MTX), neutral drugs conjugated to acidic ligands, such as GSH conjugated drugs, glucuronate, or sulfate.

As indicated above, the present invention also relates to the use of a defective recombinant virus according to the invention for the preparation of a pharmaceutical composition for the treatment and/or prevention of pathologies linked to the paroxysmal kinesigenic choreoathetosis.

The invention relates to the use of such a defective recombinant virus for the preparation of a pharmaceutical composition intended for the treatment and/or prevention of a deficiency associated with the transport of anionic drugs, such as methotrexate (MTX), neutral drugs conjugated to acidic ligands, such as GSH conjugated drugs, glucuronate, or sulfate. Thus, the present invention also relates to a pharmaceutical composition comprising one or more defective recombinant viruses according to the invention.

The present invention also relates to the use of cells genetically modified ex vivo with a virus according to the invention, or of producing cells such as viruses, implanted in the body, allowing a prolonged and effective expression in vivo of a biologically active ABCC11 protein.

The present invention shows that it is possible to incorporate a nucleic acid encoding the ABCC11 polypeptide into a viral vector, and that these vectors make it possible to effectively express a biologically active, mature form. More particularly, the invention shows that the in vivo expression of the ABCC11 gene may be obtained by direct administration of an adenovirus or by implantation of a producing cell or of a cell genetically modified by an adenovirus or by a retrovirus incorporating such a DNA.

The pharmaceutical compositions of the invention may comprise a pharmaceutically acceptable vehicle or physiologically compatible excipient for an injectable formulation, in particular for an intravenous injection, such as for example into the patient's portal vein. These may relate in particular to isotonic sterile solutions or dry, in particular, freeze-dried, compositions which, upon addition depending on the case of sterilized water or physiological saline, allow the preparation of injectable solutions. Direct injection into the patient's portal vein may be performed because it makes it possible to target the infection at the level of the liver and thus to concentrate the therapeutic effect at the level of this organ.

A "pharmaceutically acceptable vehicle or excipient" includes diluents and fillers which are pharmaceutically acceptable for method of administration, are sterile, and may be aqueous or oleaginous suspensions formulated using suitable dispersing or wetting agents and suspending agents. The particular pharmaceutically acceptable carrier and the ratio of active compound to carrier are determined by the solubility and chemical properties of the composition, the particular mode of administration, and standard pharmaceutical practice.

Any nucleic acid, polypeptide, vector, or host cell of the invention may be introduced in vivo in a pharmaceutically acceptable vehicle or excipient. The phrase "pharmaceutically acceptable" refers to molecular entities and compositions that are physiologically tolerable and do not typically produce an allergic or similar untoward reaction, such as gastric upset, dizziness and the like, when administered to a human. As used herein, the term "pharmaceutically acceptable" generally means approved by a regulatory agency of the Federal or a state government or listed in the U.S. Pharmacopeia or other generally recognized pharmacopeia for use in animals, and more particularly in humans. The term "excipient" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions may be employed as excipients, particularly for injectable solutions. Suitable pharmaceutical excipients are described in "Remington's Pharmaceutical Sciences" by E. W. Martin.

The pharmaceutical compositions according to the invention may be equally well administered by the oral, rectal, parenteral, intravenous, subcutaneous or intradermal route.

According to another aspect, the subject of the invention is also a preventive and/or curative therapeutic method of treating diseases caused by a deficiency in the transport of cholesterol or inflammatory lipid substances, comprising administering to a patient or subject a nucleic acid encoding the ABCC11 polypeptide, said nucleic acid being combined with one or more physiologically compatible vehicles and/or excipients.

In another embodiment, the nucleic acid, recombinant vectors, and compositions according to the invention can be delivered in a vesicle, in particular a liposome (see Langer, 1990, Science, 249:1527–1533; Treat et al., 1989, *Liposomes in the Therapy of Infectious Disease and Cancer,* Lopez-Berestein and Fidler (eds.), Liss: New York, pp. 353–365; and Lopez-Berestein, 1989, In: *Liposomes in the Therapy of Infectious Disease and Cancer,* Lopez-Berestein and Fidler (eds.), Liss: New York, pp. 317–327).

In a further aspect, recombinant cells that have been transformed with a nucleic acid according to the invention and that express high levels of the ABCC11 polypeptide according to the invention can be transplanted in a subject in need of the ABCC11 polypeptide. Autologous cells transformed with the ABCC11 encoding nucleic acid according to the invention may be transplanted to avoid rejection; alternatively, technology is available to shield non-autologous cells that produce soluble factors within a polymer matrix that prevents immune recognition and rejection.

A subject in whom administration of the nucleic acids, polypeptides, recombinant vectors, recombinant host cells, and compositions according to the invention is performed can be any animal, such as a human, or a domestic mammal, such as a dog or cat, or a livestock mammal, or a laboratory animal, such as a mouse. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

A pharmaceutical composition comprising a nucleic acid, a recombinant vector, or a recombinant host cell, as defined above, may be administered to the patient or subject.

Methods of Screening an Agonist or Antagonist Compound for the ABCC11 Polypeptide According to another aspect, the invention also relates to various methods of screening compounds or small molecules for therapeutic use which are useful in the treatment of diseases due to a deficiency in the transport of cholesterol or inflammatory lipid substances.

The invention therefore also relates to the use of the ABCC11 polypeptide, or of cells expressing the ABCC11 polypeptide, for screening active ingredients for the prevention and/or treatment of diseases resulting from a dysfunction in the ABCC11 gene. The catalytic sites and oligopeptide or immunogenic fragments of the ABCC11 polypeptide can serve for screening product libraries by a whole range of existing techniques. The polypeptide fragment used in this type of screening may be free in solution, bound to a solid support, at the cell surface or in the cell. The formation of the binding complexes between the ABCC11 polypeptide fragment and the tested agent can then be measured.

Another product screening technique which may be used in high-flux screenings giving access to products having affinity for the protein of interest is described in application WO84/03564. In this method, applied to the ABCC11 protein, various products are synthesized on a solid surface. These products react with the corresponding ABCC11 protein or fragment thereof and the complex is washed. The products binding the ABCC11 protein are then detected by methods known to persons skilled in the art. Non-neutralizing antibodies can also be used to capture a peptide and immobilize it on a support.

Another possibility is to perform a product screening method using the ABCC11 neutralizing competition antibodies, ABCC11 protein and a product potentially binding the ABCC11 protein. In this manner, the antibodies may be used to detect the presence of a peptide having a common antigenic unit with the ABCC11 polypeptide or protein.

Of the products to be evaluated for their ability to increase activity of ABCC11, there may be mentioned in particular kinase-specific ATP homologs involved in the activation of the molecules, as well as phosphatases, which may be able to avoid the dephosphorylation resulting from said kinases. There may be mentioned in particular inhibitors of the phosphodiesterase (PDE) theophylline and 3-isobutyl-1-methylxanthine type or the adenylcyclase forskolin activators.

Accordingly, this invention relates to the use of any method of screening products, i.e., compounds, small molecules, and the like, based on the method of translocation of cholesterol or lipophilic substances between the membranes or vesicles, this being in all synthetic or cellular types, that is to say of mammals, insects, bacteria, or yeasts expressing constitutively or having incorporated human ABCC11 encoding nucleic acid. To this effect, labeled lipophilic substances analogs may be used.

Furthermore, knowing that the disruption of numerous transporters have been described (van den Hazel et al., 1999, *J. Biol Chem*, 274: 1934–41), it is possible to think of using cellular mutants having a characteristic phenotype and to complement the function thereof with the ABCC11 protein and to use the whole for screening purposes.

The invention also relates to a method of screening a compound or small molecule active on the transport of a substrate, an agonist or antagonist of the ABCC11 polypeptide, said method comprising the following steps:
  a) preparing a membrane vesicle comprising the ABCC11 polypeptide and the substrate comprising a detectable marker;
  b) incubating the vesicle obtained in step a) with an agonist or antagonist candidate compound;
  c) qualitatively and/or quantitatively measuring release of the substrate comprising a detectable marker; and
  d) comparing the release measurement obtained in step b) with a measurement of release of labeled substrate by a vesicle that has not been previously incubated with the agonist or antagonist candidate compound.

ABCC11 polypeptide comprise an amino acid sequence of SEQ ID NO:31.

According to a first aspect of the above screening method, the membrane vesicle is a synthetic lipid vesicle, which may be prepared according to techniques well known to a person skilled in the art. According to this particular aspect, the ABCC11 protein may be recombinant proteins.

According to a second aspect, the membrane vesicle is a vesicle of a plasma membrane derived from cells expressing at least one of ABCC11 polypeptide. These may be cells naturally expressing the ABCC11 polypeptide or cells transfected with a nucleic acid encoding at least one ABCC11 polypeptide or recombinant vector comprising a nucleic acid encoding the ABCC11 polypeptide.

According to a third aspect of the above screening method, the substrate is an anionic drug, such as the methotrexate (MTX).

According to a fourth aspect of the above screening method, the substrate is a neutral drug conjugated to acidic ligands such as GSH, glucuronate, or sulfate conjugated drugs.

According to a fifth aspect, the substrate is radioactively labelled, for example with an isotope chosen from $^3$H or $^{125}$I.

According to a sixth aspect, the substrate is labelled with a fluorescent compound, such as NBD or pyrene.

According to a seventh aspect, the membrane vesicle comprising the labelled substrates and the ABCC11 polypeptide is immobilized at the surface of a solid support prior to step b).

According to a eighth aspect, the measurement of the fluorescence or of the radioactivity released by the vesicle is the direct reflection of the activity of the substrate transport by the ABCC11 polypeptide.

The invention also relates to a method of screening a compound or small molecule active on the transport of anion, an agonist or antagonist of the ABCC11 polypeptide, said method comprising the following steps:
  a) obtaining cells, for example a cell line, that, either naturally or after transfecting the cell with the ABCC11 encoding nucleic acid, expresses the ABCC11 polypeptide;
  b) incubating the cells of step a) in the presence of an anion labelled with a detectable marker;
  c) washing the cells of step b) in order to remove the excess of the labelled anion which has not penetrated into these cells;
  d) incubating the cells obtained in step c) with an agonist or antagonist candidate compound for the ABCC11 polypeptide;
  e) measuring efflux of the labelled anion; and
  f) comparing the value of efflux of the labelled anion determined in step e) with a value of the efflux of a labelled anion measured with cells that have not been previously incubated in the presence of the agonist or antagonist candidate compound of ABCC11 polypeptide.

In a first specific embodiment, the ABCC11 polypeptide comprises an amino acid sequence of SEQ ID NO:31.

According to a second aspect, the cells used in the screening method described above may be cells not naturally expressing, or alternatively expressing at a low level, the ABCC11 polypeptide, said cells being transfected with a recombinant vector according to the invention capable of directing the expression of a nucleic acid encoding the ABCC11 polypeptide.

According to a third aspect, the cells may be cells having a natural deficiency in anion transport, or cells pretreated with one or more anion channel inhibitors such as Verapamil™ or tetraethylammonium.

According to a fourth aspect of said screening method, the anion is a radioactively labelled iodide, such as the salts $K^{125}I$ or $Na^{125}I$.

According to a fifth aspect, the measurement of efflux of the labelled anion is determined periodically over time during the experiment, thus making it possible to also establish a kinetic measurement of this efflux.

According to a sixth aspect, the value of efflux of the labelled anion is determined by measuring the quantity of labelled anion present at a given time in the cell culture supernatant.

According to a seventh aspect, the value of efflux of the labelled anion is determined as the proportion of radioactivity found in the cell culture supernatant relative to the total radioactivity corresponding to the sum of the radioactivity found in the cell lysate and the radioactivity found in the cell culture supernatant in the presence of a compound stimulating the production of interleukine and of an agonist or antagonist candidate compound.

The following examples are intended to further illustrate the present invention but do not limit the invention.

EXAMPLES

Example 1

Search of Human ABCC11 Gene in Genomic Database

Searches of the GeneBank HTGS database were performed with the TBLASTN and TBLASTP programs with the known ABC transporter nucleotide and protein sequences as queries. Amino acid alignments were generated with the PILEUP program included in the Genetics Computer Group (GCG) Package. The GRAIL and GeneScan programs on Genome analysis pipeline I were utilized to predict genomic structures of the new genes.

The human ABCC11 transporter gene sequence was detected on the bacterial artificial chromosome (BAC) clone #AC007600 from the GenBank HTGS database. cDNA sequencing, genomic structure prediction programs, and computer searches determined the sequence and genomic structure of the new gene belonging to the ABCC subfamily.

Primers were designed from expressed sequence tag (EST) clone sequences and from predicted cDNA sequences from 5' and 3' regions of genes. ABCC11 cDNA sequence was confirmed by PCR amplification of testis or liver cDNA (Clontech). Sequencing was performed on the ABI 377 sequencer according to the manufacturer's protocols (Perkin Elmer). Positions of introns were determined by comparison between genomic (BAC AC007600) and cDNA sequences.

Example 2

Radiation Hybrid Mapping (FIG. 2)

The chromosomal localization of the human ABCC11 gene was determined by mapping on the GeneBridge4 radiation hybrid panel (Research Genetics), according to the manufacturer's protocol.

Radiation hybrid mapping placed ABCC11to the centromeric region of human chromosome 16, flanked by markers D16S3093 and D16S409 (FIG. 2). The region encompasses 5.4 cM, or 132.5 cR, and could not be narrowed down further due to the lack of recombination and/or mapped polymorphic markers in this region. The ABCC11 gene most likely localized on chromosome 16q12.1, since it maps closer to the 16 q marker D16S409 (13.24 cR) than the 16 p marker D16S3093 (119.40 cR) (FIG. 2). The ABCC12 was located at the same locus, separated by about 200 kb from ABCC11. ABCC11 and ABCC12 are located tandemly with their 5' ends facing towards the centromere. Two more ABCC subfamily genes, ABCC1 and ABCC6, have been mapped to the short arm of the same chromosome, to 16p13.1 (Cole et al. (1992) Science 258, 1650–1654; Allikmets et al. (1996) Human Mol. Genet. 5, 1649–1655. The 3' ends of ABCC1 and ABCC6 are only about 9 kb apart from each other so the genes face opposite directions (Cai et al., *J Mol Med*, 2000, 78, 36–46).

The locus for paroxysmal kinesigenic choreoathetosis (PKC) has been assigned to 16p11.2-q12.1, between markers D16S3093 and D16S416 (Tomita et al., *Am J Hum Genet*, 1999, 65, 1688–97; Bennett et al., *Neurology*, 2000, 54, 125–30; FIG. 2). An overlapping locus has been predicted to contain the gene for infantile convulsions with paroxysmal choreoathetosis (ICCA; Lee et al., *Hum Genet*, 1998, 103, 608–12). It was suggested that mutations in a novel ion-channel gene on chromosome 16 might be responsible for PKC and/or ICCA (Bennett et al., *Neurology*, 2000, 54, 125–30). Since another member of the ABCC subfamily, cystic fibrosis transmembrane conductance regulator (CFTR), functions as a cyclic AMP-regulated channel, and also as a regulator of other ion channels and transporters (Kleizen et al., *J Cell Biol*, 2000, 79, 544–56), it is feasible that this gene may function as ion channels (or regulators) and that mutations in these could result in a disease phenotype. Expression analysis of ABCC11 reveals that this gene is expressed in muscle and brain tissues, supporting the working hypothesis of the skeletal muscle or brain-related etiology of PKC. In summary, chromosomal localization, potential function, and expression profile make this gene a promising candidate for PKC/ICCA.

Example 3

Phylogenetic Analysis

Figure 5:
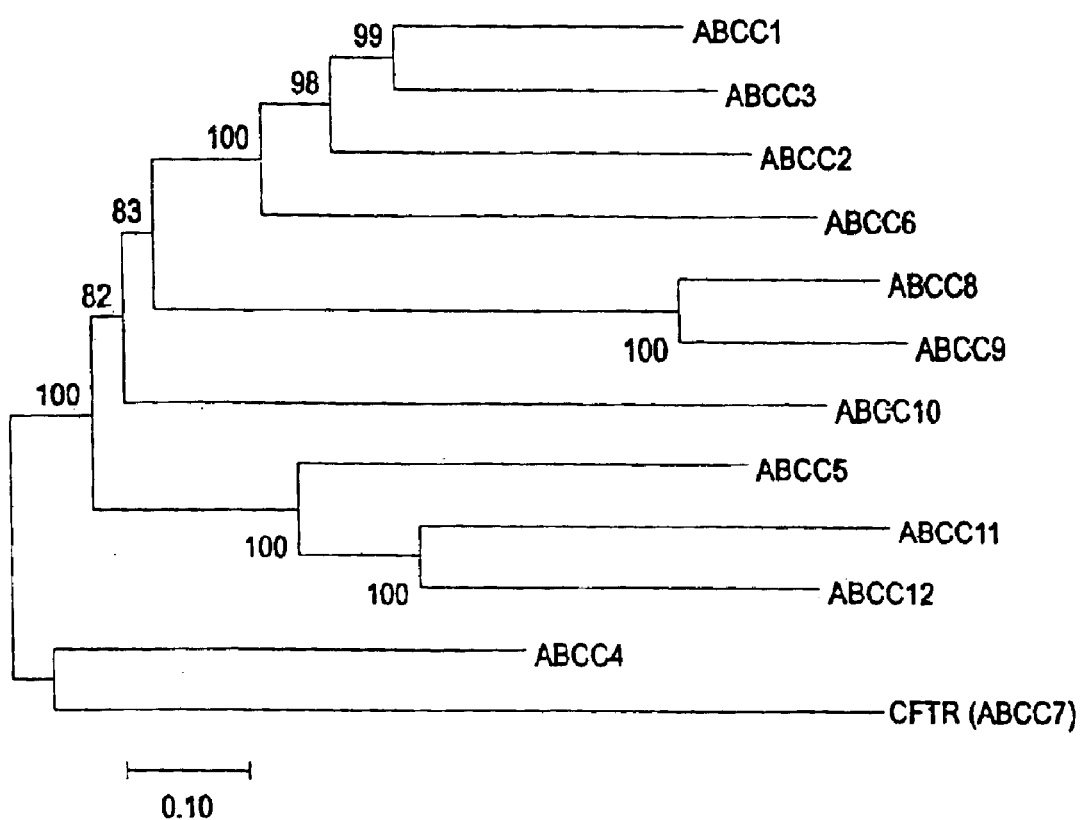
FIG. 5 displays a phylogenetic relationship of genes in the ABCC subfamily. Complete protein sequences of all members of the ABCC subfamily were aligned with the CLUSTALW program. The distance measure is given in substitutions per amino acid.

Phylogenetic analyses of the ABCC subfamily proteins clearly demonstrate a relatively recent duplication of the ABCC11 and ABCC12 genes (FIG. 5). The resulting neighbor-joining tree shows with maximum confidence (100-level of bootstrap support) a close evolutionary relationship of the ABCC11/ABCC12 cluster with the ABCC5 gene (FIG. 5). In addition, the analysis of the tree suggests a recent duplication of the ABCC8 and ABCC9 genes, while ABCC10 seems to be one of the first genes to separate from the common ancestor. ABCC1, ABCC2, ABCC3, and ABCC6 genes constitute a well-defined sub-cluster, while the ABCC4 and CFTR (ABCC7) genes form another reliable subset despite aapparent early divergence.

Example 4

Cell Lines

The human erythroleukemia K562 cells were obtained form the American Tissue Culture Collection (Rockville Md.) and were cultured in RPMI-1640 medium supplemented with 10% fetal calf serum, 2 mM 2-glutamine. The 9-(2-phosphonylmethoxyethyl)adenine (PMEA) resistant cells, K562/PMEA, were derived as described by Hatse et al. (*Mol Pharmacol*, 1996, 50, 1231–42). T-lymphoblast cell lines CEM and (−)2′,3′-dideoxy-3′-thiacytidine (3TC)-resistant CEM-3TC cells were selected. Cell lines, CEMss and CEM-r1, were described by Robbins et al. (*Mol Pharmacol,* 1995, 47, 391–7). CEM-r1 is highly resistant to PMEA due to an overexpression of ABCC4 (Schuetz et al., *Nat Med,* 1999, 5, 1048–51). Total RNA from these six cell lines (three pairs of wild type and resistant cell lines) was isolated with TRIZOL (GIBCO BRL), and RT-PCR performed at varying cycle numbers oligonucleotide primers as mentioned in FIG. 3. The PCR products were subcloned and verified by direct sequencing.

Reverse Transcription

In a total volume of 11.5 µl, 500 ng of mRNA poly(A)+ (Clontech) mixed with 500 ng of oligodT are denatured at 70° C. for 10 min and then chilled on ice. After addition of 10 units of RNAsin, 10 mM DTT, 0.5 mM dNTP, Superscript first strand buffer and 200 units of Superscript II (Life Technologies), the reaction is incubated for 45 min at 42° C.

PCR

Each polymerase chain reaction contained 400 µM each dNTP, 2 units of *Thermus aquaticus* (Taq) DNA polymerase (Ampli Taq Gold; Perkin Elmer), 0.5 µM each primer, 2.5 mM $MgCl_2$, PCR buffer and 50 ng of DNA, or about 25 ng of cDNA, or ⅕oè of primary PCR mixture. Reactions were carried out for 30 cycles in a Perkin Elmer 9700 thermal cycler in 96-well microtiter plates. After an initial denaturation at 94° C. for 10 min, each cycle consisted of: a denaturation step of 30 s (94° C.), a hybridization step of 30 s (64° C. for 2 cycles, 61° C. for 2 cycles, 58° C. for 2 cycles and 55° C. for 28 cycles), and an elongation step of 1 min/kb (72° C.). PCR ended with a final 72° C. extension of 7 min. In case of RT-PCR, control reactions without reverse transcriptase and reactions containing water instead of cDNA were performed for every sample.

DNA Sequencing

PCR products are analyzed and quantified by agarose gel electrophoresis, purified with a P100 column. Purified PCR products were sequenced using ABI Prism BigDye terminator cycle sequencing kit (Perkin Elmer Applied Biosystems). The sequence reaction mixture was purified using Microcon-100 microconcentrators (Amicon, Inc., Beverly). Sequencing reactions were resolved on an ABI 377 DNA sequencer (Perkin Elmer Applied Biosystems) according to manufacturer's protocol (Applied Biosystems, Perkin Elmer).

Primers

Oligonucleotides were selected using Prime from GCG package or Oligo 4 (National Biosciences, Inc.) softwares. Primers were ordered from Life Technologies, Ltd and used without further purification.

Example 5

Expression of ABCC11 in Human Tissues and Nucleotide-Resistant Cell Lines

Figure 3:
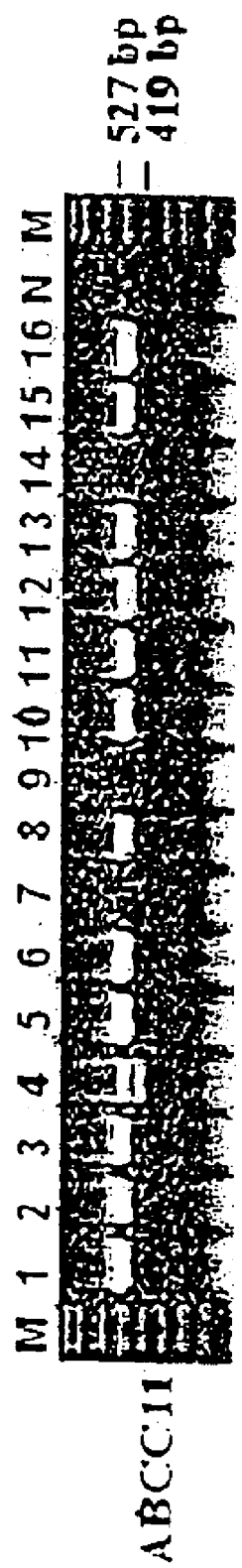
FIG. 3 represents the expression profiling of the human ABCC11 genes by PCR on human Multiple Tissue cDNA (MTC®, Clontech). Each lane contains normalized, first-strand cDNA from 16 human tissues/cells. Lanes 1–16 thus represent cDNA from heart, brain, placenta, lung, liver, muscle, kidney, pancreas, spleen, thymus, testes, ovary, intestine, colon, leukocyte, and prostate, respectively. N represents the negative control; M represents the marker lane (1 kb Plus DNA Ladder). The following primer pairs amplified specific gene products: ABCC11: forward 5'-AGA ATG GCT GTG AAG GCT CAG CAT C-3', reverse 5'-GTT CCT CTC CAG CTC CAG TGC-3'.

The expression pattern for the ABCC11 gene was examined by PCR on multiple tissue expression arrays (Clontech) with gene-specific primers resulting in about 500 bp PCR fragments (FIG. 3). Approximately 5000 bp mRNA species was observed by Northern blot. The primers used in expression studies amplified the ABCC11 cDNA from exon 7 to exon 10, resulting in a 527 pb PCR fragment (FIG. 3). In case of lung, a smaller (419 pb) fragment was detected also (FIG. 3). Direct sequencing of the PCR product determined that the shorter PCR product lacked exon 9 of the ABCC11 gene. Since these results were confirmed in repeated experiments, frequent skipping of ABCC11 exon 9 may occur in vivo. Exon skipping and alternative splicing events have been described for several ABC genes by Rickers et al. (Human Genet. (1994) 94, 311–313) and Bellincampi et al. (Biochem. Biophys. Res. Commun. (2001) 283, 590–597).

Systematic analysis of the tissue source of the ABCC11 ESTs from the public dbEST and the proprietary Incyte LifeSeq Gold databases resulted in 29 ESTs, with the majority being derived from breast tumor tissue (17). The others were from prostate (5 clones), testis (3), CNS (2), and colon (2). No EST had been derived from muscle libraries.

Since this new gene shows extensive structural similarity to ABCC5 (and to a certain extent, ABCC4), expression in three pairs of cell lines, K562 and K562-PMEA, CEMss and CEM-r1, CEM and CEM-3TC was also assessed. The K562-PMEA and CEM-r1 lines have been selected for resistance to PMEA, the CEM-3TC for resistance to the cytidine nucleoside analog, 3TC. No difference was observed in expression levels of ABCC11 between the parental and PMEA-resistant cell lines. In contrast, the CEM-3TC cell line revealed a reproducible 2–3 fold increase in the expression of ABCC11, when compared to the parental line CEM. This is a potentially interesting finding when one considers the close evolutionary relationship of ABCC11 and ABCC5 (FIGS. 1 and 5), in further view of recent studies demonstrating selective nucleotide analog transport by ABCC5 (Wijnholds et al., *Proc Natl Acad Sci,* 2000, 97, 7476–81). In addition, since the efflux-resistant phenotype of CEM-3TC can be explained only in part by ABCC4 overexpression, the higher expression of ABCC11 in these cells warrants further investigation.

Example 6

Construction of the Expression Vector Containing the Complete cDNA of ABCC11 in Mammalian Cells The ABCC11 gene may be expressed in mammalian cells. A typical eukaryotic expression vector contains a promoter which allows the initiation of the transcription of the mRNA, a sequence encoding the protein, and the signals required for the termination of the transcription and for the polyadenylation of the transcript. It also contains additional signals such as enhancers, the Kozak sequence and sequences necessary for the splicing of the mRNA. An effective transcription is obtained with the early and late elements of the SV40 virus promoters, the retroviral LTRs or the CMV virus early promoter. However, cellular elements such as the actin promoter may also be used. Many expression vectors may be used to carry out the present invention, an example of such a vector is pcDNA3 (Invitrogen).

Example 7

Production of Normal and Mutated ABCC11 Polypeptide

The normal ABCC11 polypeptide encoded by complete corresponding cDNAs whose isolation is described in Example 2, or the mutated ABCC11 polypeptide whose complete cDNA may also be obtained according to the techniques described in Example 2, may be easily produced in a bacterial or insect cell expression system using the baculovirus vectors or in mammalian cells with or without the vaccinia virus vectors. All the methods are now widely described and are known to persons skilled in the art. A detailed description thereof will be found for example in F. Ausubel et al. (1989, Current Protocols in Molecular

Example 8

Production of an Antibody Directed Against a Mutated ABCC11 Polypeptide

The antibodies in the present invention may be prepared by various methods (Current Protocols In Molecular Biology Volume I edited by Frederick M. Ausubel, Roger Brent, Robert E. Kingston, David D. Moore, J. G. Seidman, John A. Smith, Kevin Struhl—Massachusetts General Hospital Harvard Medical School, chapter 11, 1989). For example, the cells expressing a polypeptide of the present invention are injected into an animal in order to induce the production of serum containing the antibodies. In one of the methods described, the proteins are prepared and purified so as to avoid contaminations. Such a preparation is then introduced into the animal with the aim of producing polyclonal antisera having a higher activity.

In an example method, the antibodies of the present invention are monoclonal antibodies. Such monoclonal antibodies may be prepared using the hybridoma technique (Köhler et al, 1975, *Nature*, 256:495; Köhler et al, 1976, *Eur. J Immunol.* 6:292; Köhler et al, 1976, *Eur. J. Immunol.*, 6:511; Hammeling et al., 1981, *Monoclonal Antibodies and T-Cell Hybridomas*, Elsevier, N.Y., pp. 563–681). In general, such methods involve immunizing the animal (such as a mouse) with a polypeptide or better still with a cell expressing the polypeptide. These cells may be cultured in a suitable tissue culture medium. Eagle medium (modified Earle) supplemented with 10% fetal bovine serum (inactivated at 56° C.) and supplemented with about 10 g/l of nonessential amino acids, 1000 U/ml of penicillin and about 100 µg/ml of streptomycin may generally be used.

The splenocytes of these mice are extracted and fused with a suitable myeloma cell line, for example, the parental myeloma cell line (SP2O) available from the ATCC. After fusion, the resulting hybridoma cells are selectively maintained in HAT medium and then cloned by limiting dilution as described by Wands et al. (1981, *Gastroenterology*, 80:225–232). The hybridoma cells obtained after such a selection are tested in order to identify the clones secreting antibodies capable of binding to the polypeptide.

Moreover, other antibodies capable of binding to the polypeptide may be produced according to a 2-stage procedure using anti-idiotype antibodies such a method is based on the fact that the antibodies are themselves antigens and consequently it is possible to obtain an antibody recognizing another antibody. According to this method, the antibodies specific for the protein are used to immunize an animal, such as a mouse. The splenocytes of this animal are then used to produce hybridoma cells, and the latter are screened in order to identify the clones which produce an antibody whose capacity to bind to the specific antibody-protein complex may be blocked by the polypeptide. These antibodies may be used to immunize an animal in order to induce the formation of antibodies specific for the protein in a large quantity.

The Fab and F(ab')2 and the other fragments of the antibodies of the present invention may be used according to the methods described here. Such fragments are typically produced by proteolytic cleavage with the aid of enzymes such as Papain (in order to produce the Fab fragments) or Pepsin (in order to produce the F(ab')2 fragments). Otherwise, the secreted fragments recognizing the protein may be produced by applying the recombinant DNA or synthetic chemistry technology.

For the in vivo use of antibodies in humans, it may be preferable to use "humanized" chimeric monoclonal antibodies. Such antibodies may be produced using genetic constructs derived from hybridoma cells producing the monoclonal antibodies described above. The methods for producing the chimeric antibodies are known to persons skilled in the art (for are view, see: Morrison (1985. *Science* 229:1202); Oi et al., (1986, *Biotechnique*, 4:214); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al; (1984, *Nature*, 312:643); and Neuberger et al., (1985, *Nature*, 314:268).

Example 9

Determination of Polymorphisms/mutations in the ABCC11 Gene

The detection of polymorphisms or of mutations in the sequences of the transcripts or in the genomic sequence of the ABCC11 gene may be carried out according to various protocols. An example method is direct sequencing.

For patients from whom it is possible to obtain an mRNA preparation, an example method consists in preparing the cDNAs and sequencing them directly. For patients for whom only DNA is available, and in the case of a transcript where the structure of the corresponding gene is unknown or partially known, it is necessary to precisely determine its intron-exon structure as well as the genomic sequence of the corresponding gene. This therefore involves, in a first instance, isolating the genomic DNA BAC or cosmid clone (s) corresponding to the transcript studied, sequencing the insert of the corresponding clone(s) and determining the intron-exon structure by comparing the cDNA sequence to that of the genomic DNA obtained.

The technique of detection of mutations by direct sequencing consists in comparing the genomic sequence of the ABCC11 gene obtained from homozygotes for the disease or from at least 8 individuals (4 individuals affected by the pathology studied and 4 individuals not affected) or from at least 32 unrelated individuals from the studied population. The sequence divergences constitute polymorphisms. All those modifying the amino acid sequence of the wild-type protein may be mutations capable of affecting the function of said protein which it is preferred to consider more particularly for the study of cosegregation of the mutation and of the disease (denoted genotype-phenotype correlation) in the pedigree, or of a pharmacological response to a therapeutic molecule in the pharmacogenomic studies, or in the studies of case/control association for the analysis of the sporadic cases.

Example 10

Identification of a Causal Gene for a Disease Linked to the Chromosome Locus, such as Paroxysmal Kinesigenic Choreoathetosis by Causal Mutation or a Transcriptional Difference Among the mutations identified according to the method described in Example 9, all those associated with the disease phenotype are capable of being causal. Validation of these results is made by sequencing the gene in all the affected individuals and their relations.

Moreover, Northern blot or RT-PCR analysis, according to the methods described in Example 4, using RNA specific to affected or nonaffected individuals makes it possible to detect notable variations in the level of expression of the gene studied, in particular in the absence of transcription of the gene.

Example 11

Construction of Recombinant Vectors Comprising a Nucleic Acid Encoding the ABCC11 Protein Synthesis of a Nucleic Acid Encoding the Human ABCC11 Protein:

Total RNA (500 ng) isolated from a human cell (for example, placental tissue, Clontech, Palo Alto, Calif., USA, or THP1 cells) may be used as source for the synthesis of the cDNA of the human ABCC11 gene. Methods to reverse transcribe mRNA to cDNA are well known in the art. For example, one may use the system "Superscript one step RT-PCR (Life Technologies, Gaithersburg, Md., USA).

Oligonucleotide primers specific for ABCC11 cDNA may be used for this purpose. These oligonucleotide primers may be synthesized by the phosphoramidite method on a DNA synthesizer of the ABI 394 type (Applied Biosystems, Foster City, Cailf., USA).

Sites recognized by the restriction enzyme NotI may be incorporated into the amplified ABCC11 cDNA to flank the cDNA region desired for insertion into the recombinant vector by a second amplification step using 50 ng of human ABCC11 cDNA as template, and 0.25 µM of the ABCC11 specific oligonucleotide primers used above containing, at their 5' end, the site recognized by the restriction enzyme NotI (5'-GCGGCCGC-3'), in the presence of 200 µM of each of said dideoxynucleotides dATP, dCTP, dTTP and dGTP as well as the *Pyrococcus furiosus* DNA polymerase (Stratagene, Inc. La Jolla, Calif., USA).

The PCR reaction may be carried out over 30 cycles each comprising a step of denaturation at 95° C. for one minute, a step of renaturation at 50° C. for one minute and a step of extension at 72° C. for two minutes, in a thermocycler apparatus for PCR (Cetus Perkin Elmer Norwalk, Conn., USA).

Cloning of the cDNA of the Human ABCC11 Gene into an Expression Vector:

The human ABCC11 cDNA insert may then be cloned into the NotI restriction site of an expression vector, for example, the pCMV vector containing a cytomegalovirus (CMV) early promoter and an enhancer sequence as well as the SV40 polyadenylation signal (Beg et al., 1990, PNAS, 87:3473; Applebaum-Boden, 1996, JCI 97), in order to produce an expression vector designated pABCC11.

The sequence of the cloned cDNA can be confirmed by sequencing on the two strands using the reaction set "ABI Prism Big Dye Terminator Cycle Sequencing ready" (marketed by Applied Biosystems, Foster City, Calif., USA) in a capillary sequencer of the ABI 310 type (Applied Biosystems, Foster City, Calif., USA).

Construction of a Recombinant Adenoviral Vector Containing the cDNA of the Human ABCC11 Gene—Modification of the Expression Vector pCMV-β:

The β-galactosidase cDNA of the expression vector pCMV-β (Clontech, Palo Alto, Calif., USA, Gene Bank Accession No. U02451) may be deleted by digestion with the restriction endonuclease NotI and replaced with a multiple cloning site containing, from the 5' end to the 3' end, the following sites: NotI, AscI, RsrII, AvrII, SwaI, and NotI, cloned at the region of the NotI restriction site. The sequence of this multiple cloning site is: 5'-CGGCCGCGGCGC-GCCCGGACCGCCTAGGATTTAAATCGCGGCCCGCG-3'.

The DNA fragment between the EcoRI and SanI sites of the modified expression vector pCMV may be isolated and cloned into the modified XbaI site of the shuttle vector pXCXII (McKinnon et al., 1982, *Gene*, 19:33; McGrory et al., 1988, *Virology*, 163:614).

Modification of the Shuttle Vector pXCXII:

A multiple cloning site comprising, from the 5' end to the 3 end the XbaI, EcoRI, SfiI, PmeI, NheI, SrfI, PacI, SalI and XbaI restriction sites having the sequence: 5 'CTCTAGAAT-TCGGCCTCCGTGGCCGTT-TAAACGCTAGCGCCCGGGCTTAATTA AGTCGACTCTAGAGC-3', may be inserted at the level of the XbaI site (nucleotide at position 3329) of the vector pXCXII (McKinnon et al., 1982, Gene 19:33; McGrory et al., 1988, *Virology*, 163:614).

The EcoRI-SalI DNA fragment isolated from the modified vector pCMV-β containing the CMV promoter/enhancer, the donor and acceptor splicing sites of FV40 and the polyadenylation signal of FV40 may then be cloned into the EcoRI-SalI site of the modified shuttle vector pXCX, designated pCMV-11.

Preparation of the Shuttle Vector pAD12-ABCA:

The human ABCC11 cDNA is obtained by an RT-PCR reaction, as described above, and cloned at the level of the NotI site into the vector pCMV-12, resulting in the obtaining of the vector pCMV-ABCC11.

Construction of the ABC1 Recombinant Adenovirus:

The recombinant adenovirus containing the human ABCC11 cDNA may be constructed according to the technique described by McGrory et al. (1988, *Virology*, 163:614).

Briefly, the vector pAD12-ABCA is cotransfected with the vector tGM17 according to the technique of Chen et al. (1987, *Mol Cell Biol.*, 7:2745–2752).

Likewise, the vector pAD12-Luciferase was constructed and cotransfected with the vector pJM17.

The recombinant adenoviruses are identified by PCR amplification and subjected to two purification cycles before a large-scale amplification in the human embryonic kidney cell line HEK 293 (American Type Culture Collection, Rockville, Md., USA).

The infected cells are collected 48 to 72 hours after their infection with the adenoviral vectors and subjected to five freeze-thaw lysing cycles.

The crude lysates are extracted with the aid of Freon (Halocarbone 113, Matheson Product, Scaucus, N.J. USA), sedimented twice in cesium chloride supplemented with 0.2% murine albumine (Sigma Chemical Co., St. Louis, Mo., USA) and dialysed extensively against buffer composed of 150 nM NaCl, 10 mM Hepes (pH 7,4), 5 mM KCl, 1 mM $MgCl_2$, and 1 mM $CaCl_2$.

The recombinant adenoviruses are stored at −70° C. and titrated before their administration to animals or their incubation with cells in culture.

The absence of wild-type contaminating adenovirus is confirmed by screening with the aid of PCR amplification using oligonucleotide primers located in the structural portion of the deleted region.

Validation of the Expression of the Human ABCC11 cDNA:

Polyclonal antibodies specific for a human ABCC11 polypeptide may be prepared as described above in rabbits and chicks by injecting a synthetic polypeptide fragment derived from an ABCC11 protein, comprising all or part of an amino acid sequence as described in SEQ ID NO:30. These polyclonal antibodies are used to detect and/or quantify the expression of the human ABCC11 gene in cells and animal models by immunoblotting and/or immunodetection.

Expression in vitro of the Human ABCC11 cDNA in Cells:

Cells of the HEK293 line and of the COS-7 line (American Tissue Culture Collection, Bethesda, Md., USA), as well as fibroblasts in primary culture derived from Tangier patients or from patients suffering from hypo-alphalipoproteinemia are transfected with the expression vector pCMV-ABCC11(5–25 μg) using Lipofectamine (BRL, Gaithersburg, Md., USA) or by coprecipitation with the aid of calcium chloride (Chen et al., 1987, Mol Cell Biol., 7:2745–2752).

These cells may also be infected with the vector pABCC11-AdV (Index of infection, MOI=10).

The expression of human ABCC11 may be monitored by immunoblotting as well as by quantification of the efflux of cholesterol induced by apoA-1 using transfected and/or infected cells.

Expression in vivo of the ABCC11 Gene in Various Animal Models:

An appropriate volume (100 to 300 μl) of a medium containing the purified recombinant adenovirus (pABCA-AdV or pLucif-AdV) containing from $10^8$ to $10^9$ lysis plaque-forming units (pfu) are infused into the Saphenous vein of mice (C57BL/6, both control mice and models of transgenic or knock-out mice) on day 0 of the experiment.

The evaluation of the physiological role of the ABCC11 protein in the transport of cholesterol or inflammatory lipid substances is carried out by determining the total quantity of cholesterol or appropriate inflammatory lipid substances before (day zero) and after (days 2, 4, 7, 10, 14) the administration of the adenovirus.

Kinetic studies with the aid of radioactively labelled products are carried out on day 5 after the administration of the vectors rLucif-AdV and rABCA-AdV in order to evaluate the effect of the expression of the ABCC11 gene on the transport of cholesterol and inflammatory lipid substances.

Furthermore, transgenic mice and rabbits overexpressing the ABCC11 gene may be produced, in accordance with the teaching of Vaisman (1995) and Hoeg (1996) using constructs containing the human ABCC11 cDNA under the control of endogenous promoter such as ABCC11, or CMV or apoE.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

We claim:

1. An isolated nucleic acid comprising the nucleotide sequence set forth in SEQ ID NO:1, or a sequence complementary thereto.

2. A nucleotide probe or primer specific for an ATP-binding cassette (ABCC11) gene, wherein the nucleotide probe or primer comprises the nucleotide sequence of SEQ ID NO:1, or a nucleotide sequence complementary thereto.

3. A recombinant vector comprising the nucleic acid according to claim 1.

4. The vector according to claim 3, wherein the vector is an adenovirus.

5. A recombinant host cell comprising the recombinant vector according to claim 3.

6. A recombinant host cell comprising the nucleic acid according to claim 1.

7. An isolated nucleic acid encoding a polypeptide comprising an amino acid sequence of SEQ ID NO:31.

8. A recombinant vector comprising the nucleic acid according to claim 7.

9. A recombinant host cell comprising the nucleic acid according to claim 7.

10. A recombinant host cell comprising the recombinant vector according to claim 8.

* * * * *

SEQUENCE LISTING

<160> NUMBER OF SEQ ID NOS: 31

<210> SEQ ID NO 1
<211> LENGTH: 4862
<212> TYPE: DNA
<213> ORGANISM: Homo sapiens

<400> SEQUENCE: 1

```
actgggataa agcaagaaga ctgattttat gagcaggggt ttgatacatc aaaggagatt      60
gcccaggatc aagggtgcgg tgttgggggt gggttgggga gggtggttag agaaggtttc     120
actaagtgat ttgggcctga ggcctgagaa gatgtttaaa aagagggatc aagcacaggc     180
taaggagagg aaagagcagg cacccaaacc tctgcatggc cccaatatgc tccctgcagg     240
gtagtgcccc ctcttctggc tgctcaaggc gagatctaag cttcttctaa ctcctgctgt     300
cttttcatat tctctgattc tgggaaacga agaattggca ggaactgaaa atgactagga     360
agaggacata ctgggtgccc aactcttctg gtggcctcgt gaatcgtggc atcgacatag     420
gcgatgacat ggtttcagga cttatttata aaacctatac tctccaagat ggcccctgga     480
gtcagcaaga gagaaatcct gaggctccag ggagggcagc tgtcccaccg tgggggaagt     540
atgatgctgc cttgagaacc atgattccct tccgtcccaa gccgaggttt cctgccccc      600 agccctgga caatgctggc ctgttctcct acctcaccgt gtcatggctc accccgctca     660
tgatccaaag cttacggagt cgcttagatg agaacaccat ccctccactg tcagtccatg     720
atgcctcaga caaaaatgtc caaaggcttc accgcctttg ggaagaagaa gtctcaaggc     780
gagggattga aaaagcttca gtgcttctgg tgatgctgag gttccagaga acaaggttga     840
ttttcgatgc acttctgggc atctgcttct gcattgccaa tgtactcggg ccaatattga     900
ttataccaaa gatcctggaa tattcagaag agcagttggg gaatgttgtc catggagtgg     960
gactctgctt tgcccttttt ctctccgaat gtgtgaagtc tctgagtttc tcctccagtt    1020
ggatcatcaa ccaacgcaca gccatcaggt tccgagcagc tgtttcctcc tttgcctttg    1080
agaagctcat ccaatttaag tctgtaatac acatcacctc aggagaggcc atcagcttct    1140
```

```
tcaccggtga tgtaaactac ctgtttgaag gggtgtgcta tggacccta gtactgatca    1200
cctgcgcatc gctggtcatc tgcagcattt cttcctactt cattattgga tacactgcat    1260
ttattgccat cttatgctat ctcctggttt tcccactggc ggtattcatg acaagaatgg    1320
ctgtgaaggc tcagcatcac acatctgagg tcagcgacca gcgcatccgt gtgaccagtg    1380
aagttctcac ttgcattaag ctgattaaaa tgtacacatg ggagaaacca tttgcaaaaa    1440
tcattgaaga cctaagaagg aaggaaagga actattgga gaagtgcggg cttgtccaga    1500
gcctgacaag tataaccttg ttcatcatcc ccacagtggc cacagcggtc tgggttctca    1560
tccacacatc cttaaagctg aaactcacag cgtcaatggc cttcagcatg ctggcctcct    1620
tgaatctcct tcggctgtca gtgttctttg tgcctattgc agtcaaaggt ctcacgaatt    1680
ccaagtctgc agtgatgagg ttcaagaagt ttttcctcca ggagagccct gttttctatg    1740
tccagacatt acaagacccc agcaaagctc tggtctttga ggaggccacc ttgtcatggc    1800
aacagacctg tcccgggatc gtcaatgggg cactggagct ggagaggaac gggcatgctt    1860
ctgaggggat gaccaggcct agagatgccc tcgggccaga ggaagaaggg aacagcctgg    1920
gcccagagtt gcacaagatc aacctggtgg tgtccaaggg gatgatgtta ggggtctgcg    1980
gcaacacggg gagtggtaag agcagcctgt tgtcagccat cctggaggag atgcacttgc    2040
tcgagggctc ggtggggtg cagggaagcc tggcctatgt cccccagcag gcctggatcg    2100
tcagcgggaa catcagggag aacatcctca tgggaggcgc atatgacaag gccccgatacc    2160
tccaggtgct ccactgctgc tccctgaatc gggacctgga acttctgccc tttggagaca    2220
tgacagagat tggagagcgg ggcctcaacc tctctggggg gcagaaacag aggatcagcc    2280
tggcccgcgc cgtctattcc gaccgtcaga tctacctgct ggacgacccc ctgtctgctg    2340
tggacgccca cgtggggaag cacattttg aggagtgcat taagaagaca ctcaggggga    2400
agacggtcgt cctggtgacc caccagctgc agtacttaga attttgtggc cagatcattt    2460
tgttggaaaa tgggaaaatc tgtgaaaatg gaactcacag tgagttaatg cagaaaaagg    2520
ggaaatatgc ccaacttatc cagaagatgc acaaggaagc cacttcggac atgttgcagg    2580
acacagcaaa gatagcagag aagccaaagg tagaaagtca ggctctggcc acctccctgg    2640
aagagtctct caacgaaaat gctgtgccgg agcatcagct cacacaggag gaggagatgg    2700
aagaaggctc cttgagttgg agggtctacc accactacat ccaggcagct ggaggttaca    2760
tggtctcttg cataattttc ttcttcgtgg tgctgatcgt cttcttaacg atcttcagct    2820
tctggtggct gagctactgg ttggagcagg gctcgggac caatagcagc cgagagagca    2880
atggaaccat ggcagacctg gcaacattg cagacaatcc tcaactgtcc ttctaccagc    2940
tggtgtacgg gctcaacgcc ctgctcctca tctgtgtggg ggtctgctcc tcagggattt    3000
tcaccaaagt cacgaggaag gcatccacgg ccctgcacaa caagctcttc aacaaggttt    3060
tccgctgccc catgagtttc tttgacacca tcccaatagg ccggcttttg aactgcttcg    3120
cagggacttt ggaacagctg gaccagctct tgcccatctt ttcagagcag ttcctggtcc    3180
tgtccttaat ggtgatcgcc gtcctgttga ttgtcagtgt gctgtctcca tatatcctgt    3240
taatgggagc cataatcatg gttatttgct tcatttatta tatgatgttc aagaaggcca    3300
tcggtgtgtt caagagactg gagaactata gccggtctcc tttattctcc cacatcctca    3360
attctctgca aggcctgagc tccatccatg tctatggaaa aactgaagac ttcatcagcc    3420
agtttaagag gctgactgat gcgcagaata actacctgct gttgtttcta tcttccacac    3480
```

-continued

```
gatggatggc attgaggctg gagatcatga ccaaccttgt gaccttggct gttgccctgt      3540
tcgtggcttt tggcatttcc tccaccccct actcctttaa agtcatggct gtcaacatcg      3600
tgctgcagct ggcgtccagc ttccaggcca ctgcccggat tggcttggag acagaggcac      3660
agttcacggc tgtagagagg atactgcagt acatgaagat gtgtgtctcg gaagctcctt      3720
tacacatgga aggcacaagt tgtccccagg ggtggccaca gcatgggaa atcatatttc       3780 aggattatca catgaaatac agagacaaca cacccaccgt gcttcacggc atcaacctga      3840
ccatccgcgg ccacgaagtg gtgggcatcg tgggaaggac gggctctggg aagtcctcct      3900
tgggcatggc tctcttccgc ctggtggagc ccatggcagg ccggattctc attgacggcg      3960
tggacatttg cagcatcggc ctggaggact gcggtccaa gctctcagtg atccctcaag       4020
atccagtgct gctctcagga accatcagat tcaacctaga tccctttgac cgtcacactg      4080
accagcagat ctgggatgcc ttggagagga cattcctgac caaggccatc tcaaagttcc      4140
ccaaaaagct gcatacagat gtggtggaaa acggtgaaa cttctctgtg ggggagaggc       4200
agctgctctg cattgccagg gctgtgcttc gcaactccaa gatcatcctt atcgatgaag      4260
ccacagcctc cattgacatg gagacagaca ccctgatcca gcgcacaatc cgtgaagcct      4320
tccagggctg caccgtgctc gtcattgccc accgtgtcac cactgtgctg aactgtgacc      4380
acatcctggt tatgggcaat gggaaggtgg tagaatttga tcggccggag gtactgcgga      4440
agaagcctgg gtcattgttc gcagccctca tggccacagc cacttcttca ctgagataag      4500
gagatgtgga gacttcatgg aggctggcag ctgagctcag aggttcacac aggtgcagct      4560
tcgaggccca cagtctgcga ccttcttgtt tggagatgag aacttctcct ggaagcaggg      4620
gtaaatgtag gggggtggg gattgctgga tggaaaccct ggaataggct acttgatggc       4680
tctcaagacc ttagaacccc agaaccatct aagacatggg attcagtgat catgtggttc      4740
tccttttaac ttcatgctg aataatttta taataaggta aaagcttata gttttctgat       4800
ctgtgttaga agtgttgcaa atgctgtact gactttgtaa aatataaaac taaggaaaac      4860
tc                                                                    4862
```

<210> SEQ ID NO 2
<211> LENGTH: 449
<212> TYPE: DNA
<213> ORGANISM: Homo sapiens

<400> SEQUENCE: 2

```
actgggataa agcaagaaga ctgattttat gagcaggggt ttgatacatc aaaggagatt       60
gcccaggatc aagggtgcgg tgttgggggt gggttgggga gggtggttag agaaggtttc      120
actaagtgat ttgggcctga ggcctgagaa gatgtttaaa agagggatc aagcacaggc       180 taaggagagg aaagagcagg cacccaaacc tctgcatggc cccaatatgc tccctgcagg      240
gtagtgcccc ctcttctggc tgctcaaggc gagatctaag cttcttctaa ctcctgctgt      300
cttttcatat tctctgattc tgggaaacga agaattggca ggaactgaaa atgactagga      360
agaggacata ctgggtgccc aactcttctg gtgccctcgt gaatcgtggc atcgacatag      420
gcgatgacat ggtttcagga cttatttat                                        449
```

<210> SEQ ID NO 3
<211> LENGTH: 137
<212> TYPE: DNA
<213> ORGANISM: Homo sapiens

<400> SEQUENCE: 3

-continued

```
aaaacctata ctctccaaga tggcccctgg agtcagcaag agagaaatcc tgaggctcca      60
gggagggcag ctgtcccacc gtggggaag tatgatgctg ccttgagaac catgattccc      120
ttccgtccca agccgag                                                     137

<210> SEQ ID NO 4
<211> LENGTH: 159
<212> TYPE: DNA
<213> ORGANISM: Homo sapiens

<400> SEQUENCE: 4
gtttcctgcc ccccagcccc tggacaatgc tggcctgttc tcctacctca ccgtgtcatg      60
gctcaccccg ctcatgatcc aaagcttacg gagtcgctta gatgagaaca ccatccctcc     120
actgtcagtc catgatgcct cagacaaaaa tgtccaaag                            159

<210> SEQ ID NO 5
<211> LENGTH: 148
<212> TYPE: DNA
<213> ORGANISM: Homo sapiens

<400> SEQUENCE: 5
gcttcaccgc ctttgggaag aagaagtctc aaggcgaggg attgaaaaag cttcagtgct      60
tctggtgatg ctgaggttcc agagaacaag gttgattttc gatgcacttc tgggcatctg     120
cttctgcatt gccagtgtac tcgggcca                                        148

<210> SEQ ID NO 6
<211> LENGTH: 234
<212> TYPE: DNA
<213> ORGANISM: Homo sapiens

<400> SEQUENCE: 6
atattgatta taccaaagat cctggaatat tcagaagagc agttgggaa tgttgtccat       60 ggagtgggac tctgctttgc ccttttctc tccgaatgtg tgaagtctct gagtttctcc     120
tccagttgga tcatcaacca acgcacagcc atcaggttcc gagcagctgt ttcctccttt    180
gcctttgaga agctcatcca atttaagtct gtaatacaca tcacctcagg agag           234

<210> SEQ ID NO 7
<211> LENGTH: 174
<212> TYPE: DNA
<213> ORGANISM: Homo sapiens

<400> SEQUENCE: 7
gccatcagct tcttcaccgg tgatgtaaac tacctgtttg aagggtgtg ctatggaccc       60 ctagtactga tcacctgcgc atcgctggtc atctgcagca tttcttccta cttcattatt    120
ggatacactg catttattgc catcttatgc tatctcctgg ttttcccact ggcg           174

<210> SEQ ID NO 8
<211> LENGTH: 148
<212> TYPE: DNA
<213> ORGANISM: Homo sapiens

<400> SEQUENCE: 8
gtattcatga caagaatggc tgtgaaggct cagcatcaca catctgaggt cagcgaccag      60
cgcatccgtg tgaccagtga agttctcact tgcattaagc tgattaaaat gtacacatgg    120
gagaaaccat ttgcaaaaat cattgaag                                       148
```

<210> SEQ ID NO 9
<211> LENGTH: 149
<212> TYPE: DNA
<213> ORGANISM: Homo sapiens

<400> SEQUENCE: 9
acctaagaag gaaggaaagg aaactattgg agaagtgcgg gcttgtccag agcctgacaa     60
gtataacctt gttcatcatc cccacagtgg ccacagcggt ctgggttctc atcccacat    120 ccttaaagct gaaactcaca gcgtcaatg                                     149

<210> SEQ ID NO 10
<211> LENGTH: 108
<212> TYPE: DNA
<213> ORGANISM: Homo sapiens

<400> SEQUENCE: 10
gccttcagca tgctggcctc cttgaatctc cttcggctgt cagtgttctt tgtgcctatt     60
gcagtcaaag gtctcacgaa ttccaagtct gcagtgatga ggttcaag                108

<210> SEQ ID NO 11
<211> LENGTH: 252
<212> TYPE: DNA
<213> ORGANISM: Homo sapiens

<400> SEQUENCE: 11
aagtttttcc tccaggagag ccctgttttc tatgtccaga cattacaaga ccccagcaaa     60
gctctggtct ttgaggaggc caccttgtca tggcaacaga cctgtcccgg gatcgtcaat    120
ggggcactgg agctggagag gaacgggcat gcttctgagg ggatgaccag gcctagagat    180
gccctcgggc cagaggaaga agggaacagc ctgggcccag agttgcacaa gatcaacctg    240
gtggtgtcca ag                                                        252

<210> SEQ ID NO 12
<211> LENGTH: 72
<212> TYPE: DNA
<213> ORGANISM: Homo sapiens

<400> SEQUENCE: 12
gggatgatgt tagggtctg cggcaacacg gggagtggta agagcagcct gttgtcagcc      60
atcctggagg ag                                                         72

<210> SEQ ID NO 13
<211> LENGTH: 125
<212> TYPE: DNA
<213> ORGANISM: Homo sapiens

<400> SEQUENCE: 13
atgcacttgc tcgagggctc ggtgggggtg caggaagcc tggcctatgt cccccagcag      60
gcctggatcg tcagcgggaa catcagggag aacatcctca tgggaggcgc atatgacaag    120
gcccg                                                                125

<210> SEQ ID NO 14
<211> LENGTH: 73
<212> TYPE: DNA
<213> ORGANISM: Homo sapiens

<400> SEQUENCE: 14
atacctccag gtgctccact gctgctccct gaatcgggac ctggaacttc tgcccttgg      60 agacatgaca gag                                                73

<210> SEQ ID NO 15
<211> LENGTH: 204
<212> TYPE: DNA
<213> ORGANISM: Homo sapiens

<400> SEQUENCE: 15
attggagagc ggggcctcaa cctctctggg gggcagaaac agaggatcag cctggcccgc    60
gccgtctatt ccgaccgtca gatctacctg ctggacgacc cctgtctgc tgtggacgcc   120 cacgtgggga agcacatttt tgaggagtgc attaagaaga cactcagggg gaagacggtc   180
gtcctggtga cccaccagct gcag                                         204

<210> SEQ ID NO 16
<211> LENGTH: 135
<212> TYPE: DNA
<213> ORGANISM: Homo sapiens

<400> SEQUENCE: 16
tacttagaat tttgtggcca gatcattttg ttggaaaatg ggaaaatctg tgaaaatgga    60
actcacagtg agttaatgca gaaaaagggg aaatatgccc aacttatcca gaagatgcac   120
aaggaagcca cttcg                                                   135

<210> SEQ ID NO 17
<211> LENGTH: 97
<212> TYPE: DNA
<213> ORGANISM: Homo sapiens

<400> SEQUENCE: 17
gacatgttgc aggacacagc aaagatagca gagaagccaa aggtagaaag tcaggctctg    60
gccacctccc tggaagagtc tctcaacgga aatgctg                            97

<210> SEQ ID NO 18
<211> LENGTH: 89
<212> TYPE: DNA
<213> ORGANISM: Homo sapiens

<400> SEQUENCE: 18
tgccggagca tcagctcaca caggaggagg agatggaaga aggctccttg agttggaggg    60
tctaccacca ctacatccag gcagctgga                                     89

<210> SEQ ID NO 19
<211> LENGTH: 104
<212> TYPE: DNA
<213> ORGANISM: Homo sapiens

<400> SEQUENCE: 19
gttacatggt ctcttgcata attttcttct tcgtggtgct gatcgtcttc ttaacgatct    60
tcagcttctg gtggctgagc tactggttgg agcagggctc gggg                   104

<210> SEQ ID NO 20
<211> LENGTH: 198
<212> TYPE: DNA
<213> ORGANISM: Homo sapiens

<400> SEQUENCE: 20
accaatagca gccgagagag caatggaacc atggcagacc tggcaacat tgcagacaat    60

```
cctcaactgt ccttctacca gctggtgtac gggctcaacg ccctgctcct catctgtgtg    120
ggggtctgct cctcagggat tttcaccaaa gtcacgagga aggcatccac ggccctgcac    180
aacaagctct tcaacaag                                                  198
```

<210> SEQ ID NO 21
<211> LENGTH: 227
<212> TYPE: DNA
<213> ORGANISM: Homo sapiens

<400> SEQUENCE: 21

```
gttttccgct gccccatgag tttctttgac accatcccaa taggccggct tttgaactgc     60
ttcgcagggg acttggaaca gctggaccag ctcttgccca tcttttcaga gcagttcctg    120
gtcctgtcct taatggtgat cgccgtcctg ttgattgtca gtgtgctgtc tccatatatc    180
ctgttaatgg gagccataat catggttatt tgcttcattt attatat                  227
```

<210> SEQ ID NO 22
<211> LENGTH: 138
<212> TYPE: DNA
<213> ORGANISM: Homo sapiens

<400> SEQUENCE: 22

```
gatgttcaag aaggccatcg gtgtgttcaa gagactggag aactatagcc ggtctccttt     60
attctcccac atcctcaatt ctctgcaagg cctgagctcc atccatgtct atggaaaaac    120
tgaagacttc atcagcca                                                  138
```

<210> SEQ ID NO 23
<211> LENGTH: 187
<212> TYPE: DNA
<213> ORGANISM: Homo sapiens

<400> SEQUENCE: 23

```
gtttaagagg ctgactgatg cgcagaataa ctacctgctg ttgtttctat cttccacacg     60
atggatggca ttgaggctgg agatcatgac caaccttgtg accttggctg ttgccctgtt    120
cgtggctttt ggcatttcct ccacccccta ctcctttaaa gtcatggctg tcaacatcgt    180
gctgcag                                                              187
```

<210> SEQ ID NO 24
<211> LENGTH: 90
<212> TYPE: DNA
<213> ORGANISM: Homo sapiens

<400> SEQUENCE: 24

```
ctggcgtcca gcttccaggc cactgcccgg attggcttgg agacagaggc acagttcacg     60
gctgtagaga ggatactgca gtacatgaag                                      90
```

<210> SEQ ID NO 25
<211> LENGTH: 190
<212> TYPE: DNA
<213> ORGANISM: Homo sapiens

<400> SEQUENCE: 25

```
atgtgtgtct cggaagctcc tttacacatg gaaggcacaa gttgtcccca ggggtggcca     60
cagcatgggg aaatcatatt tcaggattat cacatgaaat acagagacaa cacccccacc    120
gtgcttcacg gcatcaacct gaccatccgc ggccacgaag tggtgggcat cgtgggaagg    180
acgggctctg                                                           190
```

<210> SEQ ID NO 26
<211> LENGTH: 160
<212> TYPE: DNA
<213> ORGANISM: Homo sapiens

<400> SEQUENCE: 26

```
ggaagtcctc cttgggcatg gctctcttcc gcctggtgga gcccatggca ggccggattc      60
tcattgacgg cgtggacatt tgcagcatcg gcctggagga cttgcggtcc aagctctcag     120
tgatccctca agatccagtg ctgctctcag gaaccatcag                           160
```

<210> SEQ ID NO 27
<211> LENGTH: 79
<212> TYPE: DNA
<213> ORGANISM: Homo sapiens

<400> SEQUENCE: 27

```
attcaaccta gatccctttg accgtcacac tgaccagcag atctgggatg ccttggagag      60
gacattcctg accaaggcc                                                   79
```

<210> SEQ ID NO 28
<211> LENGTH: 114
<212> TYPE: DNA
<213> ORGANISM: Homo sapiens

<400> SEQUENCE: 28

```
atctcaaagt tccccaaaaa gctgcataca gatgtggtgg aaaacggtgg aaacttctct      60
gtgggggaga ggcagctgct ctgcattgcc agggctgtgc ttcgcaactc caag           114
```

<210> SEQ ID NO 29
<211> LENGTH: 165
<212> TYPE: DNA
<213> ORGANISM: Homo sapiens

<400> SEQUENCE: 29

```
atcatcctta tcgatgaagc cacagcctcc attgacatgg agacagacac cctgatccag      60
cgcacaatcc gtgaagcctt ccagggctgc accgtgctcg tcattgccca ccgtgtcacc     120
actgtgctga actgtgacca catcctggtt atgggcaatg ggaag                     165
```

<210> SEQ ID NO 30
<211> LENGTH: 456
<212> TYPE: DNA
<213> ORGANISM: Homo sapiens

<400> SEQUENCE: 30

```
gtggtagaat ttgatcggcc ggaggtactg cggaagaagc ctgggtcatt gttcgcagcc      60
ctcatggcca cagccacttc ttcactgaga taaggagatg tggagacttc atggaggctg     120
gcagctgagc tcagaggttc acacaggtgc agcttcgagg cccacagtct gcgaccttct     180
tgtttggaga tgagaacttc tcctggaagc agggtaaat gtaggggggg tgggattgc      240
tggatggaaa ccctggaata ggctacttga tggctctcaa gaccttagaa ccccagaacc     300
atctaagaca tgggattcag tgatcatgtg gttctccttt taacttacat gctgaataat     360
tttataataa ggtaaaagct tatagttttc tgatctgtgt tagaagtgtt gcaaatgctg     420
tactgacttt gtaaaatata aactaagga aaactc                                456
```

<210> SEQ ID NO 31

```
<211> LENGTH: 1382
<212> TYPE: PRT
<213> ORGANISM: Homo sapiens

<400> SEQUENCE: 31

Met Thr Arg Lys Arg Thr Tyr Trp Val Pro Asn Ser Ser Gly Gly Leu
  1               5                  10                  15

Val Asn Arg Gly Ile Asp Ile Gly Asp Asp Met Val Ser Gly Leu Ile
             20                  25                  30

Tyr Lys Thr Tyr Thr Leu Gln Asp Gly Pro Trp Ser Gln Gln Glu Arg
         35                  40                  45

Asn Pro Glu Ala Pro Gly Arg Ala Ala Val Pro Pro Trp Gly Lys Tyr
     50                  55                  60

Asp Ala Ala Leu Arg Thr Met Ile Pro Phe Arg Pro Lys Pro Arg Phe
 65                  70                  75                  80

Pro Ala Pro Gln Pro Leu Asp Asn Ala Gly Leu Phe Ser Tyr Leu Thr
                 85                  90                  95

Val Ser Trp Leu Thr Pro Leu Met Ile Gln Ser Leu Arg Ser Arg Leu
            100                 105                 110

Asp Glu Asn Thr Ile Pro Pro Leu Ser Val His Asp Ala Ser Asp Lys
        115                 120                 125

Asn Val Gln Arg Leu His Arg Leu Trp Glu Glu Val Ser Arg Arg
130                 135                 140

Gly Ile Glu Lys Ala Ser Val Leu Leu Val Met Leu Arg Phe Gln Arg
145                 150                 155                 160

Thr Arg Leu Ile Phe Asp Ala Leu Leu Gly Ile Cys Phe Cys Ile Ala
                165                 170                 175

Ser Val Leu Gly Pro Ile Leu Ile Ile Pro Lys Ile Leu Glu Tyr Ser
            180                 185                 190

Glu Glu Gln Leu Gly Asn Val Val His Gly Val Gly Leu Cys Phe Ala
        195                 200                 205

Leu Phe Leu Ser Glu Cys Val Lys Ser Leu Ser Phe Ser Ser Ser Trp
    210                 215                 220

Ile Ile Asn Gln Arg Thr Ala Ile Arg Phe Arg Ala Ala Val Ser Ser
225                 230                 235                 240

Phe Ala Phe Glu Lys Leu Ile Gln Phe Lys Ser Val Ile His Ile Thr
                245                 250                 255

Ser Gly Glu Ala Ile Ser Phe Phe Thr Gly Asp Val Asn Tyr Leu Phe
            260                 265                 270

Glu Gly Val Cys Tyr Gly Pro Leu Val Leu Ile Thr Cys Ala Ser Leu
        275                 280                 285

Val Ile Cys Ser Ile Ser Ser Tyr Phe Ile Ile Gly Tyr Thr Ala Phe
    290                 295                 300

Ile Ala Ile Leu Cys Tyr Leu Leu Val Phe Pro Leu Ala Val Phe Met
305                 310                 315                 320

Thr Arg Met Ala Val Lys Ala Gln His His Thr Ser Glu Val Ser Asp
                325                 330                 335

Gln Arg Ile Arg Val Thr Ser Glu Val Leu Thr Cys Ile Lys Leu Ile
            340                 345                 350

Lys Met Tyr Thr Trp Glu Lys Pro Phe Ala Lys Ile Ile Glu Asp Leu
        355                 360                 365

Arg Arg Lys Glu Arg Lys Leu Leu Glu Lys Cys Gly Leu Val Gln Ser
    370                 375                 380

Leu Thr Ser Ile Thr Leu Phe Ile Ile Pro Thr Val Ala Thr Ala Val
```

-continued

```
               385                 390                 395                 400
Trp Val Leu Ile His Thr Ser Leu Lys Leu Lys Leu Thr Ala Ser Met
                    405                 410                 415
Ala Phe Ser Met Leu Ala Ser Leu Asn Leu Leu Arg Leu Ser Val Phe
                420                 425                 430
Phe Val Pro Ile Ala Val Lys Gly Leu Thr Asn Ser Lys Ser Ala Val
                435                 440                 445
Met Arg Phe Lys Lys Phe Phe Leu Gln Glu Ser Pro Val Phe Tyr Val
        450                 455                 460
Gln Thr Leu Gln Asp Pro Ser Lys Ala Leu Val Phe Glu Glu Ala Thr
465                 470                 475                 480
Leu Ser Trp Gln Gln Thr Cys Pro Gly Ile Val Asn Gly Ala Leu Glu
                    485                 490                 495
Leu Glu Arg Asn Gly His Ala Ser Glu Gly Met Thr Arg Pro Arg Asp
                500                 505                 510
Ala Leu Gly Pro Glu Glu Gly Asn Ser Leu Gly Pro Glu Leu His
                515                 520                 525
Lys Ile Asn Leu Val Val Ser Lys Gly Met Met Leu Gly Val Cys Gly
                530                 535                 540
Asn Thr Gly Ser Gly Lys Ser Ser Leu Leu Ser Ala Ile Leu Glu Glu
545                 550                 555                 560
Met His Leu Leu Glu Gly Ser Val Gly Val Gln Gly Ser Leu Ala Tyr
                    565                 570                 575
Val Pro Gln Gln Ala Trp Ile Val Ser Gly Asn Ile Arg Glu Asn Ile
                580                 585                 590
Leu Met Gly Gly Ala Tyr Asp Lys Ala Arg Tyr Leu Gln Val Leu His
                595                 600                 605
Cys Cys Ser Leu Asn Arg Asp Leu Glu Leu Leu Pro Phe Gly Asp Met
            610                 615                 620
Thr Glu Ile Gly Glu Arg Gly Leu Asn Leu Ser Gly Gly Gln Lys Gln
625                 630                 635                 640
Arg Ile Ser Leu Ala Arg Ala Val Tyr Ser Asp Arg Gln Ile Tyr Leu
                    645                 650                 655
Leu Asp Asp Pro Leu Ser Ala Val Asp Ala His Val Gly Lys His Ile
                660                 665                 670
Phe Glu Glu Cys Ile Lys Lys Thr Leu Arg Gly Lys Thr Val Val Leu
            675                 680                 685
Val Thr His Gln Leu Gln Tyr Leu Glu Phe Cys Gly Gln Ile Ile Leu
        690                 695                 700
Leu Glu Asn Gly Lys Ile Cys Glu Asn Gly Thr His Ser Glu Leu Met
705                 710                 715                 720
Gln Lys Lys Gly Lys Tyr Ala Gln Leu Ile Gln Lys Met His Lys Glu
                    725                 730                 735
Ala Thr Ser Asp Met Leu Gln Asp Thr Ala Lys Ile Ala Glu Lys Pro
                740                 745                 750
Lys Val Glu Ser Gln Ala Leu Ala Thr Ser Leu Glu Glu Ser Leu Asn
            755                 760                 765
Gly Asn Ala Val Pro Glu His Gln Leu Thr Gln Glu Glu Met Glu
        770                 775                 780
Glu Gly Ser Leu Ser Trp Arg Val Tyr His His Tyr Ile Gln Ala Ala
785                 790                 795                 800
Gly Gly Tyr Met Val Ser Cys Ile Ile Phe Phe Val Val Leu Ile
                    805                 810                 815
```

-continued

```
Val Phe Leu Thr Ile Phe Ser Phe Trp Trp Leu Ser Tyr Trp Leu Glu
            820                 825                 830

Gln Gly Ser Gly Thr Asn Ser Ser Arg Glu Ser Asn Gly Thr Met Ala
        835                 840                 845

Asp Leu Gly Asn Ile Ala Asp Asn Pro Gln Leu Ser Phe Tyr Gln Leu
        850                 855                 860

Val Tyr Gly Leu Asn Ala Leu Leu Ile Cys Val Gly Val Cys Ser
865                 870                 875                 880

Ser Gly Ile Phe Thr Lys Val Thr Arg Lys Ala Ser Thr Ala Leu His
                885                 890                 895

Asn Lys Leu Phe Asn Lys Val Phe Arg Cys Pro Met Ser Phe Phe Asp
            900                 905                 910

Thr Ile Pro Ile Gly Arg Leu Leu Asn Cys Phe Ala Gly Asp Leu Glu
            915                 920                 925

Gln Leu Asp Gln Leu Pro Ile Phe Ser Glu Gln Phe Leu Val Leu
        930                 935                 940

Ser Leu Met Val Ile Ala Val Leu Leu Ile Val Ser Val Leu Ser Pro
945                 950                 955                 960

Tyr Ile Leu Leu Met Gly Ala Ile Ile Met Val Ile Cys Phe Ile Tyr
                965                 970                 975

Tyr Met Met Phe Lys Lys Ala Ile Gly Val Phe Lys Arg Leu Glu Asn
            980                 985                 990

Tyr Ser Arg Ser Pro Leu Phe Ser His Ile Leu Asn Ser Leu Gln Gly
            995                 1000                1005

Leu Ser Ser Ile His Val Tyr Gly Lys Thr Glu Asp Phe Ile Ser Gln
        1010                1015                1020

Phe Lys Arg Leu Thr Asp Ala Gln Asn Asn Tyr Leu Leu Leu Phe Leu
1025                1030                1035                1040

Ser Ser Thr Arg Trp Met Ala Leu Arg Leu Glu Ile Met Thr Asn Leu
                1045                1050                1055

Val Thr Leu Ala Val Ala Leu Phe Val Ala Phe Gly Ile Ser Ser Thr
            1060                1065                1070

Pro Tyr Ser Phe Lys Val Met Ala Val Asn Ile Val Leu Gln Leu Ala
        1075                1080                1085

Ser Ser Phe Gln Ala Thr Ala Arg Ile Gly Leu Glu Thr Glu Ala Gln
        1090                1095                1100

Phe Thr Ala Val Glu Arg Ile Leu Gln Tyr Met Lys Met Cys Val Ser
1105                1110                1115                1120

Glu Ala Pro Leu His Met Glu Gly Thr Ser Cys Pro Gln Gly Trp Pro
            1125                1130                1135

Gln His Gly Glu Ile Ile Phe Gln Asp Tyr His Met Lys Tyr Arg Asp
        1140                1145                1150

Asn Thr Pro Thr Val Leu His Gly Ile Asn Leu Thr Ile Arg Gly His
        1155                1160                1165

Glu Val Val Gly Ile Val Gly Arg Thr Gly Ser Gly Lys Ser Ser Leu
    1170                1175                1180

Gly Met Ala Leu Phe Arg Leu Val Glu Pro Met Ala Gly Arg Ile Leu
1185                1190                1195                1200

Ile Asp Gly Val Asp Ile Cys Ser Ile Gly Leu Glu Asp Leu Arg Ser
                1205                1210                1215

Lys Leu Ser Val Ile Pro Gln Asp Pro Val Leu Leu Ser Gly Thr Ile
            1220                1225                1230
```

-continued

```
Arg Phe Asn Leu Asp Pro Phe Asp Arg His Thr Asp Gln Gln Ile Trp
        1235            1240                1245
Asp Ala Leu Glu Arg Thr Phe Leu Thr Lys Ala Ile Ser Lys Phe Pro
1250                1255                1260
Lys Lys Leu His Thr Asp Val Val Glu Asn Gly Gly Asn Phe Ser Val
1265            1270            1275                    1280
Gly Glu Arg Gln Leu Leu Cys Ile Ala Arg Ala Val Leu Arg Asn Ser
                1285                1290                1295
Lys Ile Ile Leu Ile Asp Glu Ala Thr Ala Ser Ile Asp Met Glu Thr
            1300            1305            1310
Asp Thr Leu Ile Gln Arg Thr Ile Arg Glu Ala Phe Gln Gly Cys Thr
        1315            1320            1325
Val Leu Val Ile Ala His Arg Val Thr Thr Val Leu Asn Cys Asp His
    1330            1335            1340
Ile Leu Val Met Gly Asn Gly Lys Val Val Glu Phe Asp Arg Pro Glu
1345                1350            1355                1360
Val Leu Arg Lys Lys Pro Gly Ser Leu Phe Ala Ala Leu Met Ala Thr
                1365            1370            1375
Ala Thr Ser Ser Leu Arg
            1380
```